US009682947B2

(12) United States Patent
Huang et al.

(10) Patent No.: US 9,682,947 B2
(45) Date of Patent: Jun. 20, 2017

(54) SUBSTITUTED LACTONES FOR TREATING CANCER

(71) Applicants: KUNMING INSTITUTE OF BOTANY, CHINESE ACADEMY OF SCIENCES, Heilongtan, Kunming, Yunnan (CN); NEW YORK UNIVERSITY

(72) Inventors: Chuanshu Huang, New York, NY (US); Qin-Shi Zhao, Yunnan (CN); Zipeng Cao, New York, NY (US); Jingxia Li, New York, NY (US); Xu Deng, Yunnan (CN); Chao-Ming Li, Yunnan (CN)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/764,236

(22) PCT Filed: Jan. 29, 2014

(86) PCT No.: PCT/CN2014/071751
§ 371 (c)(1),
(2) Date: Jul. 29, 2015

(87) PCT Pub. No.: WO2014/117741
PCT Pub. Date: Aug. 7, 2014

(65) Prior Publication Data
US 2015/0361062 A1 Dec. 17, 2015

(30) Foreign Application Priority Data
Jan. 30, 2013 (CN) .......................... 2013 1 0034985

(51) Int. Cl.
*A61K 31/366* (2006.01)
*C07D 309/38* (2006.01)
*C07D 311/00* (2006.01)
*C07D 405/02* (2006.01)
*C07D 407/02* (2006.01)
*C07D 309/32* (2006.01)
*C07D 491/052* (2006.01)
*C07D 493/04* (2006.01)
*C07D 513/04* (2006.01)

(52) U.S. Cl.
CPC ....... *C07D 309/32* (2013.01); *C07D 491/052* (2013.01); *C07D 493/04* (2013.01); *C07D 513/04* (2013.01)

(58) Field of Classification Search
CPC .. A61K 31/366; C07D 309/38; C07D 311/00; C07D 405/02; C07D 407/02
USPC .......................... 514/456, 460; 549/283, 294
See application file for complete search history.

(56) References Cited

U.S. PATENT DOCUMENTS

2015/0361062 A1  12/2015  Huang et al.

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Siegel R, et al., Cancer Statistics for Hispanics/Latinos, CA Cancer J. Clin, 62, 10 (2012).
Newman DJ, et al., Natural products as sources of new drugs over the period 1981-2002, J. Nat Prod, 66 1022 (2003).
Soussi T., p53 alterations in human cancer: more questions than answers, Oncogene, 2007, 26:2145.
Vogelstein B, et al., Surfing the p53 network, Nature, 2000, 408:307.
Iwakuma T, et al., Crippling p53 activities via knock-in mutations in mouse models, Oncogene, 2007 26:2177.
Lan Yu-Hsuan, et al. Digoniodiol, deoxygoniopypyrone A, and oniofupyrone A: three new styryllactones from Goniothaalamus amuyon, Planta Medica, 2005, vol. 71, No. 2, pp. 153-159, see compounds 1-10.
Lan Yu-Hsuan, et al., Cytotoxic styrylpyrones from Goniothalamus amuyon, Journal of Natural Products, 2003, vol. 66, No. 4, pp. 487-490, see compounds 1-5.

* cited by examiner

*Primary Examiner* — Douglas M Willis
(74) *Attorney, Agent, or Firm* — Klauber & Jackson LLC

(57) ABSTRACT

Novel heterocyclo compounds represented by Formula I wherein X, R1, R2, R3, R4, R5, R6 and n are as described herein are provided. The compounds may be prepared as pharmaceutical compositions, and may be used for the prevention and treatment of a variety of cancer conditions in mammals including humans, including prostate, colon, bladder, melanoma, liver, breast, cervical, ovarian, esophagi, glialblastoma, pancreatic and lung cancer.

43 Claims, 14 Drawing Sheets

SUBSTITUTED LACTONES FOR TREATING CANCER

CROSS REFERENCE TO RELATED APPLICATIONS

Figure 1:
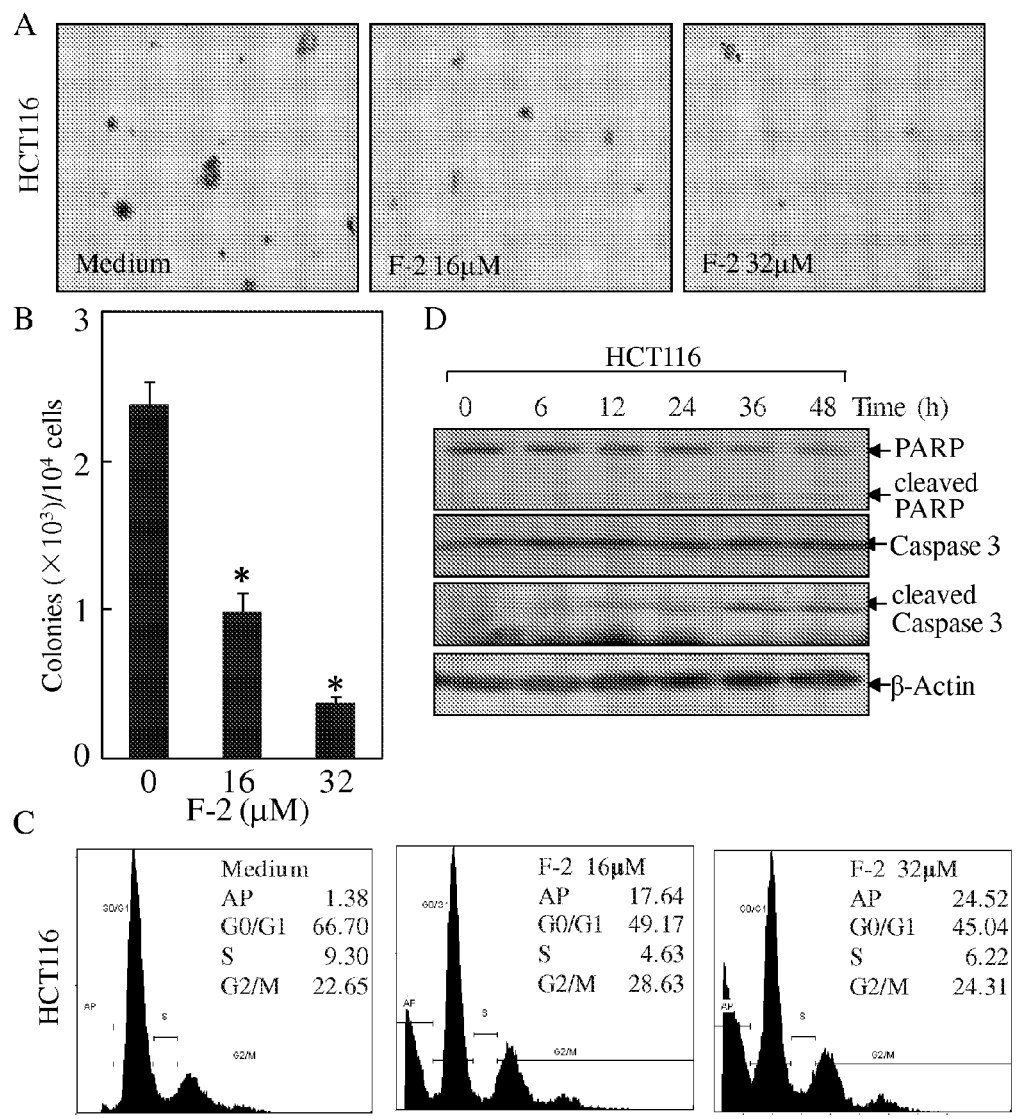

The present application is a National Stage Application claiming the priority of PCT Application No. PCT/CN2014/071751 filed Jan. 29, 2014, which in turn claims priority to Chinese Application Serial No. 2013/10034985.5 filed Jan. 30, 2013. Applicants claim the benefits of 35 U.S.C. §120 as to the PCT application, and priority under 35 U.S.C. §119 as to the Chinese application, and the entire disclosures of both applications are incorporated herein by reference in their entireties.

FIELD OF THE INVENTION

This invention relates to novel heterocyclo compounds capable of inducing apoptosis in cancer cell and uses of such compounds to treat cancer and related conditions. More particularly, the heterocyclo compounds may be used to induce apoptosis in cancer cells via p53-independent and p53/Bax- and PUMA-dependent pathway. Also encompassed herein, are compositions of novel heterocyclo compounds, pharmaceutical compositions of the heterocyclo compounds, assays and methods for using same to identify compounds capable of inducing apoptosis in cancer cells.

BACKGROUND OF THE INVENTION

Cancer is one of the leading causes of human death world-wide, accounting for 7.6 million deaths each year [Siegel R, et al. CA Cancer J Clin, 62, 10 (2012)]. Various therapies have been developed to treat cancer patients such as chemotherapy, radiotherapy and targeted therapy, immunotherapy and gene therapy. For decades, natural products have been a well spring of anticancer drugs and drug leads. According to a recent survey by National Cancer Institute, 74% of anticancer drugs worldwide during 1981-2002 can be traced to or were inspired by natural products [Newman D J, et al. J Nat Prod, 66, 1022 (2003)]. These includes natural products (6%), natural product derivatives (27%), synthetic compounds with natural-product-derived pharmacophores (5%), and synthetic compounds designed on the basis of knowledge gained from a natural product (23%). Since some chemical instability and poor water solubility, as well as its high toxicity to normal cells of the compounds isolated from natural products, their clinic application in the treatment of cancers is limited. Through the structure modification of the active natural compounds is an effective way to identify anti-tumor drug candidate. The resulting modified natural product needs to be effective in killing cancer cells with no and much less toxicity to normal cells, and thereby leads to promising anticancer drugs with no or less side effects in treatment of cancer patients.

Most cancers are characterized by impairment of p53 pathway, either by mutation of the p53 gene (TP53) (Soussi T. Oncogene, 2007, 26: 2145.), or by deregulation of expression of p53 and/or other p53-related components of the pathway (Vogelstein B, et al. Nature, 2000, 408: 307). The importance of p53 function as a tumor suppressors by mediating DNA-damaged cells undergoing apoptosis via its transcriptional regulation of Bax and PUMA, while it also causes cell growth arrest at G0 phase via mediating p21 expression when its induction is limited to certain extent. It is well known that at least 50% of human cancers carry TP53 mutations. Interestingly, the majority of the TP53 alterations are missense mutations leading to loss of its biological function with the expression of full-length point mutants (hereinafter identified also as mut-p53 or mutant p53) that accumulate to high levels in cancer cells. Basing on the high frequency of mutation and on the observation that p53 point mutants are highly abundant in invasive and high metastatic tumors, it has been accepted that mutant p53 proteins were associated with resistance to p53-dependent drugs commonly used in anti-cancer therapy (Iwakuma T, et al. Oncogene, 2007, 26: 2177). Given the active role of p53 mutants in drug resistance, the identification of new efficient chemotherapeutic drugs that could kill cancer cells via p53-independent cascade is desirable. However, the drugs with killing cancer cells via p53-independent manner are also highly toxic to normal cells of patients, which results in high side effects, and subsequently limiting the application of high drug doses and chemotherapeutic courses. Taken with consideration that p53-mediated normal cell growth arrest at G0 phase via p53/p21-dependent manner prevents the normal cells undergoing to apoptosis and that most of human cancer cells with p53 mutations will lost this p53 protection and further undergo to apoptosis upon p53-independent cascade, it may be beneficial to design and synthesize a kind of chemotherapeutic compounds that could lead to apoptosis in cancer cells via p53-independent and p53/Bax-PUNA-dependent pathway, whereas it mediates cell growth arrest of normal cells via p53/p21-dependent pathway, which will protect normal cells from killing of drugs. Thus, this kind of new drugs will be selectively killing cancer cells with no or less toxicity to normal cells, by which reduces their side effects on cancer patients.

In view of the above, a need exists for therapeutic agents, and corresponding pharmaceutical compositions and related methods of treatment of cancer that address selectively killing cancer cells with no or less toxicity to normal cells, and it is toward the fulfillment and satisfaction of that need, that the present invention is directed.

SUMMARY OF THE INVENTION

In one aspect, the present invention provides novel derivatives of a natural compound or a natural product that are effective in killing cancer cells with no or much less toxicity to normal cells, thereby leads to promising anticancer drugs with no or less side effects in treatment of cancer patients.

In a particular aspect, the present invention provides a compound according to formula I:

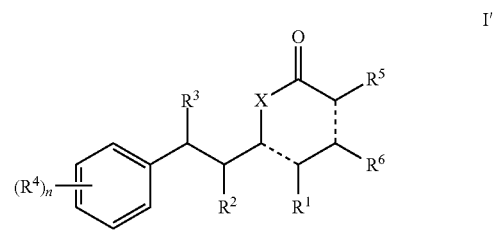

or a pharmaceutically acceptable salt, solvate or prodrug thereof;

and stereoisomers, isotopic variants and tautomers thereof;

wherein

X is —O—, or —NR$^x$—; R$^x$ is H or C$_1$-C$_6$ alkyl;

R$^1$ is H, OH, —OC(O)—R$^{y1}$, NH$_2$, —NR$^{z1}$R$^{z2}$, or —N(R$^{z3}$)—C(O)—R$^{z4}$;

R$^2$ is H, OH, —OC(O)—R$^{y2}$, NH$_2$, —NR$^{z5}$R$^{z6}$, —N(R$^{z7}$)—C(O)—R$^{z8}$;

each R$^{y1}$, R$^{y2}$, R$^{z2}$, R$^{z4}$, R$^{z6}$, and R$^{z8}$ is independently substituted or unsubstituted alkyl, substituted or unsubstituted aryl, or substituted or unsubstituted cycloalkyl; each R$^{z1}$, R$^{z3}$, R$^{z5}$, and R$^{z7}$ is independently H, substituted or unsubstituted alkyl, substituted or unsubstituted aryl, or substituted or unsubstituted cycloalkyl; or R$^{z5}$ and R$^{z6}$ together with the N they are attached to form a heterocycle;

or R$^1$ and R$^2$ are joined together to form —O—CR$^{w1}$R$^{w2}$—O—, —O—C(O)—O—, —NH—C(O)—NH—, or —NH—C(S)—NH—; each R$^{w1}$, and R$^{w2}$ is independently H, or substituted or unsubstituted alkyl;

R$^3$ is H or halo;

R$^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, substituted or unsubstituted dialkyl amido, halo, nitro, and thiol;

each R$^5$ and R$^6$ is independently H;

or R$^5$ and R$^6$ together with the Cs they are attached to form a carbocycle or heterocycle;

n is 1, 2, 3, 4 or 5; and each dotted bond is independently a single or a double bond;

provided that i) when R$^2$ is H; then R$^3$ is halo; and ii) the compound is other than

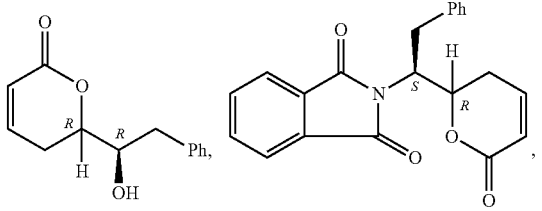

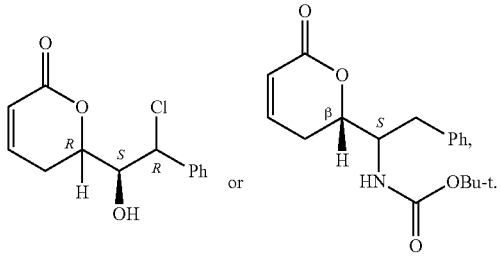

In one embodiment, with respect to the compound of formula I', when R$^2$ is H; then R$^3$ is halo In one embodiment, with respect to the compound of formula I', the compound is other than

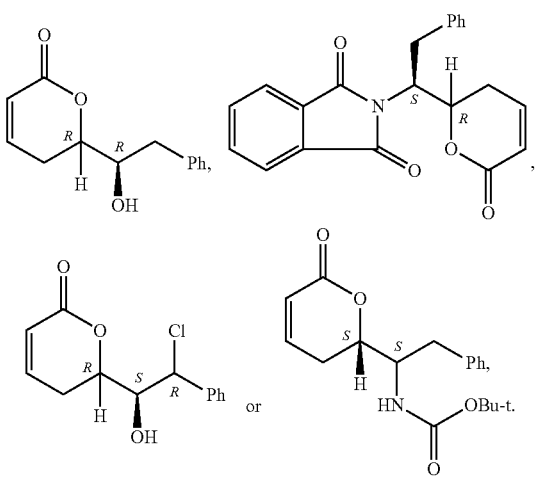

In one particular embodiment, with respect to the compound of formula I', the compound is according to formula IXb (Compound F2):

(Compound F2)

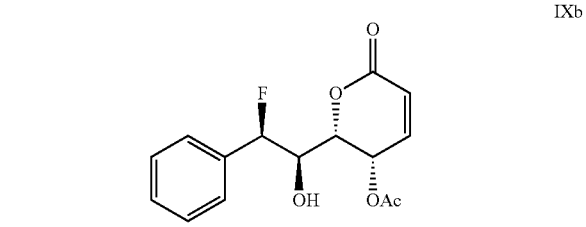

IXb or a pharmaceutically acceptable salt, solvate or prodrug thereof.

In yet another aspect, the present invention provides methods for preventing, treating or ameliorating in a mammal a disease or condition that is causally related to p53 activity in vivo, which comprises administering to the mammal an effective disease-treating or condition-treating amount of a compound according to formula I'. In one embodiment, the disease is cancer.

In yet another aspect, the present invention provides methods for inducing apoptosis in cancer cells via p53-independent pathway, which comprises contacting the cancer cell with a compound according to formula I'.

In yet another aspect, the present invention provides methods for inducing apoptosis in cancer cells via p53/Bax- and PUMA-dependent pathway, which comprises contacting the cancer cell with a compound according to formula I'.

In yet another aspect, the present invention provides methods for mediating cell growth arrest of normal cells via p53/p21-dependent pathway, which comprises contacting the cancer cell with a compound according to formula I'. In one embodiment, the compound protects apoptosis of normal cells.

In a further aspect, the present invention provides pharmaceutical compositions comprising a heterocyclic compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect, this invention provides a method of treating a mammal susceptible to or afflicted with cancer. In one embodiment, the cancer includes, without limitation, prostate, colon, bladder, melanoma, liver, breast, cervical, ovarian, esophagi, glialblastoma, and lung cancer. In another embodiment, the cancer includes, without limitation, pancreatic cancer. In another embodiment, the cancer includes, leukemia.

Other objects and advantages will become apparent to those skilled in the art from a consideration of the ensuing detailed description.

FIGURES

The details of the various figures depicting the activity of the compound F-2 of the invention are given below.

FIG. 1. Compound F-2 inhibited anchorage-independent growth and apoptosis of human colon cancer HCT116 cells. (A) HCT116 cells ($1 \times 10^4$) were exposed to different concentration of Compound F2 in 0.33% agar for 14 days as described in Example 1. The number of colonies was counted under microscopy at the end of the experiments. (B) The colonies are expressed as means±S.D. from six assays. *, p<0.05, significant decrease from vehicle control. (C) HCT116 cells were treated as indicated, with concentrated Compound F2 for 48 h. Apoptosis cells are present in the area indicated in each figure by flow-cytometric analysis. Treatments were performed as described in Example 1. Data represent one of three different experiments showing similar results. (D) Cleavage of caspase 3 and PARP was detected by Western Blotting after treatment of HCT116 cells with Compound F2 at 16 µM for time points as indicated. β-Actin was used as the protein loading control.

Figure 2:
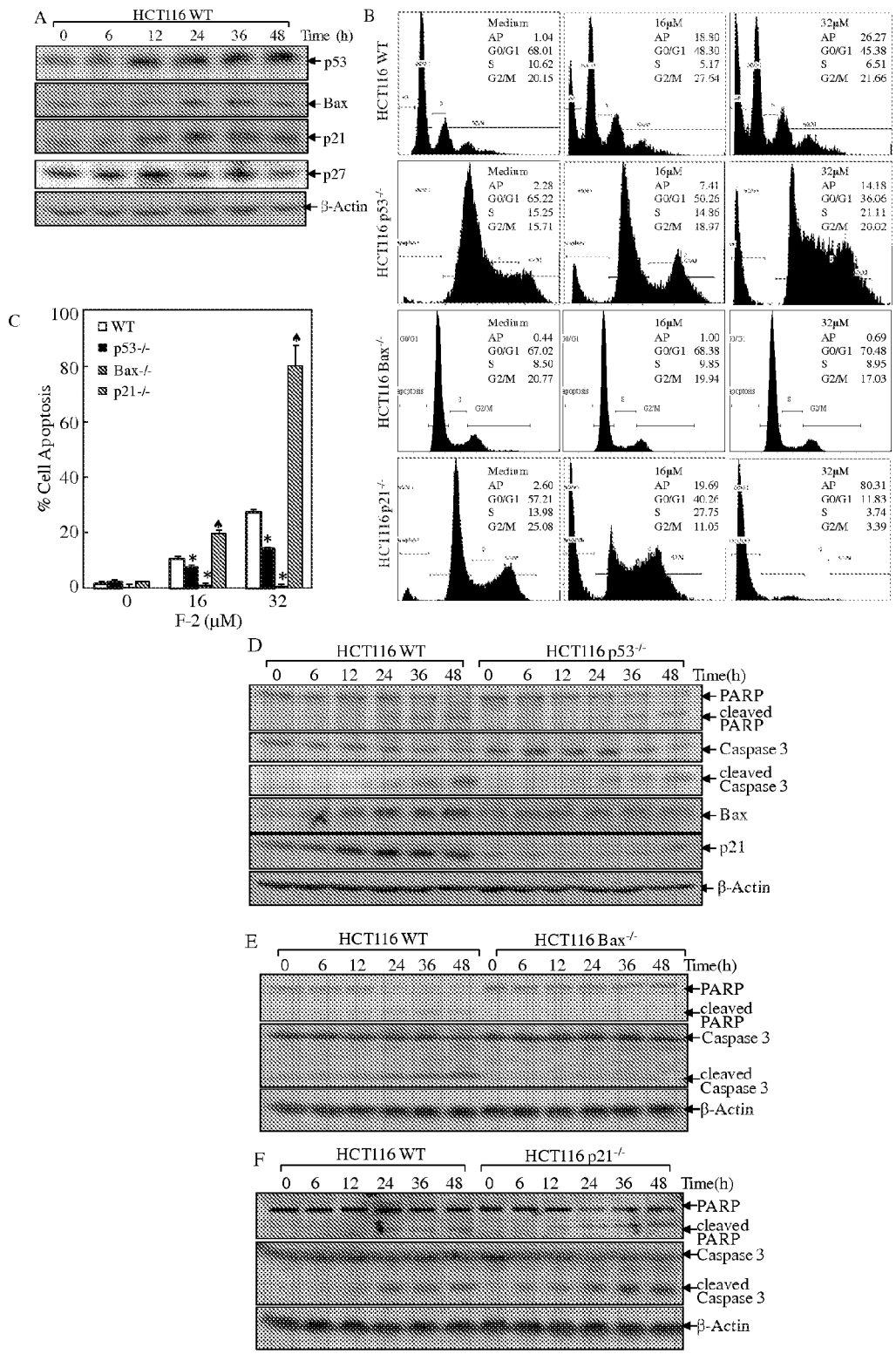

FIG. 2. Role of p53, Bax and p21 in cell death and growth arrest induced by Compound F2. (A) HCT116 wild-type cells were treated with Compound F2 at 16 µM for time points as indicated. Western blot analysis was performed to detect p53, Bax, p21 and p27 expression. (B) The indicated cells were treated with Compound F2 for 48 h and cell apoptosis and growth arrest were assayed by flow cytometry with propidium iodide (PI) staining (C) The ratio of cell apoptosis was evaluated in each condition from three independent experiments. "*", p<0.05, significant decrease from WT cells; and "♦" p<0.01, significant increase from WT cells. (D) HCT116 wild-type and p53-/- cells were treated with 16 µM Compound F2 for indicated time. Protein extracts were prepared and the expression of the indicated protein was analyzed by Western Blotting. (E) HCT116 wild-type and Bax-/- cells were placed under 16 µM Compound F2 for indicated time and subjected to Western Blotting. (F) HCT116 wild-type and p21-/- cells were placed under 16 µM Compound F2 for indicated time and subjected to Western Blotting.

Figure 3:
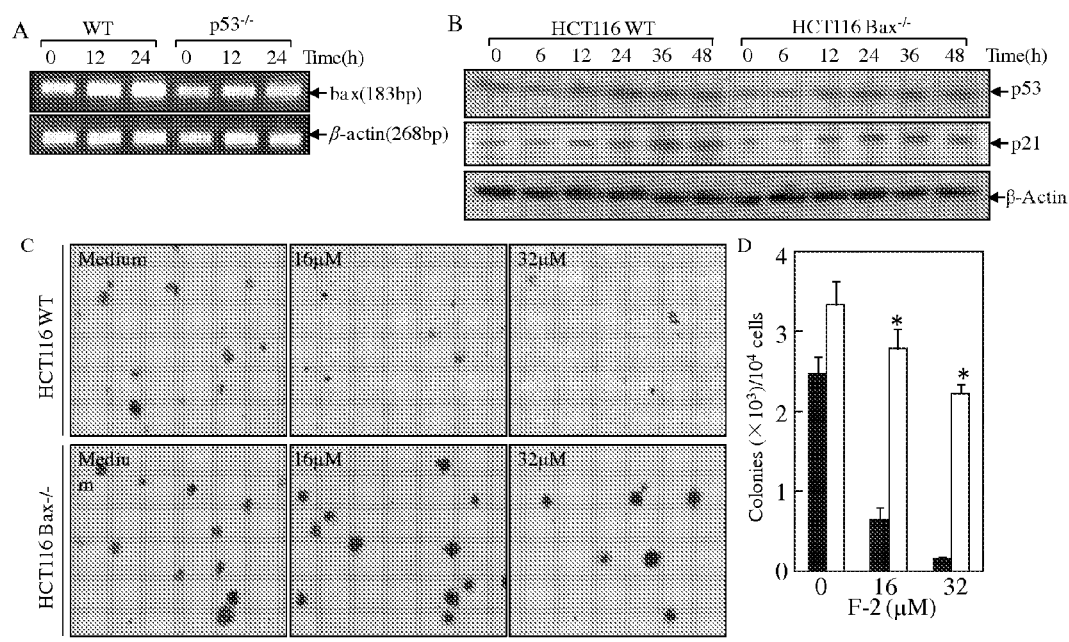
Figure 4:
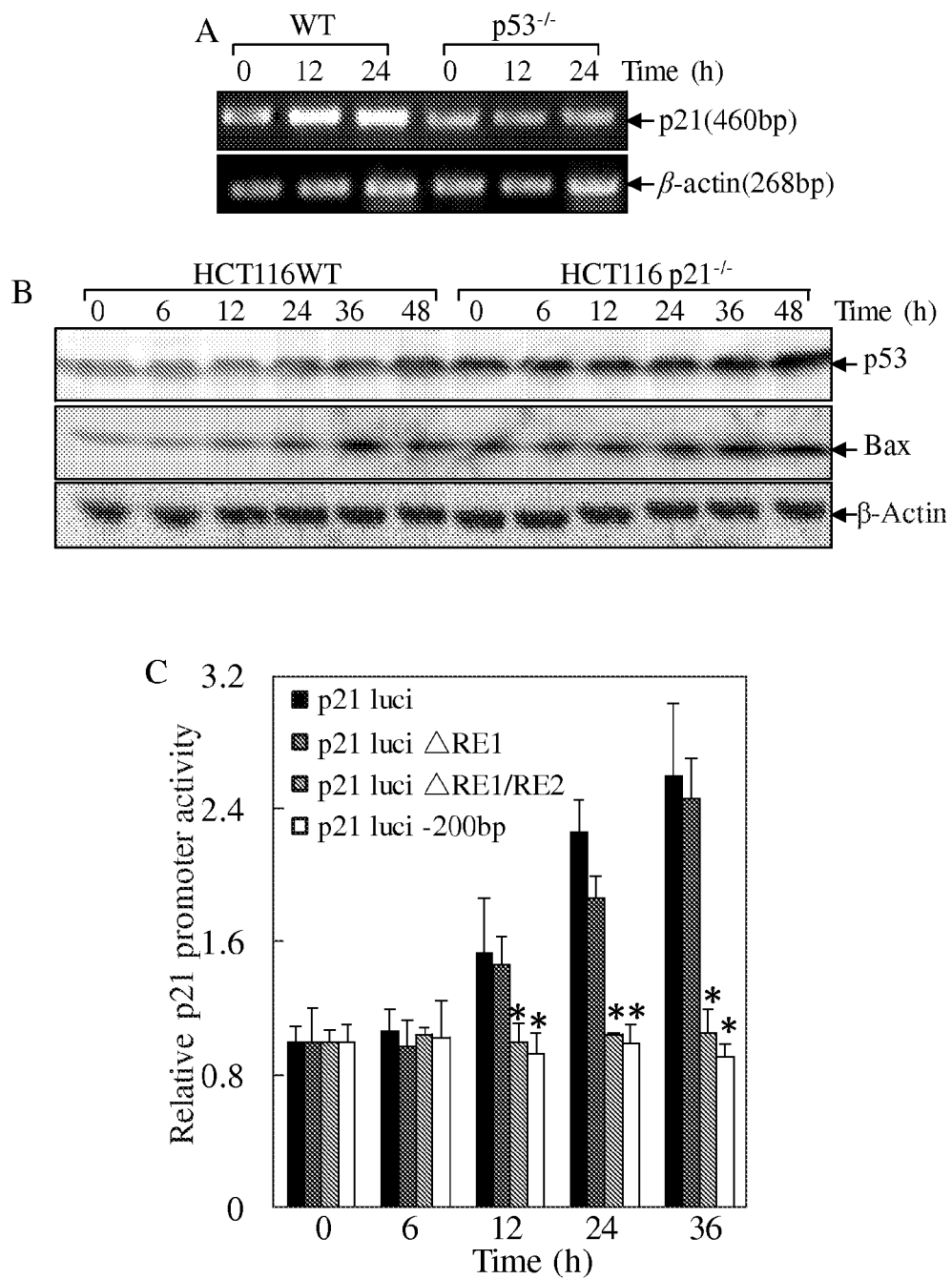

FIG. 3. Compound F2 treatment upregulated Bax mRNA expression in p53-independent manner. (A and B) HCT116 wild-type and p53-/- cells were placed under 16 µM Compound F2 for indicated time. (A) Total RNA were isolated and subjected to RT-PCR analysis or (B) HCT116 wild-type and Bax-/- cells were placed under 16 µM Compound F2 for indicated time. Cell protein extracts were subjected to Western Blotting as indicated. (C) HCT116 wild-type and Bax$^{-/-}$ cells ($1 \times 10^4$) were exposed to different concentration of Compound F2 in 0.33% agar for 14 days as described herein. The number of colonies was counted under microscopy at the end of the experiments. (D) The colonies are expressed as means±S.D. from six assays. "*", p<0.05, significant increase from WT cells FIG. 4. Compound F2 treatment upregulated p21 mRNA expression in p53-dependent manner. (A) HCT116 wild-type (WT) cells and p53-/- cells were placed under 16 µM Compound F2 for indicated time. Total RNA were isolated and subjected to RT-PCR analysis. (B) HCT116 WT and p21-/- cells were treated with 16 µM Compound F2 for indicated time, and then extracted for determination of p53 and Bax protein expression by Western Blotting. (C) HCT116 wild-type cells stably transfected with full-length and p53 binding site mutant p21 promoter-luciferase reporter were exposed to 16 µM Compound F2 for indicated time. The results were presented as the mean±S.D. from three independent experiments (*'p<0.05).

Figure 5:
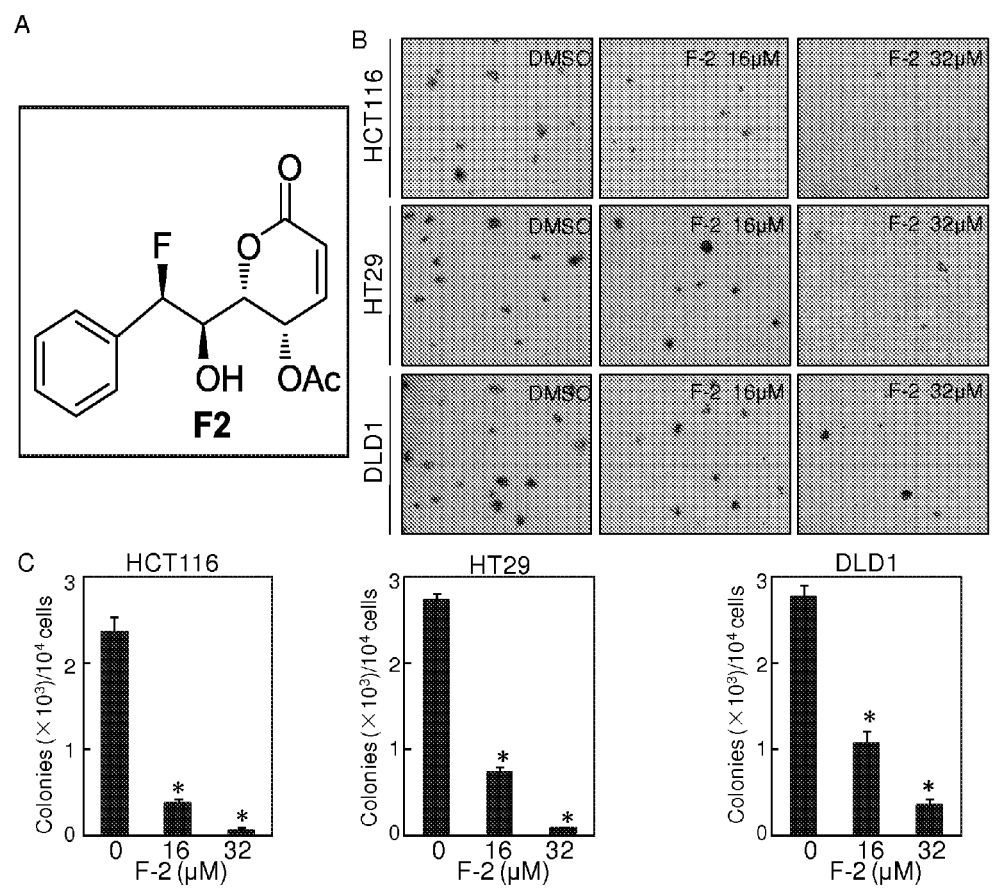

FIG. 5. Compound F2 blocked anchorage-independent growth of human colon cancer cells. (A), The structure of Compound F2. (B and C), HCT116, HT29 and DLD1 cells ($1 \times 10^4$) were exposed to vehicle control (0.2% DMSO), 16, 32 µM Compound F2 in 0.33% agar for 2 weeks. The colonies were captured and counted under microscopy. The colonies are expressed as means±S.E. from five assays. *, p<0.05, significant difference from vehicle control.

Figure 6:
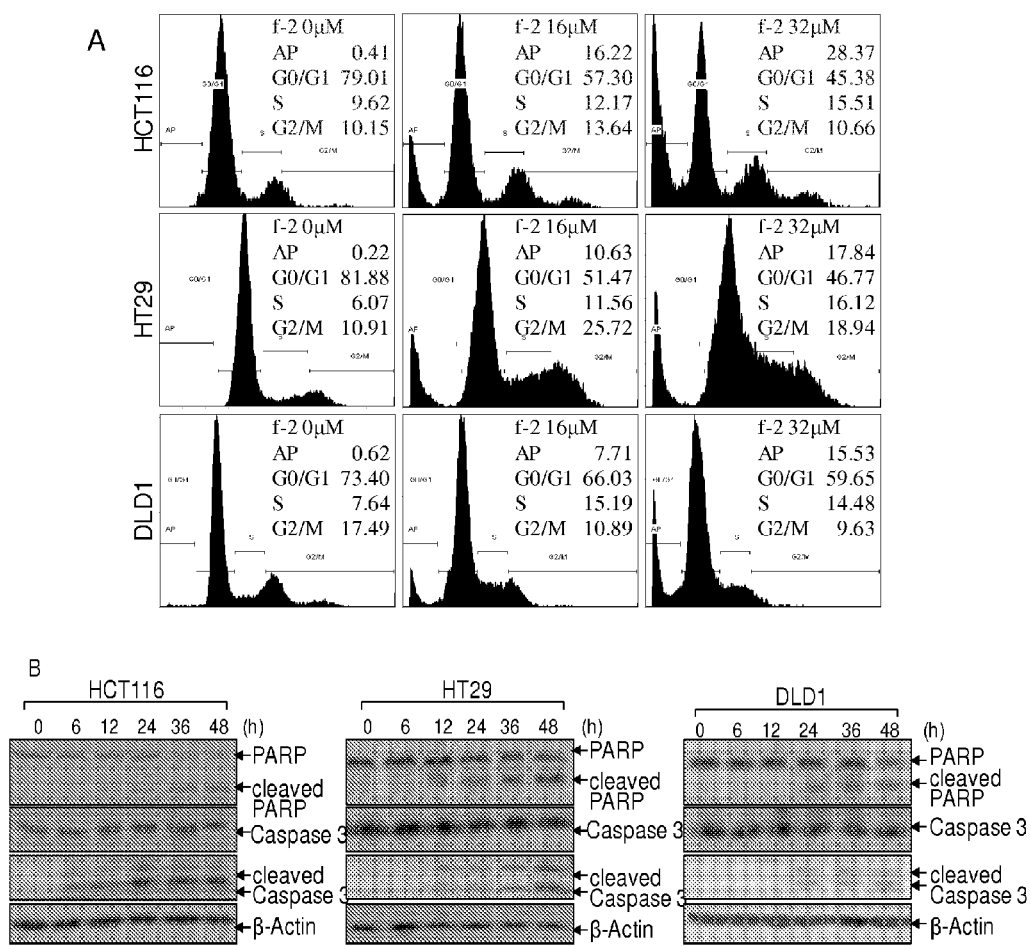

FIG. 6. Compound F2 induces cell apoptosis in human colon cancer cells. (A), HCT116, HT29 and DLD1 cells ($2 \times 10^5$) were seeded into each well of 6-well plates and cultured until the cell density reached 70-80% confluence. The cells were then exposed to vehicle control (0.2% DMSO), 16, 32 µM Compound F2 for 48 h. The cell death was determined by flow cytometry with PI staining. The result was representative one from three independent experiments. (B), HCT116 cells were exposed to 16 µM Compound F2 for indicated time. The whole cell protein were extracted and subjected to Western Blotting.

Figure 7:
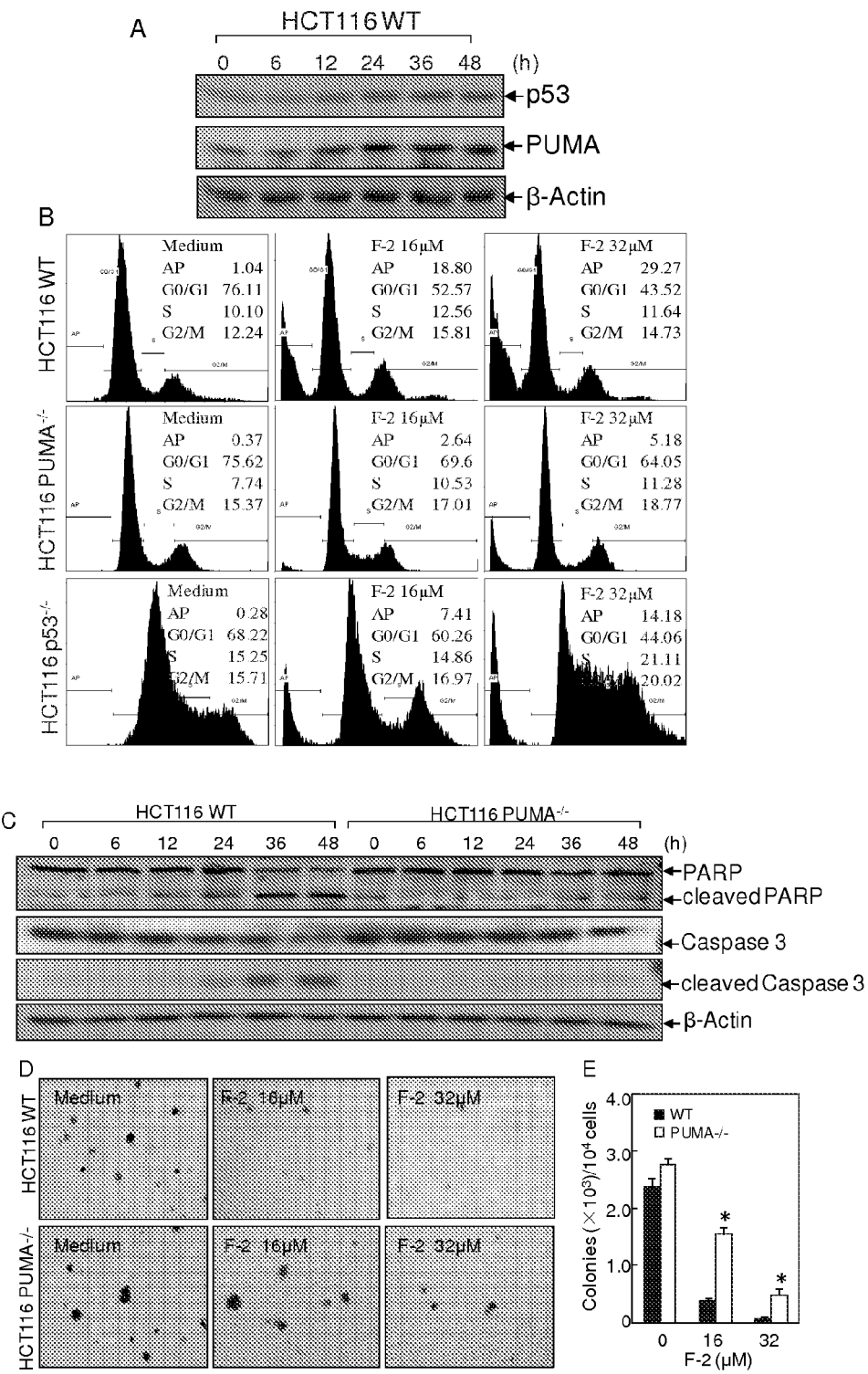

FIG. 7. Compound F2-induced cell apoptosis is in PUMA-dependent, and p53-independent manner (A), HCT116 cells were exposed to 16 µM Compound F2 for indicated time, and whole cell protein were extracted and subjected to Western Blot. (B), HCT116, HT29 and DLD1 cells were exposed to vehicle control (0.2% DMSO), 16 or 32 µM Compound F2 for 48 h. The cell death was determined by flow cytometry with PI staining (C), HCT116 WT and PUMA-/- cells were exposed to 16 µM Compound F2 for indicated time. The whole cell protein were extracted and subjected to Western Blot. (D & E), HCT116 WT and PUMA-/- cells ($1 \times 10^4$) were exposed to vehicle control (0.2% DMSO), 16, 32 µM Compound F2 in 0.33% agar for 2 weeks. The colonies were captured and counted under microscopy and expressed as means±S.E. from five assays. *, p<0.05, significant difference from WT cells.

Figure 8:
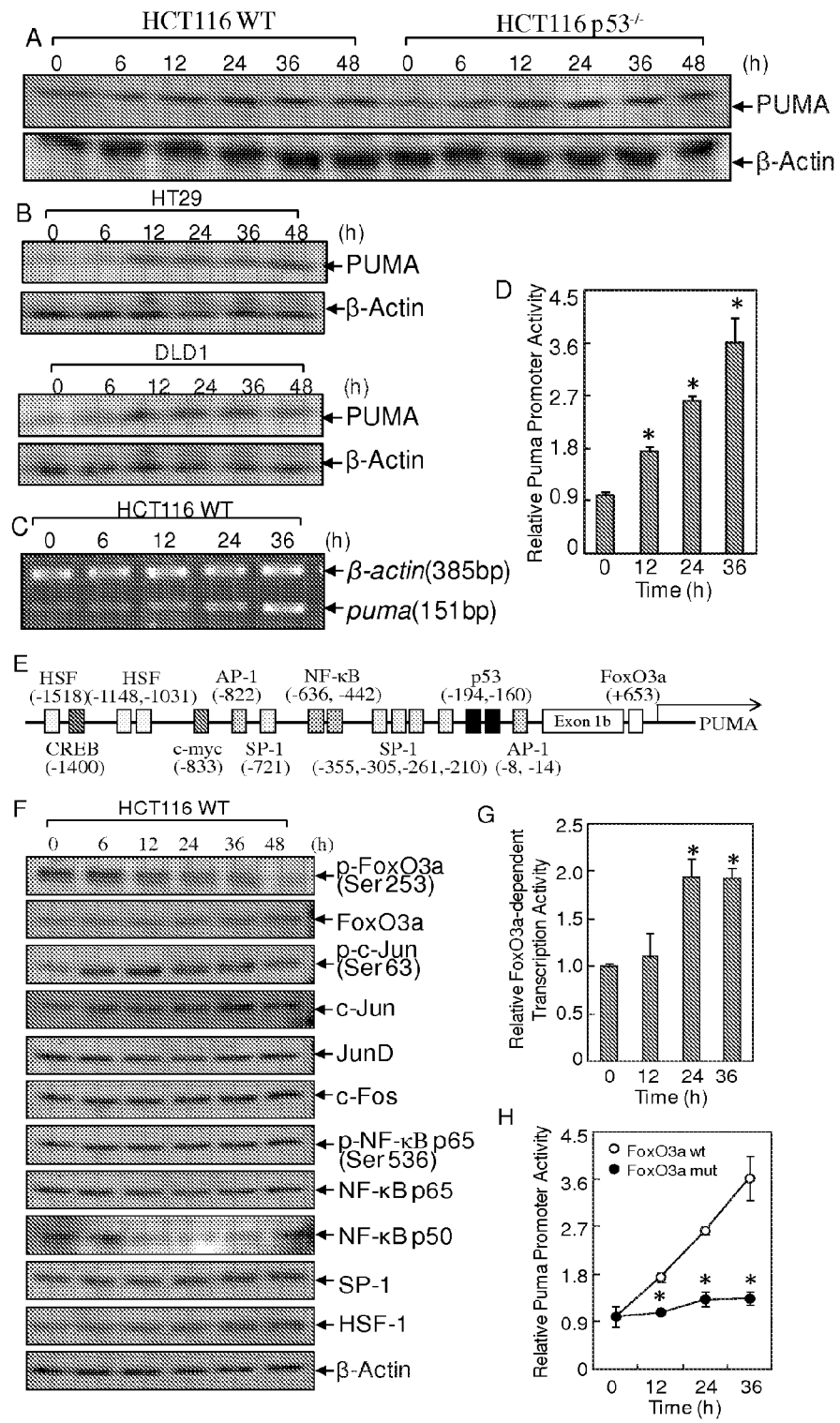

FIG. 8. Compound F2-induced PUMA upregulation is through p53-independent and FoxO3a-dependent pathway. (A), HCT116 WT and p53−/− cells were exposed to 16 μM Compound F2 for indicated time. The whole cell protein were extracted and subjected to Western Blot. (B), HT-29 and DLD-1 cells were exposed to 16 μM Compound F2 for indicated time. The whole cell protein were extracted and subjected to Western Blot. (C), HCT116 WT cells were exposed to 16 μM Compound F2 for indicated time. The whole cell mRNA was extracted and subjected to RT-PCR. (D), HCT116 WT cells stably transfected with PUMA promoter-driven luciferase reporter were exposed to 16 μM Compound F2 for indicated time, and then extracted for determination of the luciferase activity. (E), Schematic representation of transcription factor binding sites in PUMA promoter. (F), HCT116 WT cells were exposed to 16 μM Compound F2 for indicated time. The whole cell protein were extracted and subjected to Western Blot. (G), HCT116 WT cells stably transfected with FoxO3a transcription dependent (4×DBE) luciferase reporter were exposed to 16 μM Compound F2 for indicated time, and then extracted for determination of the luciferase activity. (H), HCT116 wWT-cells stably transfected with FoxO3a wt and FoxO3a mutant PUMA promoter-driven luciferase reporter were exposed to 16 μM Compound F2 for indicated time, and then extracted for determination of the luciferase activity.

Figure 9:
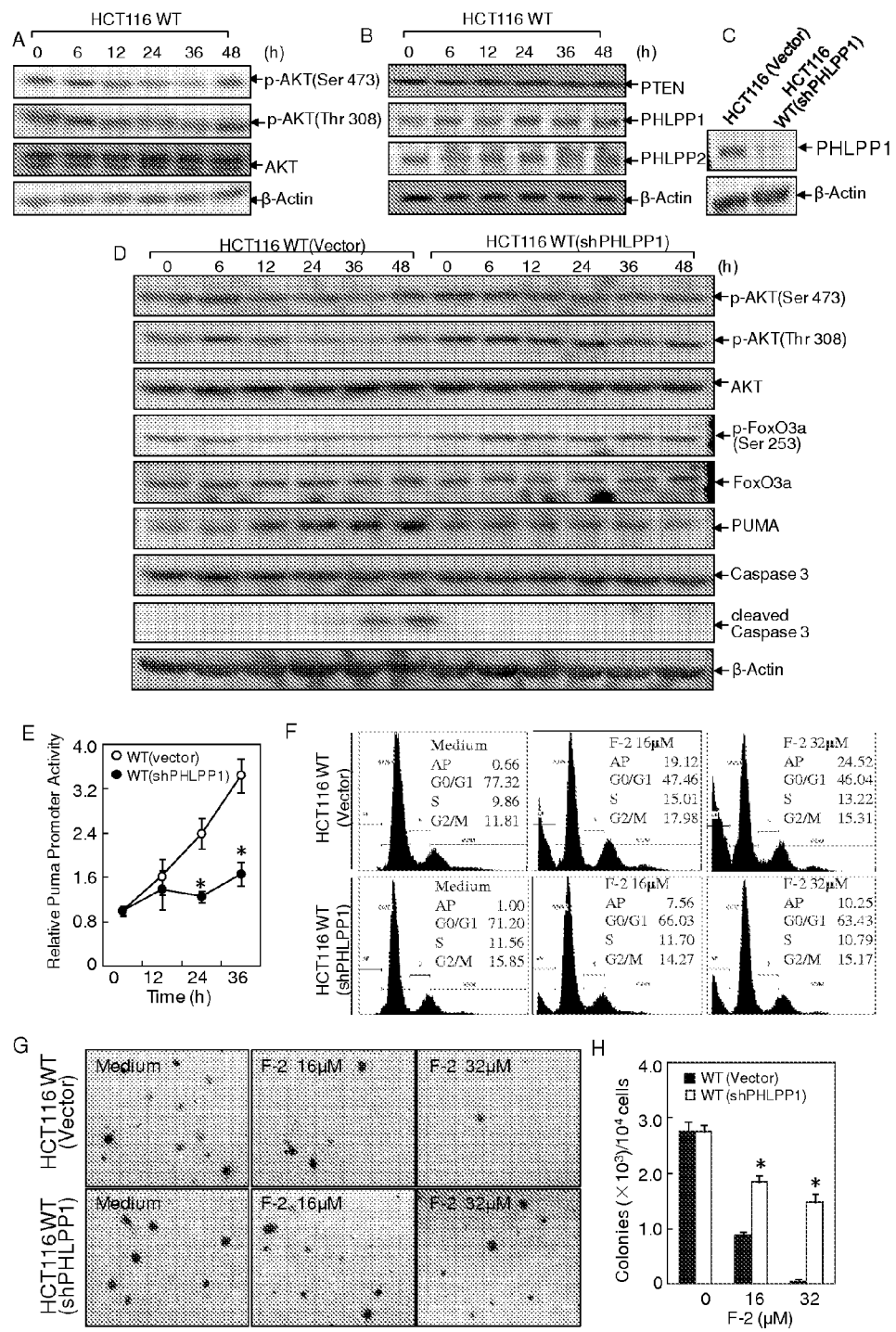

FIG. 9. Compound F2-induced FoxO3a transcription activity upregulation through PHLPP1/AKT axis
(A and B), HCT116 WT cells were exposed to 16 μM Compound F2 for indicated time. The whole cell protein were extracted and subjected to Western Blot. (C), HCT116 WT cells, stably transfected with shPHLPP1 or empty vector control, were extracted for Western Blot. (D), HCT116 WT cells stably transfected with shPHLPP1 or empty vector control were exposed to vehicle control or 16 or 32 μM Compound F2 for 48 hours, and cell extracts were applied for Western Blot. (E), HCT116 WT cells stably transfected with puma promoter-luciferase reporter together with either shPHLPP1 or empty vector control were exposed to vehicle control or 32 μM Compound F2 for indicated time, and cell extracts were applied for determination of luciferase activity. (F), HCT116 WT cells stably transfected with shPHLPP1 or empty vector control were exposed to vehicle control or 16 or 32 μM Compound F2 for 48 hours, and cell extracts were applied for flow cytometry with PI staining (G & H), HCT116 WT cells, stably transfected with shPHLPP1 vector or empty vector control, were exposed to vehicle control, 16, 32 μM Compound F2 for soft agar assay.

Figure 10:
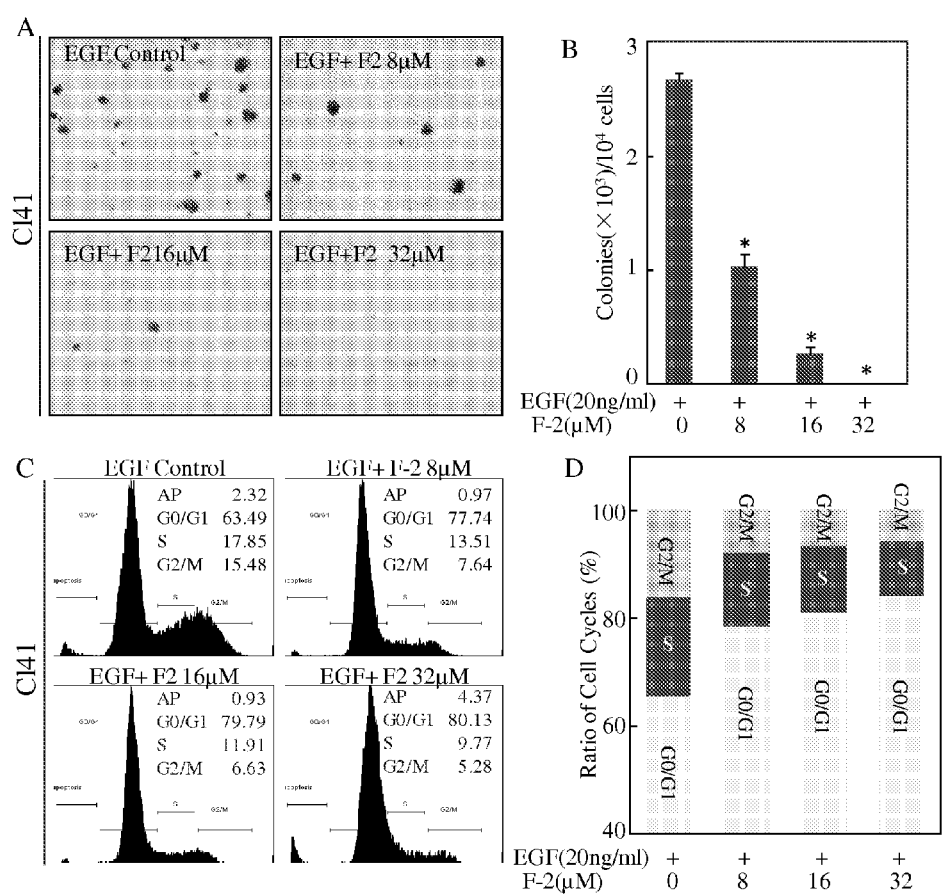

FIG. 10. Compound F2 inhibited EGF-induced cell transformation, cell proliferation, and induced G0/G1 growth arrest in Cl41 cells. (A & B) Cl41 cells were exposed to indicated concentrations of Compound F2 in combination with EGF for cell transformation assay in soft agar. The symbol (*) indicated a significant decrease in comparison to that of no Compound F2 treatment control (p<0.05). (C and D) Cl41 cells were seeded into each well of 6-well plates. After cells were treated for 24 h with EGF and Compound F2 at indicated concentrations, and the cell cycle was analyzed by flow cytometry with PI staining.

Figure 11:
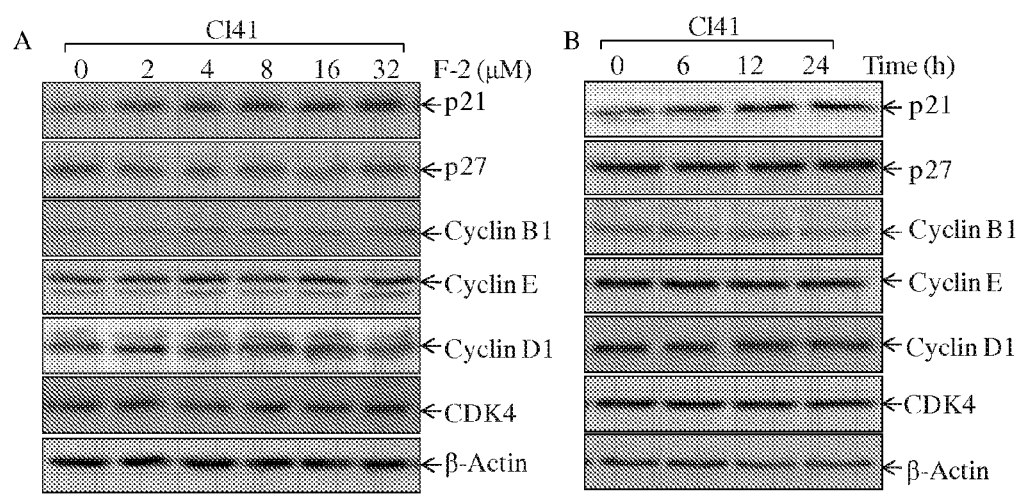

FIG. 11. Compound F2 induced p21 expression in Cl41 cells. (A and B) Cl41 cells were treated with Compound F2 in the indicated concentrations for 24 h (A), and indicated time under 16 μM Compound F2 treatment (B). Expression of β-actin was used as protein loading control. Data was representative one of three independent experiments.

Figure 12:
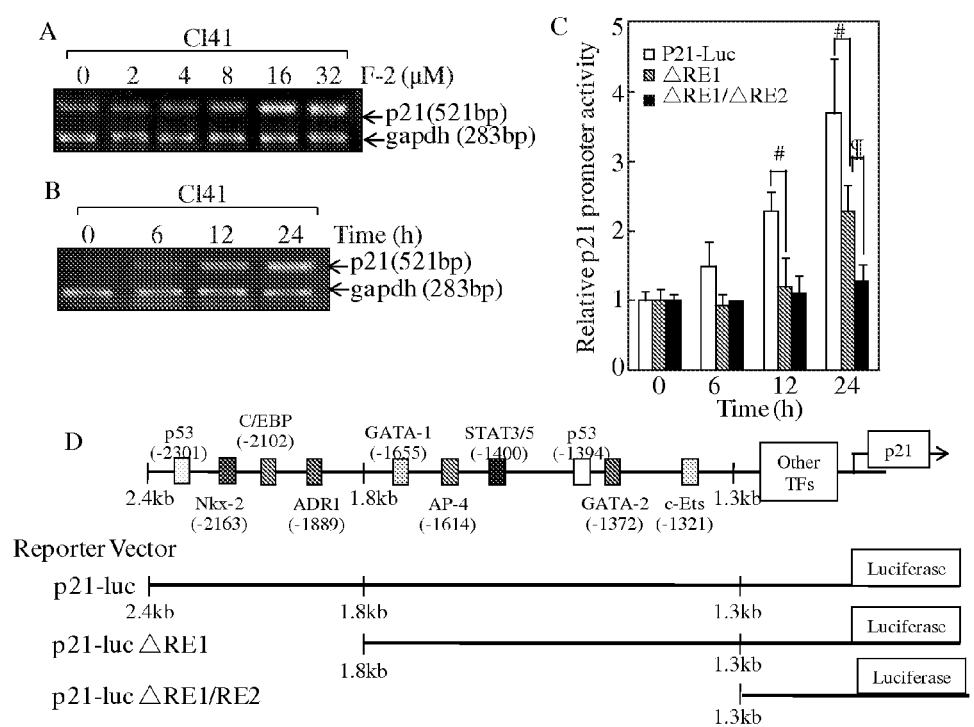

FIG. 12. Compound F2 upregulated p21 protein expression at the transcription level. (A) Cl41 cells were treated with Compound F2 in the indicated concentrations for 24 h, and the total RNA were isolated and subjected to RT-PCR analysis. (B) Cl41 cells were treated with medium containing either 0.2% DMSO or Compound F2 (16 μM) for indicated time, and the total RNA were isolated and subjected to RT-PCR analysis. (C) Cl41 cells stably transfected with either full length p21 promoter-driven luciferase reporter (p21-luc), or with p53 binding site deletions (p21-luc ΔRE1 or p21-luc ΔRE1/RE2) were exposed to 16 μM Compound F2 for indicated time, and then extracted for determination of the luciferase activity. (D) Schematic representation of transcription factor binding sites of p21 promoter.

Figure 13:
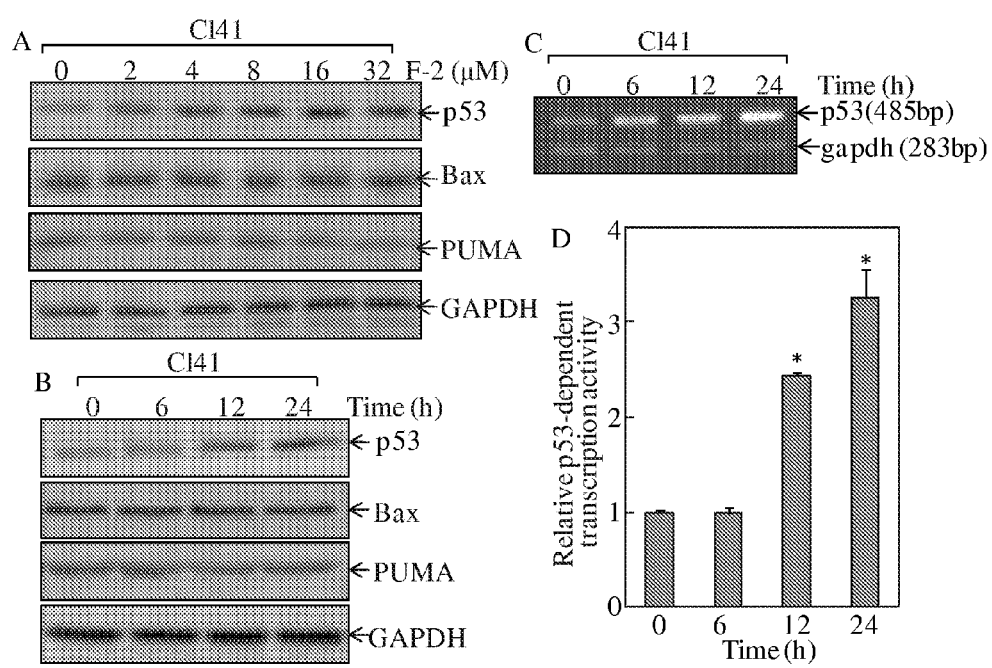

FIG. 13. Compound F2 treatment induced p53 protein expression and p53-dependent transactivation. (A and B) Cl41 cells were treated with different concentrations of Compound F2 for 24 hrs (A) or 16 μM Compound F2 for the indicated time (B). Total cell extracts were subjected to Western Blot. (C) Cl41 cells were treated with 16 μM Compound F2 for the indicated time. Total mRNA was extracts and subjected to RT-PCR determination of p53 mRNA induction. (D) p53-dependent luciferase reporter plasmid was stably co-transfected with the PRL-TK-Luciferase expression vector into Cl41 cells. Cell lysates were subjected to evaluate luciferase activity after treatment with 16 μM Compound F2 at the indicated times. The results were presented as mean±S.D. from three independent experiments. The symbol (*) indicated a significant increase in comparison to that of no Compound F2 treatment (p<0.05).

Figure 14:
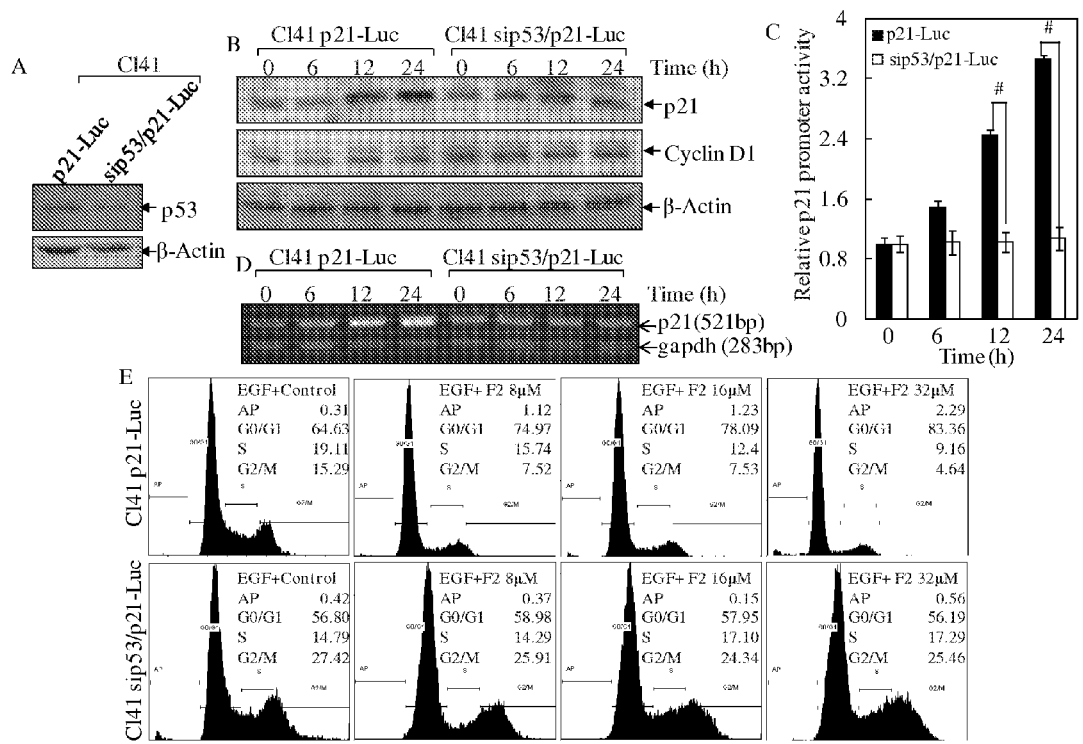

FIG. 14. p53 induction is crucial for Compound F2-induced p21 transcription and cell growth arrest in Cl41 cells. (A) identification of siRNA p53 knockdown of p53 expression in Cl41 cells by Western Blot. (B), Cl41 stable transfectants of mouse p53 shRNA or non-silencing control shRNA were exposed to 16 μM Compound F2 for indicated time and subjected to western blot. (C) Cl41 stable transfectants of p21-promoter luciferase reporter together with mouse p53 shRNA or non-silencing control shRNA were exposed to 16 μM Compound F2 for indicated time and subjected to RT-PCR for determination of p21-promoter drived luciferase activity. (D) Cl41 stable transfectants of mouse p53 shRNA or non-silencing control shRNA were exposed to 16 μM Compound F2 for indicated time and subjected to RT-PCR for determination of p21 mRNA induction. (E) Cl41 stable transfectants of mouse p53 shRNA or non-silencing control shRNA were exposed to EGF alone or combination with 8, 16, and 32 μM Compound F2 for 24 hrs and the cells were then subjected to flow cytometry with PI staining.

DETAILED DESCRIPTION OF THE INVENTION

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —C(O)R$^{20}$, where R$^{20}$ is hydrogen, alkyl, cycloalkyl, cyclohetereoalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR$^{21}$C(O)R$^{22}$, where R$^{21}$ is hydrogen, alkyl, cycloalkyl, cycloheteroalkyl, aryl, arylalkyl, heteroalkyl, heteroaryl, heteroarylalkyl and R$^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R$^{23}$ where R$^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O) OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^{30}$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O) NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O) NR$^{39}$R$^{39}$ where each R$^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

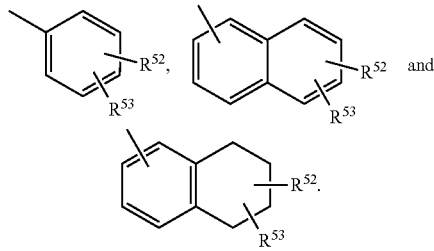

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

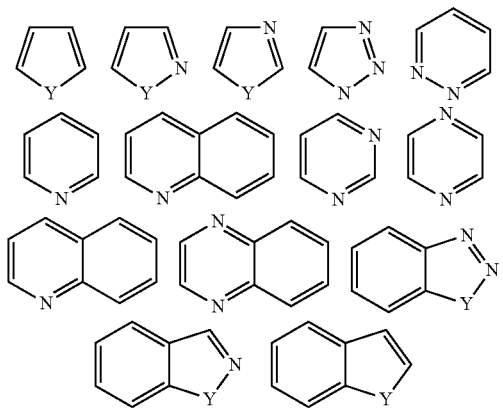

wherein each Y is selected from carbonyl, N, $NR^{58}$, O, and S; and $R^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

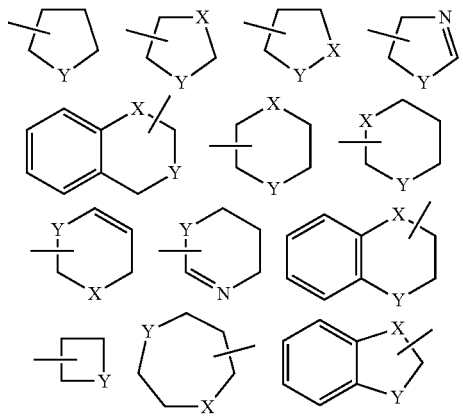

wherein each X is selected from $CR^{58}_2$, $NR^{58}$, O and S; and each Y is selected from $NR^{58}$, O and S; and $R^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

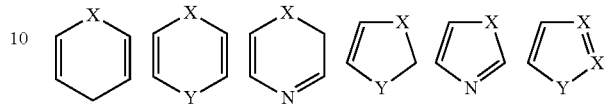

wherein each X is selected from $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

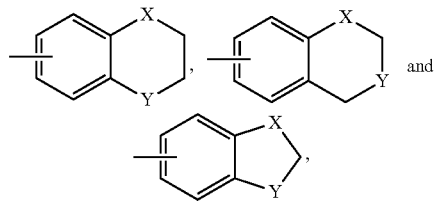

wherein each X is selected from C—$R^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an $R^4$ in a $R^4C$ group present as substituents directly on A, B, W, Y or Z of the compounds of this invention or may be present as a substituent in the "substituted" aryl and aliphatic groups present in the compounds.

Examples of hetero substituents include:
-halo,
—$NO_2$, —$NH_2$, —$NHR^{59}$, —$N(R^{59})_{29}$
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

"Hydrogen bond donor" group refers to a group containing O—H, or N—H functionality. Examples of "hydrogen bond donor" groups include —OH, —$NH_2$, and —NH—$R^{59a}$ and wherein $R^{59a}$ is alkyl, cycloalkyl, aryl, or heteroaryl.

"Dihydroxyphosphoryl" refers to the radical —$PO(OH)_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR$^{60}$ where R$^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R$^{61}$—(O$_2$)S— wherein R$^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as R$^{62}$$_2$N(O$_2$)S— wherein each R$^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", or "transduce", shall refer to any method or means by which a nucleic acid is introduced into a cell or host organism and may be used interchangeably to convey the same meaning Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_5$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

In one aspect, the present invention provides novel derivatives of a natural compound or a natural product that are effective in killing cancer cells with no or much less toxicity to normal cells, thereby leads to promising anticancer drugs with no or less side effects in treatment of cancer patients. In one embodiment, the present invention provides structural modification of cheliensisin A in order to prepare anticancer compounds.

In a particular aspect, the present invention provides compounds according to formula I:

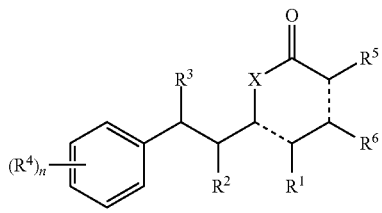

or a pharmaceutically acceptable salt, solvate or prodrug thereof;
and stereoisomers, isotopic variants and tautomers thereof;
wherein
X is —O—, or —NR$^x$—; R$^x$ is H or C$_1$-C$_6$ alkyl;
R$^1$ is H, OH, —OC(O)—R$^{y1}$, NH$_2$, —NR$^{z1}$R$^{z2}$, or —N(R$^{z3}$)—C(O)—R$^{z4}$;
R$^2$ is H, OH, —OC(O)—R$^{y2}$, NH$_2$, —NR$^{z5}$R$^{z6}$, —N(R$^{z7}$)—C(O)—R$^{z8}$;
each R$^{y1}$, R$^{y2}$, R$^{z2}$, R$^{z4}$, R$^{z6}$, and R$^{z8}$ is independently substituted or unsubstituted alkyl, substituted or unsubstituted aryl, or substituted or unsubstituted cycloalkyl;
each R$^{z1}$, R$^{z3}$, R$^{z5}$, and R$^{z7}$ is independently H, substituted or unsubstituted alkyl, substituted or unsubstituted aryl, or substituted or unsubstituted cycloalkyl; or R$^{z5}$ and R$^{z6}$ together with the N they are attached to form a heterocycle;
or R$^1$ and R$^2$ are joined together to form —O—CR$^{w1}$R$^{w2}$—O—, —O—C(O)—O—, —NH—C(O)—NH—, or —NH—C(S)—NH—; each R$^{w1}$, and R$^{w2}$ is independently H, or substituted or unsubstituted alkyl;
R$^3$ is H or halo;
R$^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkylthio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, substituted or unsubstituted dialkyl amido, halo, nitro, and thiol;
each R$^5$ and R$^6$ is independently H;
or R$^5$ and R$^6$ together with the Cs they are attached to form a carbocycle or heterocycle;
n is 1, 2, 3, 4 or 5; and
each dotted bond is independently a single or a double bond;
provided that
i) when R$^2$ is H; then R$^3$ is halo; and
ii) the compound is other than

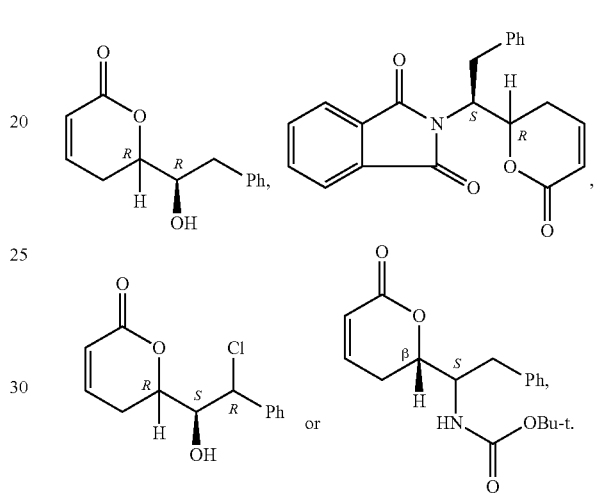

In one embodiment, with respect to the compound of formula I', when R$^2$ is H; then R$^3$ is halo.

In one embodiment, with respect to the compound of formula I', the compound is other than

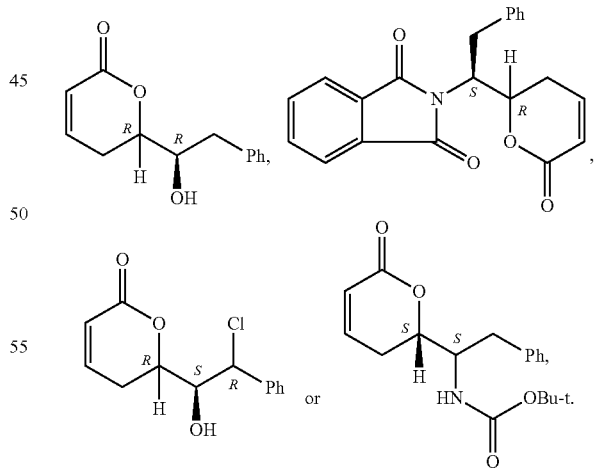

In another particular aspect, the present invention provides methods for preventing, treating or ameliorating in a mammal a disease or condition that is causally related to p53 activity in vivo, which comprises administering to the mammal an effective disease-treating or condition-treating amount of a compound according to formula I':

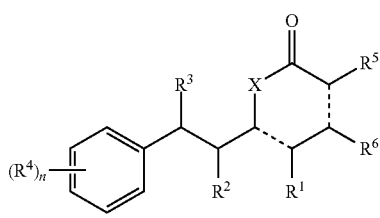

or a pharmaceutically acceptable salt, solvate or prodrug thereof;
and stereoisomers, isotopic variants and tautomers thereof;
wherein X, $R^1$, $R^2$, $R^3$, $R^4$, $R^5$, $R^6$, and n are as described herein; and each dotted bond is independently a single or a double bond.

In one embodiment, with respect to the compound of formula I', the dotted bond between $\underline{C}(R^5)$ and $\underline{C}(R^6)$ is a double bond; and each $R^5$ and $R^6$ is H.

In another embodiment, with respect to the compound of formula I', the dotted bond between $\underline{C}(R^5)$ and $\underline{C}(R^6)$ is a single bond; and $R^5$ and $R^6$ together with the Cs they are attached to form a heterocycle.

In another embodiment, with respect to the compound of formula I', the dotted bond between $\underline{C}(R^5)$ and $\underline{C}(R^6)$ is a single bond; and $R^5$ and $R^6$ together with the Cs they are attached to form a pyrazole ring.

In one embodiment, with respect to the compound of formula I', the dotted bond between $\underline{C}(R^1)$ and $\underline{C}(X)$ is a double bond.

In one embodiment, with respect to the compound of formula I', the compound is according to formula I:

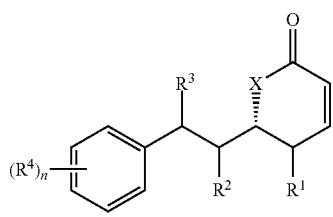

or a pharmaceutically acceptable salt, solvate or prodrug thereof;
and stereoisomers, isotopic variants and tautomers thereof;
wherein
X, $R^1$, $R^2$, $R^3$, $R^4$, and n are as described for formula I'.

In one embodiment, the compound is according to formula I; and $R^1$ is selected from hydrogen, hydroxy, acyloxy or aryl phenyl substituted by lower alkyl, acyloxy substituted by naphthyl, amine substituted by loweralkyl, amine substituted by $C_3$-$C_8$ cycloalkyl, amide substituted by loweralkyl, substituted amide or aryl phenyl by $C_3$-$C_8$ cycloalkyl, amide substituted by naphthyl, sulfonylamino substituted by lower alkyl, sulfonylamino or aryl phenyl substituted by $C_3$-$C_8$ cycloalkyl, sulfonylamino substituted by naphthyl, the chiral is R or S;

$R^2$ is selected from hydrogen, hydroxy, acyloxy or arylphenyl substituted by loweralkyl, acyloxy substituted by naphthyl, amine substituted by loweralkyl, amine substituted by $C_3$-$C_8$ cycloalkyl, amide substituted by loweralkyl, amide or arylphenyl substituted by $C_3$-$C_8$ cycloalkyl, amide substituted by naphthyl;

$R^3$ is selected from hydrogen, fluorine;

$R^4$ is selected from fluoro, chloro, bromo, iodo, hydroxy, nitro, amino substituted by loweralkyl, amino by substituted $C_3$-$C_8$ cycloalkyl;

$X^1$ is selected from oxygen, nitrogen;
or $R^1$ and $R^2$ are linked through carbonate, acetone, urea or thiourea bridge.

In one embodiment, $R^1$ is selected from hydrogen, hydroxy, acyloxy substituted by aryl (wherein aryl is phenyl or naphthyl substituted with lower alkyl or $C_3$-$C_8$ cycloalkyl), amino substituted by loweralkyl, amino substituted by $C_3$-$C_8$ cycloalkyl, amido substituted by loweralkyl, amido substituted by aryl, amido substituted by naphthyl, sulfonylamino substituted by loweralkyl, sulfonylamino substituted by aryl, and sulfonylamino substituted by naphthyl. The chirality is R or S.

In one embodiment, $R^2$ is selected from hydrogen, hydroxy, acyloxy substituted by aryl (wherein aryl is phenyl or naphthyl substituted with lower alkyl or $C_3$-$C_8$ cycloalkyl), amino substituted by loweralkyl, amino substituted by $C_3$-$C_8$ cycloalkyl, amido substituted by loweralkyl, amido substituted by aryl, and amido substituted by naphthyl.

In one embodiment, $R^3$ is selected from hydrogen, fluorine.

In one embodiment, each $R^4$ is independently selected from fluoro, chloro, bromo, iodo, hydroxy, nitro, amino substituted by loweralkyl, and amino substituted by $C_3$-$C_8$ cycloalkyl.

In one embodiment, X is selected from oxygen, and nitrogen.

In one embodiment, $R^1$ and $R^2$ are connected through an acetone, urea, carbonate or thiourea bridge.

In one embodiment, $R^3$ is H, Cl or F. In another embodiment, $R^3$ is H. In one particular embodiment, $R^3$ is F.

In one embodiment, with respect to the compound of formula I' or I, the compound is according to formula IIa or IIb:

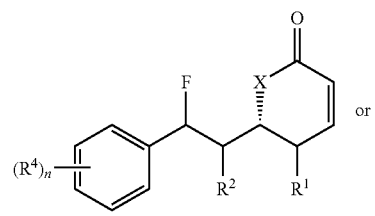

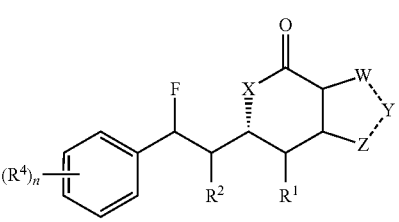

or a pharmaceutically acceptable salt, solvate or prodrug thereof;
and stereoisomers, isotopic variants and tautomers thereof;

and wherein n, X, $R^1$, $R^2$, and $R^4$ are as described for formula I'; each W, Y, and Z is
independently C, N, O, or S; and each double bond is independently single or a double bond.

In one embodiment, with respect to the compound of formula IIb, the dotted bond between W—Y is a single bond.

In one embodiment, with respect to the compound of formula IIb, the dotted bond between Y—Z is a double bond.

In one embodiment, with respect to the compound of formula I' or I, the compound is according to formula IIIa, IIIb, IIIc or IIId:

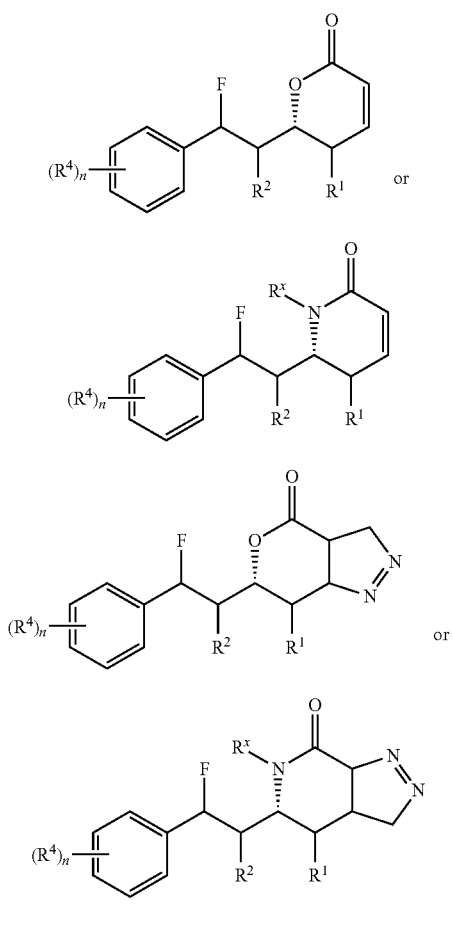

or a pharmaceutically acceptable salt, solvate or prodrug thereof;
and stereoisomers, isotopic variants and tautomers thereof;
and wherein n, $R^1$, $R^2$, $R^4$, and $R^x$ are as described for formula I'.

In one embodiment, $R^x$ is H, Me, Et, i-Pr, n-Pr, or t-Bu. In a particular embodiment, $R^x$ is H or Me.

In one embodiment, $R^1$ is H or OH. In another embodiment, $R^1$ is —OC(O)—$R^{y1}$; and $R^{y1}$ is substituted or unsubstituted alkyl. In another embodiment, $R^1$ is —OC(O)-Me, —OC(O)-Et, —OC(O)-t-Bu, or —OC(O)-Ph. In another embodiment, $R^1$ is OH or OAc.

In another embodiment, $R^1$ is $NH_2$, or —$NR^{z1}R^{z2}$; and $R^{z1}$ and $R^{z2}$ are as described for formula I'. $R^1$ is —N($R^{z3}$)—C(O)—$R^{z4}$; and $R^{z3}$ and $R^{z4}$ are as described for formula I'.

In another embodiment, $R^1$ is —NHAc, —$NMe_2$, —NH-t-Bu, or —N(H)—C(O)-t-Bu.

In another embodiment, $R^1$ is —$NR^{z1}R^{z2}$; and $R^{z1}$ and $R^{z2}$ together with the N they are attached to form a heterocycle.

In another embodiment, $R^1$ is piperidin-1-yl, morpholin-1-yl, pyrrolidin-1-yl, or piperizin-1-yl.

In one embodiment, with respect to the compound of formula I' or I, the compound is according to formula IVa, IVb, IVc, IVd, IVe, or IVf:

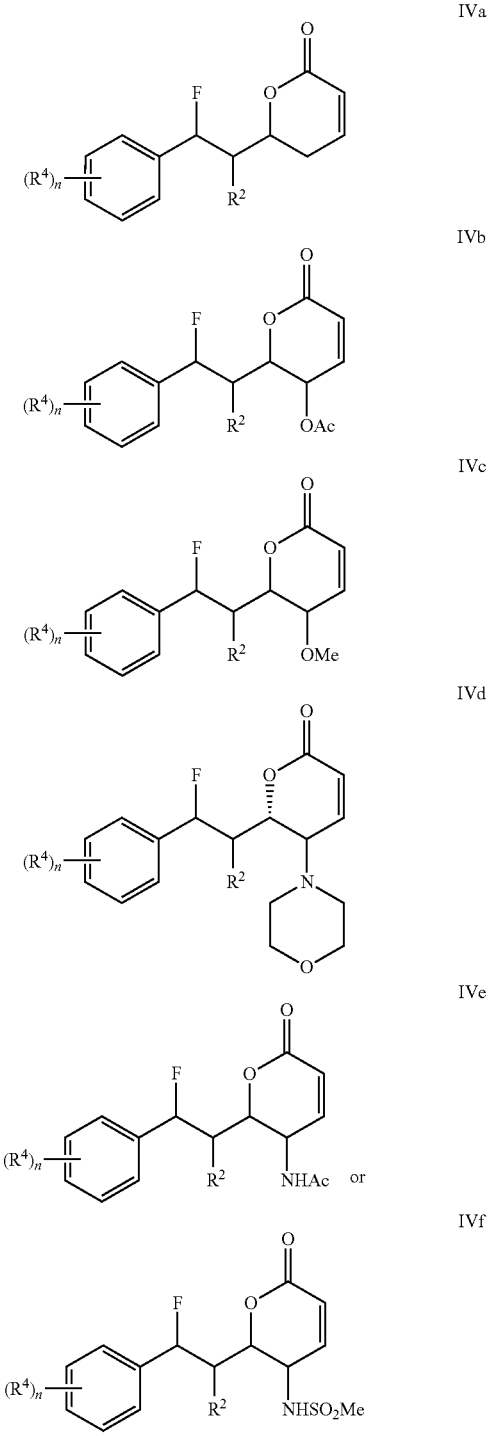

or a pharmaceutically acceptable salt, solvate or prodrug thereof;

and stereoisomers, isotopic variants and tautomers thereof;

and wherein n, $R^2$, and $R^4$ are as described for formula I'.

In one embodiment, with respect to the compound of formula I' or I, the compound is according to formula IVg or IVh:

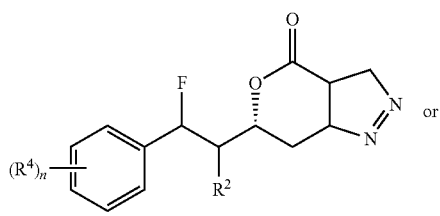
IVg

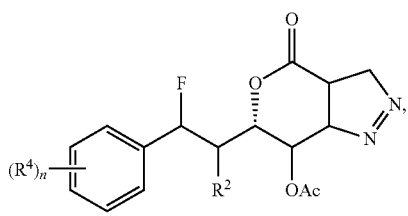
IVh or a pharmaceutically acceptable salt, solvate or prodrug thereof;

and stereoisomers, isotopic variants and tautomers thereof;

and wherein n, $R^2$, and $R^4$ are as described for formula I'.

In one embodiment, $R^2$ is H or OH. In another embodiment, $R^2$ is —OC(O)—$R^{y2}$; and $R^{y2}$ is substituted or unsubstituted alkyl. In another embodiment, $R^2$ is —OC(O)-Me, —OC(O)-Et, —OC(O)-t-Bu, or —OC(O)-Ph. In another embodiment, $R^2$ is OH or OAc.

In another embodiment, $R^2$ is $NH_2$, or —$NR^{z5}R^{z6}$; and $R^{z5}$ and $R^{z6}$ are as described for formula I'. $R^2$ is —N($R^{z7}$)—C(O)—$R^{z8}$; and $R^{z7}$ and $R^{z8}$ are as in claim 1.

In another embodiment, $R^2$ is —NHAc, —$NMe_2$, —NH-t-Bu, or —N(H)—C(O)-t-Bu.

In another embodiment, $R^2$ is —$NR^{z5}R^{z6}$; and $R^{z5}$ and $R^{z6}$ together with the N they are attached to form a heterocycle.

In another embodiment, $R^2$ is piperidin-1-yl, morpholin-1-yl, pyrrolidin-1-yl, or piperizin-1-yl.

In a particular embodiment, $R^2$ is OH.

In one embodiment, with respect to the compound of formula I' or I, the compound is according to formula Va, Vb, Vc, Vd, Ve, or Vf:

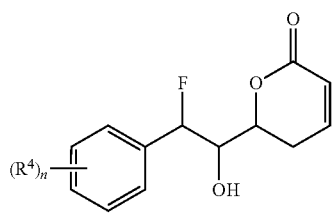
Va

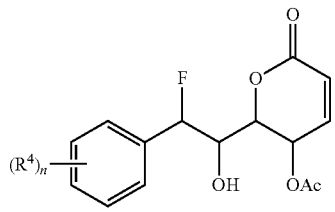
Vb

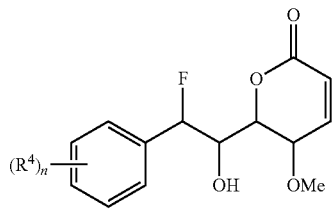
Vc

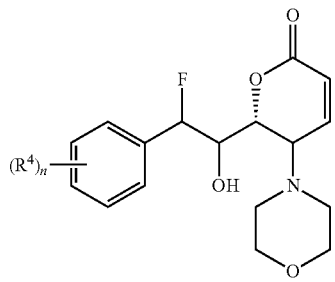
Vd

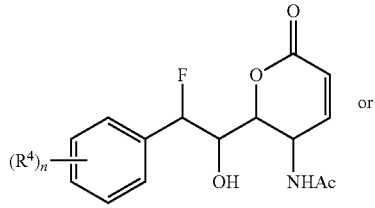
Ve

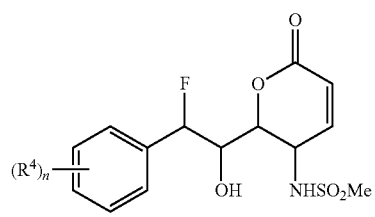
Vf or a pharmaceutically acceptable salt, solvate or prodrug thereof;

and stereoisomers, isotopic variants and tautomers thereof;

and wherein n, and $R^4$ are as described for formula I'.

In one embodiment, with respect to the compound of formula I' or I, the compound is according to formula Vg or Vh:

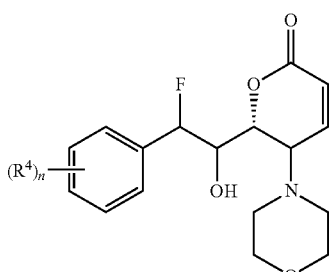

Vd

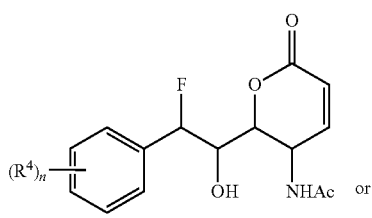

Ve

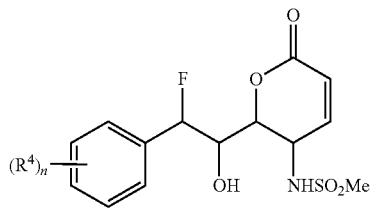

Vf or a pharmaceutically acceptable salt, solvate or prodrug thereof;

and stereoisomers, isotopic variants and tautomers thereof;

and wherein n, and $R^4$ are as described for formula I'.

In one embodiment, with respect to the compound of formula I' or I, the compound is according to formula Vg or Vh:

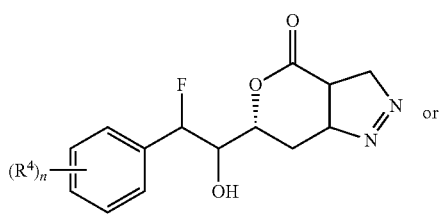

Vg

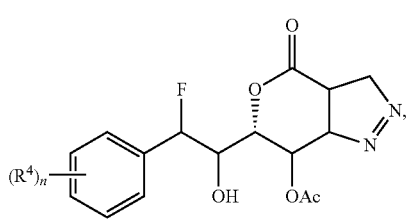

Vh or a pharmaceutically acceptable salt, solvate or prodrug thereof;

and stereoisomers, isotopic variants and tautomers thereof;

and wherein n, and $R^4$ are as described for formula I'.

In one embodiment, with respect to the compound of formula I' I, IIa, IIb, IIIa, IIIb, IIIc, or IIId, $R^1$ and $R^2$ are or a pharmaceutically acceptable salt, solvate or prodrug thereof;

and stereoisomers, isotopic variants and tautomers thereof;

and wherein n, and $R^4$ are as described for formula I'.

In one embodiment, $R^1$ and $R^2$ are joined together to form —O—CR$^{w1}$R$^{w2}$—O—, —O—C(O)—O—, —NH—C(O)—NH—, or —NH—C(S)—NH—; each R$^{w1}$, and R$^{w2}$ is independently H, or substituted or unsubstituted alkyl.

In another embodiment, $R^1$ and $R^2$ are joined together to form —O—C(Me)$_2$-O—, —O—C(O)—O—, —NH—C(O)—NH—, or —NH—C(S)—NH—.

In one embodiment, with respect to the compound of formula I' or I, the compound is according to formula Va, Vb, Vc, Vd, Ve, or Vf:

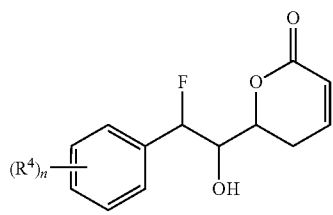

Va

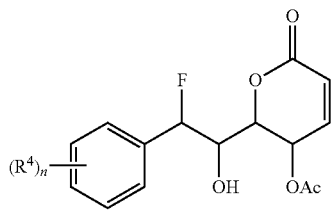

Vb

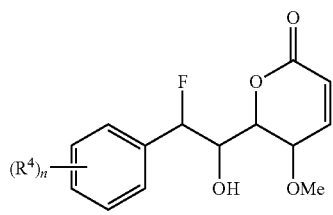

Vc joined together to form —O—CR$^{w1}$R$^{w2}$—O—, —O—C(O)—O—, —NH—C(O)—NH—, or —NH—C(S)—NH—; each R$^{w1}$, and R$^{w2}$ is independently H, or substituted or unsubstituted alkyl.

In one embodiment, with respect to the compound of formula I' I, IIa, IIb, IIIa, IIIb, IIIc, or IIId, R$^1$ and R$^2$ are joined together to form —O—C(Me)$_2$—O—, —O—C(O)—O—, —NH—C(O)—NH—, or —NH—C(S)—NH—.

In one embodiment, with respect to the compound of formula I' or I, the compound is according to formula VIa, VIb, VIc, VId, or VIe:

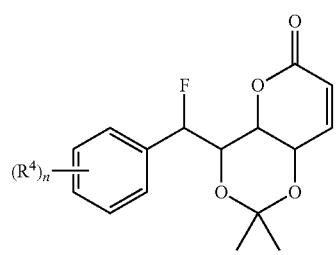
VIa

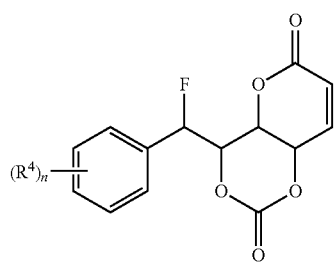
VIb

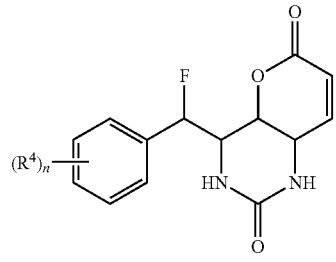
VIc

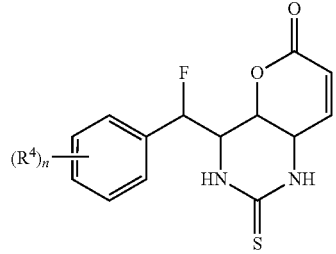
VId

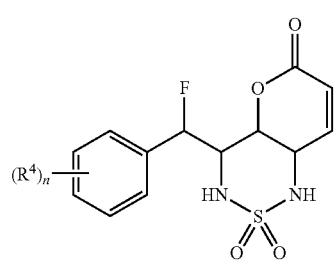
VIe or a pharmaceutically acceptable salt, solvate or prodrug thereof;

and stereoisomers, isotopic variants and tautomers thereof;

and wherein n, and R$^4$ are as described for formula I'.

In one embodiment, with respect to the compound of formula I' I, IIa-IIb, IIIa-IIId, IVa-IVh, Va-Vh, VIa-VId, n is 1 or 2; and each R$^4$ is independently halo, alkyl, haloalkyl, hydroxyl, alkoxy, nitro, cyano, amino, alkylamino, or dialkylamino.

In one embodiment, with respect to the compound of formula I' I, IIa-IIb, IIIa-IIId, IVa-IVh, Va-Vh, VIa-VId, n is 1 or 2; and each R$^4$ is independently F, Cl, CN, OH, Me, CF$_3$, or NMe$_2$.

In one embodiment, with respect to the compound of formula I' I, IIa-IIb, IIIa-IIId, IVa-IVh, Va-Vh, VIa-VId, each R$^4$ is H.

In one embodiment, with respect to the compound of formula I' or I, the compound is according to formula VIIa, VIIb, VIIc, VIId, VIIe, or VIIf:

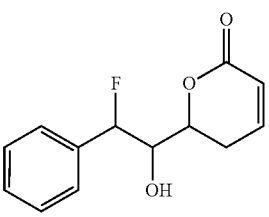
VIIa

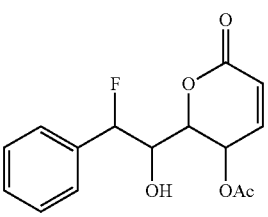
VIIb

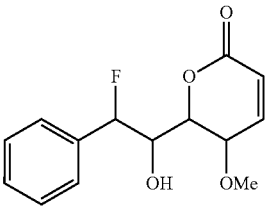
VIIc

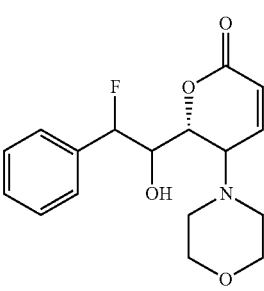
VIId

VIIe

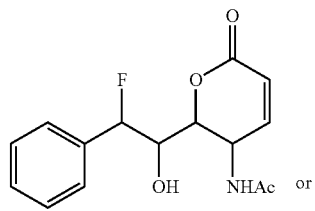

or

VIIf

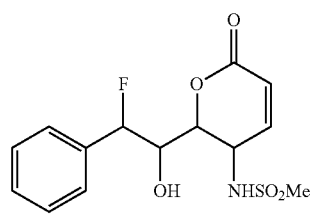

or a pharmaceutically acceptable salt, solvate or prodrug thereof;
and stereoisomers, isotopic variants and tautomers thereof.

In one embodiment, with respect to the compound of formula I' or I, the compound is according to formula VIIg or VIIh:

VIIg

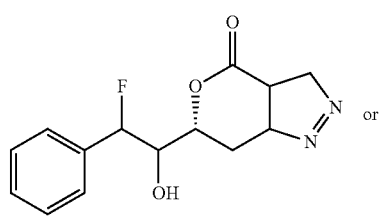

or

VIIh

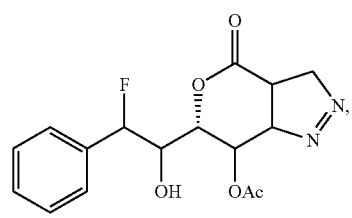

or a pharmaceutically acceptable salt, solvate or prodrug thereof;
and stereoisomers, isotopic variants and tautomers thereof.

In one embodiment, with respect to the compound of formula I' or I, the compound is according to formula VIIIa, VIIIb, VIIIc, VIIId, or VIIIe:

VIIIa

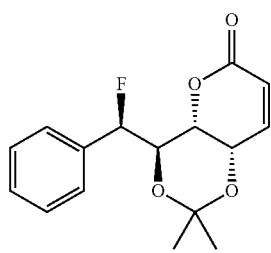

VIIIb

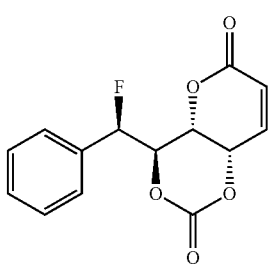

VIIIc

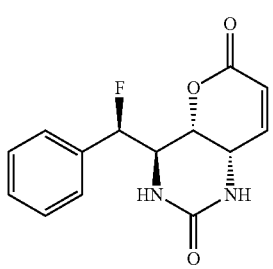

VIIId

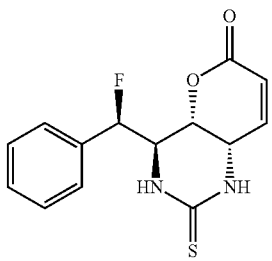

VIIIe

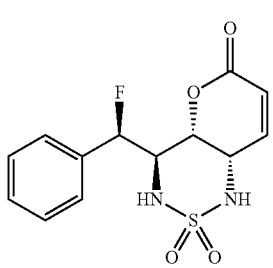

or a pharmaceutically acceptable salt, solvate or prodrug thereof;
and stereoisomers, isotopic variants and tautomers thereof.

In one particular embodiment, with respect to the compound of formula I' or I, the compound is according to formula IXa, IXb, IXc, IXd, IXe, or IXf:

IXa

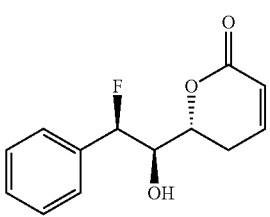

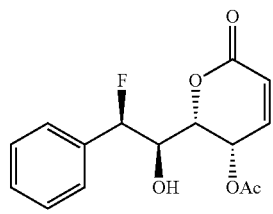
IXb

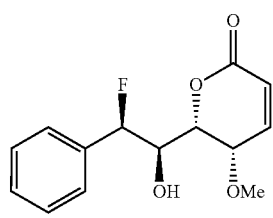
IXc

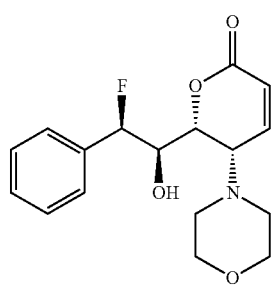
IXd

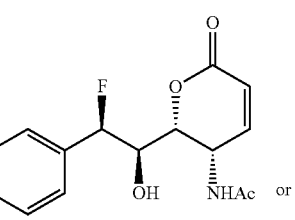
IXe

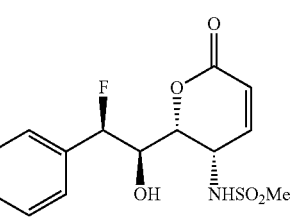
IXf or a pharmaceutically acceptable salt, solvate or prodrug thereof;

and stereoisomers, isotopic variants and tautomers thereof.

In another particular embodiment, with respect to the compound of formula I' or I, the compound is according to formula IXg or IXh:

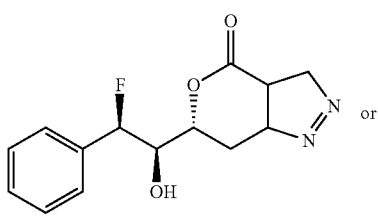
IXg

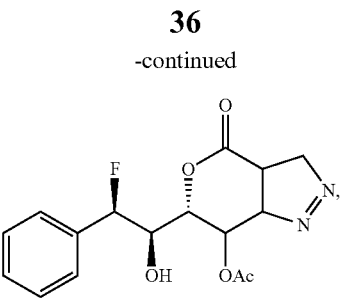
IXh or a pharmaceutically acceptable salt, solvate or prodrug thereof;

and stereoisomers, isotopic variants and tautomers thereof.

In another particular embodiment, with respect to the compound of formula I' or I, the compound is according to formula Xa, Xb, Xc, Xd, or Xe:

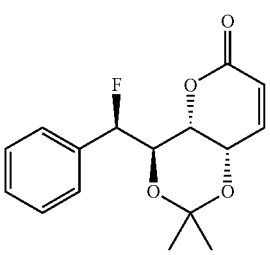
Xa

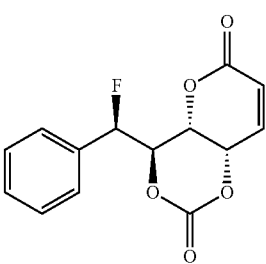
Xb

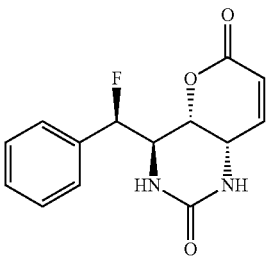
Xc

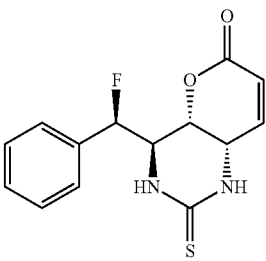
Xd

Xe
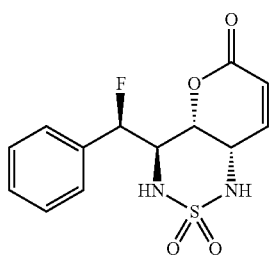
or a pharmaceutically acceptable salt, solvate or prodrug thereof;
and stereoisomers, isotopic variants and tautomers thereof.
In a more particular embodiment, with respect to the compound of formula I' or I, the compound is
2
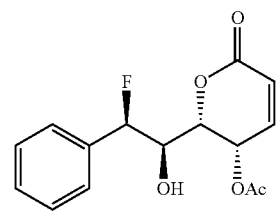
3
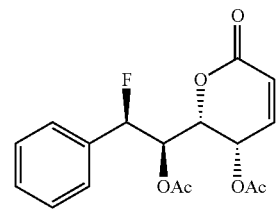
4
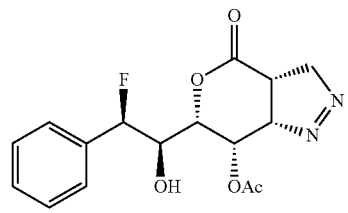
5
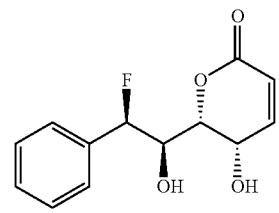
6
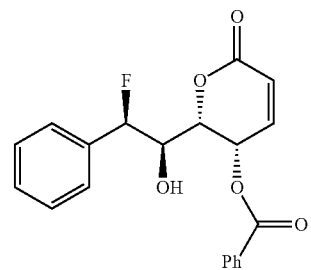
7
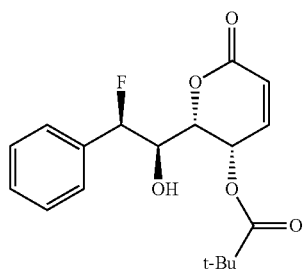
8
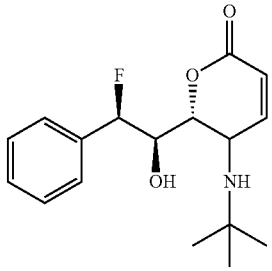
9
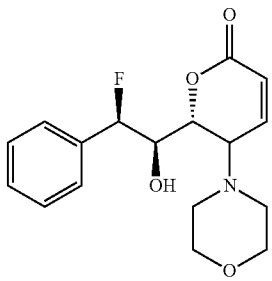
10
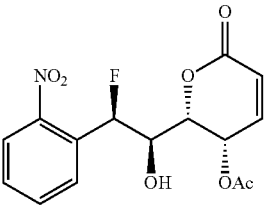
11
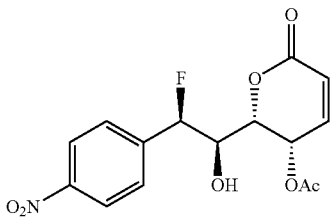
12
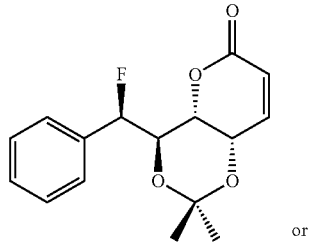
or

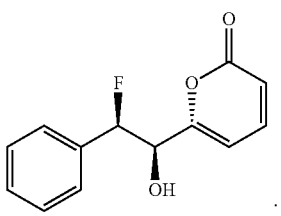

13

In a most particular embodiment, with respect to the compound of formula I' or I, the compound is according to formula IXb (Compound X):

(Compound X)

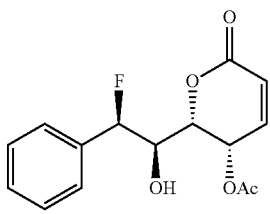

IXb or a pharmaceutically acceptable salt, solvate or prodrug thereof.

In one embodiment, with respect to the compound of formula I, the compound is any one of compounds listed in Table 1.

In yet another aspect, the present invention provides pharmaceutical compositions of a compound according to formula I' or I-Xd.

In one embodiment, the pharmaceutical composition comprises a pharmaceutically acceptable carrier.

In one embodiment, the carrier is a parenteral carrier, oral or topical carrier.

In one embodiment, with respect to the method, the disease or condition is cancer.

In one embodiment, with respect to the method, the disease or condition is cancer of prostate, colon, bladder, melanoma, liver, breast, cervical, ovarian, esophagi, glialblastoma, or lung.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_5$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in Remington's Pharmaceutical Sciences.

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to p53 pathway. Accordingly, the compounds and pharmaceutical compositions of this invention find use as therapeutics for preventing and/or treating a variety of cancers in mammals, including humans.

In a method of treatment aspect, this invention provides a method of treating a mammal susceptible to or afflicted with a condition associated with cancer, which method comprises administering an effective amount of one or more of the pharmaceutical compositions just described.

In additional method of treatment aspects, this invention provides methods of inducing apoptosis in cancer cells via p53-independent and p53/Bax- and PUNA-dependent pathway, whereas it mediates cell growth arrest of normal cells via p53/p21-dependent pathway, which will protect normal cells from killing of drugs.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of cancers.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery mode/s based on a variety of parameters, including the organ or tissue site in a patient with a disease or condition that is most severely affected by the disease or condition.

When used to prevent the onset of cancer, the compounds of this invention will be administered to a patient at risk for developing the cancer, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and are determined to safe and efficacious for such combined administration.

General Synthetic Procedures

The heterocyclo compounds of this invention may be purchased from various commercial sources or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds of the invention may be prepared from known or commercially available starting materials and reagents by one skilled in the art of organic synthesis.

General Materials and Methods:

All commercially available reagents and solvents were purchased and used without further purification. ESI-MS experiments were performed on a Shimadzu LCMS-2010EV mass spectrometer. 1D and 2D NMR experiments were performed on a Bruker AM-300 and DRX-500 NMR spectrometer. Deuterated reagents were purchased from Sigma Aldrich. Chemical shifts were given in δ with TMS as internal reference. The unit of δ was ppm, and J was Hz. Chromatography separations were performed with 300-400 mesh silica gels. Thin layer chromatography was carried out on 0.4-0.5 mm silica plates. The silica gels and plates were prepared by Yantai Jiangyou Silica Gel Development Co., Ltd. Analytically pure solvents were purchased from Tianjin Chemical Co., Ltd.

The following general procedures were used to synthesize compounds having different but analogous structures. One skilled in the art of synthesis will recognize how to modify these general procedures if necessary to accomplish the desired transformations.

Representative Synthetic Methods

Example C-1

General Method for Preparation of the Compounds of Invention

The representative 8-fluoro-7-hydroxy compounds of the invention can be prepared using the general synthetic pathway depicted in Scheme 1.

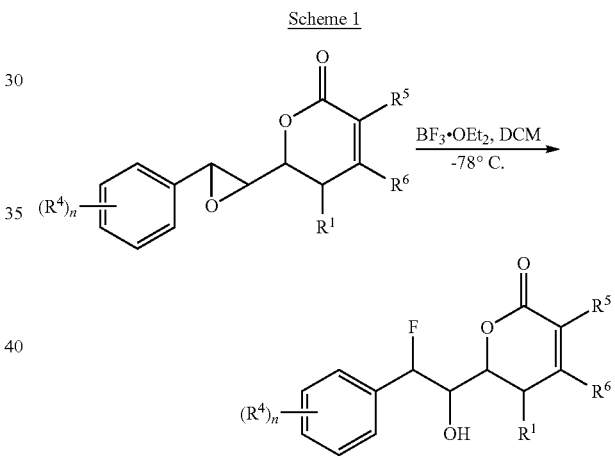

and wherein $R^1$, $R^4$, $R^5$, $R^6$, and n are as described herein.

The 8-fluoro-7-hydroxy compounds can further used to prepare representative Compounds 2-13 using the synthetic pathway depicted in Scheme 2.

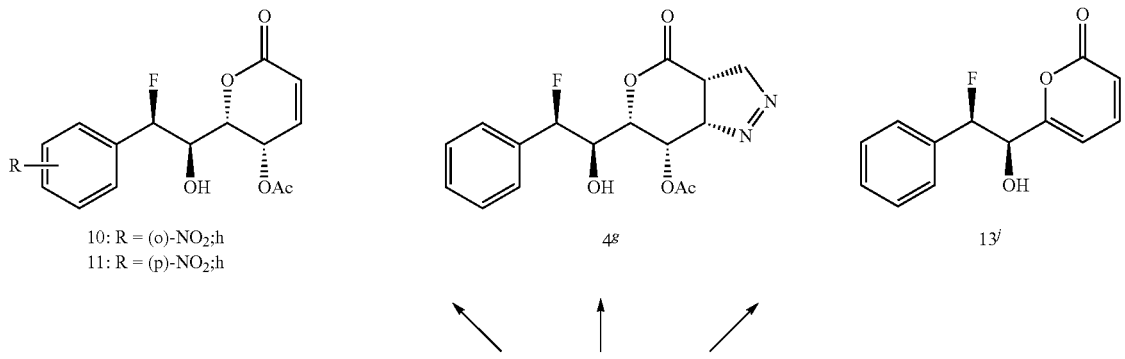

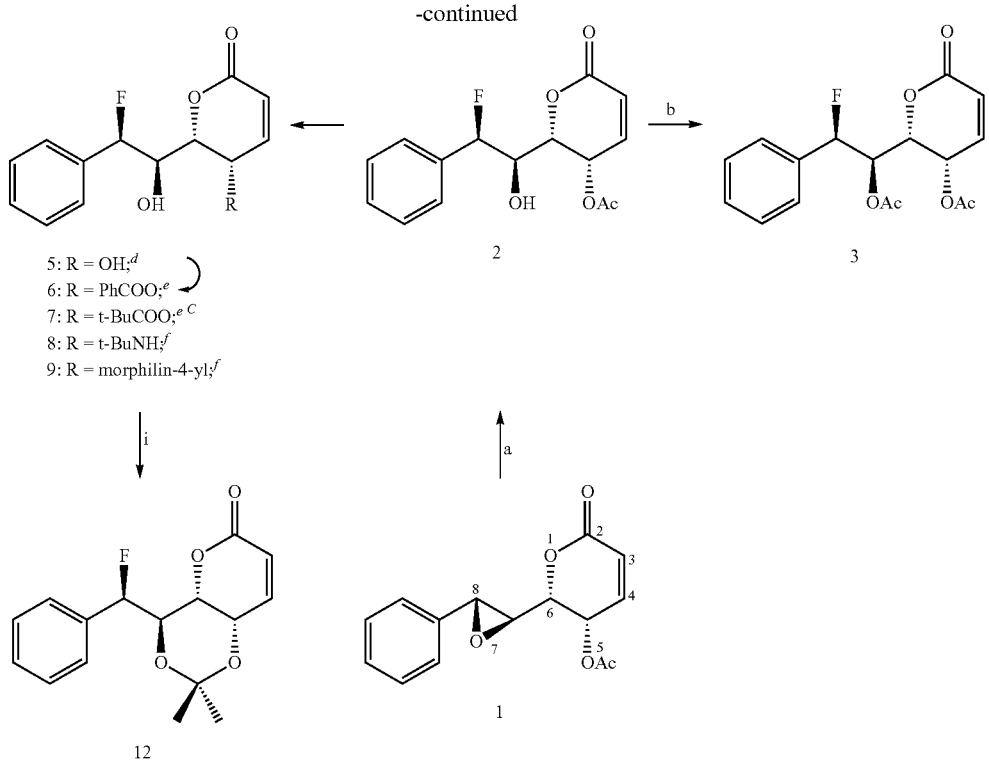

5: R = OH;[d]
6: R = PhCOO;[e]
7: R = t-BuCOO;[e,C]
8: R = t-BuNH;[f]
9: R = morphilin-4-yl;[f]

a) BF$_3$·OEt$_2$, DCM, -78° C.; b) Ac$_2$O, DMAP, Pyridine, RT; c) CH$_2$N$_2$, Et$_2$O, 0° C.; d) Et$_3$N, MeOH, RT; e) RCOCl, Et$_3$N, DMAP, DCM, -40° C.; f) RNH$_2$, Pd(PPh$_3$)$_4$, PPh$_3$, DMF, 80° C.; g) CH$_2$N$_2$, Et$_2$O, 0° C.; h) KNO$_3$, HNO$_3$, 0° C.; i) DMP, TsOH, RT;

Using isolation product cheliensisine A as the starting material, the epoxide ring-opening product 2 was first prepared by reacting with BF$_3$OEt$_2$ in DCM (Scheme 1). The fluoride 2 was then used as the substrate for further modifications (Scheme 2). The C-7 alcohol was converted to its acetyl ester 3 by treatment of Ac$_2$O in presence of base. A [3+2] reaction of compound 2 with CH$_2$N$_2$ in ether provided the adduct 4 in moderate yield. Hydrolysis of C-5 acetoxyl group with Et$_3$N in MeOH afforded the diol 5 in good yield. Subsequently, the diol 5 was selectively esterifized with acyl chloride and Et$_3$N, giving mono-esters 6 and 7 in moderate yield. And treatment of the diol 5 with 2,2-dimethoxyl propane (DMP) in presence of TsOH furnished aceto-nylidene 12 in good yield. Tsuji-Trost reaction of the fluoride 2 with Pd(PPh$_3$)$_4$ as the catalyst and amine as the nucleaphilic reagent delivered the amines 8 and 9 in moderate yield and compound 13 as a side product. The phenyl ring of compound 2 was functionalized with KNO$_3$ in fumed HNO$_3$, giving nitro 10 and 11 in moderate yield.

Example C-2

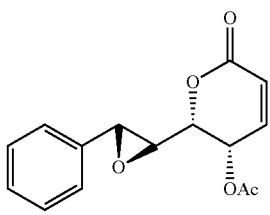

Isolation of Cheliensisin A

Cheliensisin A was isolated from ethanol extract of Announaceae plants *Goniothalamus cheliensis* Hu in Yunnan province, China.

Crushed leaves of *Goniothalamus cheliensis* Hu were leached with ethanol (100 kg). The concentrated extract was separated by silica gel column chromatography. The crude product was achieved from petroleum ether-ethyl acetate (7:3), and separated by medium pressure column chromatography. The crude product was achieved from 70% methanol-water part, and further recrystallized from chloroform to afford Cheliensisin A (300 g).

Example C-3

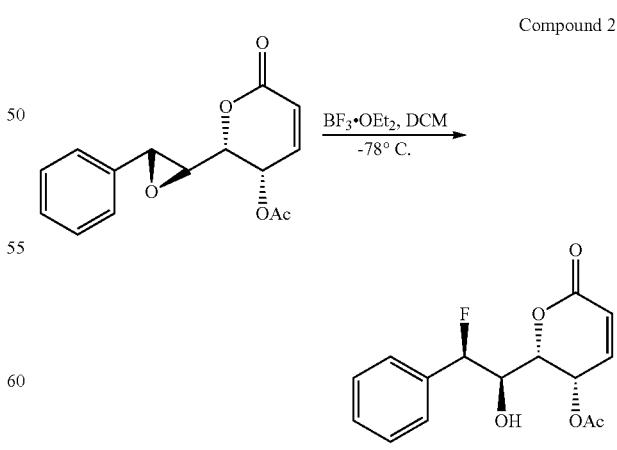

To a solution of Cheliensisin A (548 mg) in dichloromethane (12 mL) was added dropwise a solution of boron trifluoride etherate (202 μL) in dichloromethane under −78° C. nitrogen. The reaction was monitored by TLC. After the completion of the reaction (~0.5 h), a saturated aqueous sodium bicarbonate solution (6 ml) was added to quench the reaction. The mixture was extracted by dichloromethane (50 mL×3). The combined organic phase was washed with H₂O and brine, dried over anhydrous Na₂SO₄ and concentrated. The resulting crude product was chromatographed on silica gel using petroleum ether/etrol ether (1.5:1) to afford Compound 2 (312 mg, 53%).

¹H-NMR (CDCl₃, 300 MHz) δH 7.30-7.34 (m, 5H), 7.03 (dd, J=10.8 Hz, 4.5 Hz, 1H), 6.15 (d, J=10.2 Hz, 1H), 5.36 (t, J=5.4 Hz, 5.4 Hz, 1H), 4.89 (t, J=4.8 Hz, 4.8 Hz, 1H), 5.91 (d, J=45.0 Hz, 1H), 3.96 (d, J=5.4 Hz, 1H), 2.06 (s, 3H); ESI-MS (m/z) 317 [M+Na]+.

Example C-4

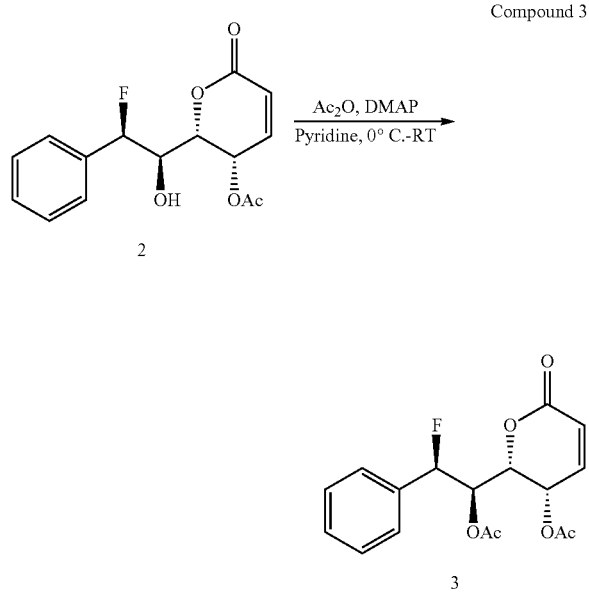

To a solution of Compound 2 (30 mg) and 4-N,N-dimethylamino-pyridine (catalytic amount) in pyridine (1 mL) was added dropwise a solution of acetic anhydride (30 μL) at 0° C. The mixture was allowed to warm up to room temperature and was stirred until the completion of the reaction (~1 h, TLC). Then the mixture was extracted by dichloromethane (50 mL×3). The combined organic phase was washed with H₂O and brine, dried over anhydrous Na₂SO₄ and concentrated. The resulting crude product was chromatographed on silica gel using petroleum ether/etrol ether (1:1) to afford pure Compound 3 (33 mg, 98%).

¹H-NMR (CDCl₃, 300 MHZ): δH 7.32-7.40 (m, 5H), 7.01 (dd, J=9.6 Hz, 6.0 Hz, 1H), 6.32 (d, J=9.6 Hz, 1H), 6.12 (d, J=45 Hz, 1H), 5.50 (dd, J=27.6 Hz, 10.2 Hz, 1H), 5.35 (dd, J=6.0 Hz, 2.7 Hz, 1H), 4.98 (dd, J=10.2 Hz, 2.4 Hz, 1H), 2.00 (s, 3H), 1.82 (s, 3H); ESI-MS (m/z) 337 [M+H]+.

Example C-5

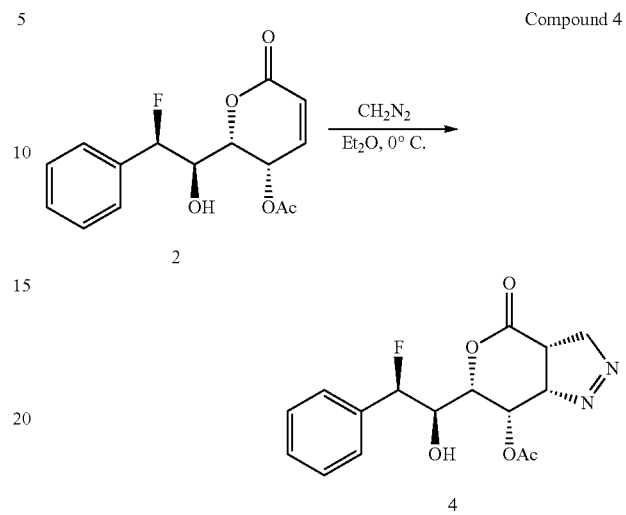

To a solution of compound 2 (30 mg) in diethyl ether (0.5 mL) was added dropwise a solution of diazomethane in ether solution (0.5 mL) under nitrogen at 0° C. After completion of reaction (~0.5 h, TLC) an appropriate amount of acetic acid was added to quench the reaction. Then the mixture was extracted by ethyl acetate. The combined organic phase was washed with saturated brine, dried over anhydrous Na₂SO₄ and concentrated. The crude product was purified by preparative Thin-layer chromatography to afford pure Compound 4 (18 mg, 53%).

¹H-NMR (300 MHz, CDCl₃): δ H 7.39-7.47 (m, 5H), 6.34 (d, J=3.6 Hz, 1H), 6.01 (d, J=45.6 Hz, 1H), 5.14 (s, 1H), 4.52 (dd, J=9.3 Hz, 2.1 Hz, 1H), 4.32 (t, J=10.5 Hz, 10.5 Hz, 1H), 4.12 (dd, J=14.1 Hz, 7.5 Hz, 1H) 3.57 (ddd, J=16.8 Hz, 9.3 Hz, 3.9 Hz, 1H), 3.24 (dd, J=17.4 Hz, 14.1 Hz, 1H), 2.12 (s, 3H), 1.25 (m, 2H); ESI-MS (m/z) 351[M+H]+.

Example C-6

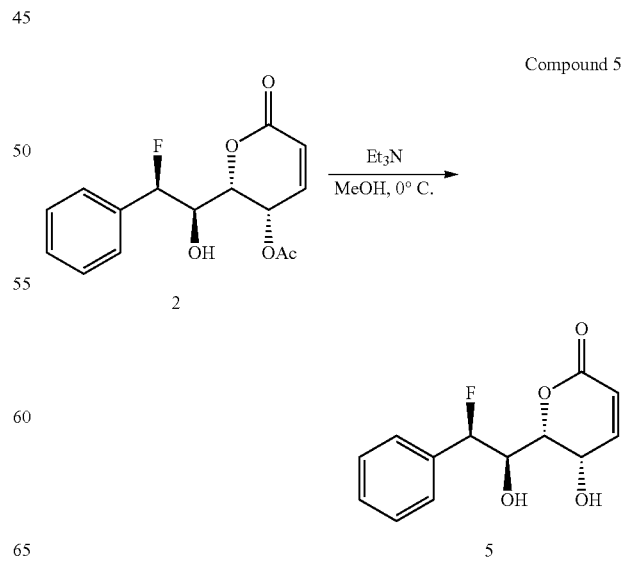

To a solution of Compound 2 (29 mg) in methanol (1 mL) was added Et₃N (12 mg) dropwise at 0° C. The reaction was monitored by TLC and was complete in 15 min. An aqueous hydrochloric acid solution (2 N, 0.1 mL) was added to quench the reaction. The mixture was then extracted with ethyl acetate (5 mL×3). The combined organic phase was washed with H₂O and brine, dried over anhydrous Na₂SO₄ and concentrated. The crude product was chromatographed on silica gel using petroleum ether/etrol ether (1:1) to afford Compound 5 as white foam (24 mg, 94%).

¹H-NMR (400 MHz, MeOD) δ 7.68 (d, J=8 Hz, 1H), 7.34-7.38 (m, 4H), 7.31 (d, J=8 Hz, 1H), 6.18 (d, J=4 Hz, 1H), 5.89 (d, J=44 Hz, 1H), 5.49 (s, 1H), 4.04 (d, J=12 Hz, 1H), 3.79 (dd, J=28 Hz, 12 Hz, 1H); ESI-MS (m/z) 253 [M+H]+.

Example C-7

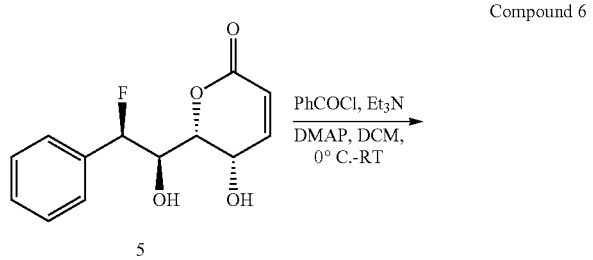

Compound 6

To a solution of compound 5 (13 mg) in dry dichloromethane (1 mL) and 4-N,N-dimethylamino-pyridine (2 mg) was treated dropwise with a solution of Et₃N (11 mg) and then with benzoyl chloride (11 mg) at 0° C. The reaction was monitored by TLC and was complete in 2 h. A saturated aqueous NaHCO₃ solution was added to quench the reaction. The mixture was then extracted with ethyl acetate (×3). The combined organic phase was washed with H₂O and brine, dried over anhydrous Na₂SO₄ and concentrated. The crude product was chromatographed on silica gel using petroleum ether/etrol ether (2:1) to afford Compound 6 (10 mg, 57%) as white foam.

¹H-NMR (400 MHz, CDCl3) δ 7.92 (d, J=8 Hz, 2H), 7.51 (t, J=8 Hz, 4 Hz, 1H), 7.28-7.38 (m, 7H), 7.16 (dd, J=12 Hz, 4 Hz, 1H), 6.28 (d, J=8 Hz, 1H), 6.02 (d, J=44 Hz, 1H), 5.70 (d, J=4 Hz, 1H), 4.81 (dd, J=8 Hz, 4 Hz, 1H), 4.06 (dd, J=24 Hz, 8 Hz, 1H); EI-MS (m/z) 356 [M]⁺.

Example C-8

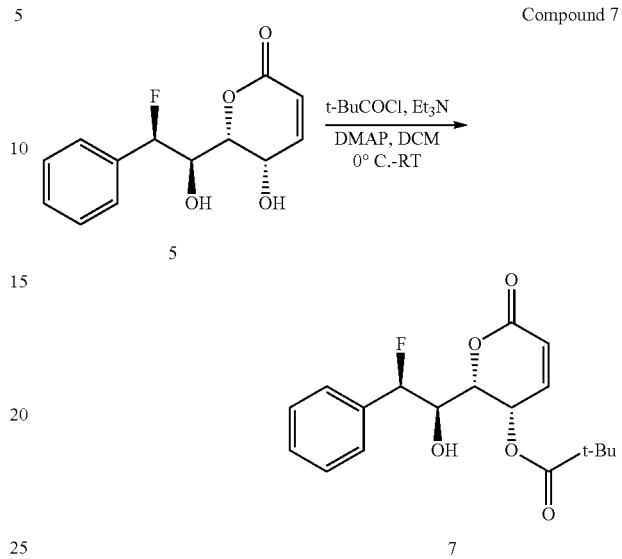

Compound 7

The compound 7 was prepared by the reaction of Compound 5 with t-Bu-COCl and following the procedure described in Example 7.

¹H-NMR (400 MHz, CDCl₃) δ 7.42 (s, 5H), 7.13 (dd, J=8 Hz, 8 Hz, 1H), 6.29 (d, J=8 Hz, 1H), 6.07 (d, J=44 Hz, 1H), 5.44 (s, 1H), 4.75 (d, J=12 Hz, 1H), 4.05 (dd, J=28 Hz, 8 Hz, 1H), 1.17 (s, 9H); EI-MS (m/z) 336 [M]⁺.

Example C-9

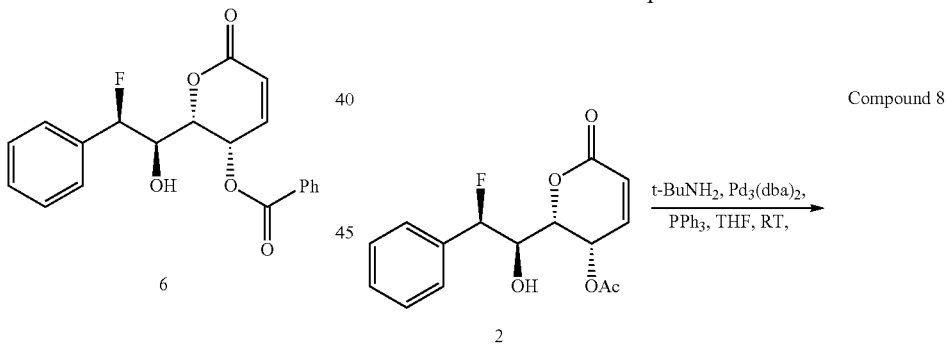

Compound 8

Tris(dibenzylidene acetone) palladium (3 mg) and triphenylphosphine (2 mg) was dissolved in tetrahydrofuran (1 mL) The mixture was stirred at room temperature for half an hour, and the solution of compound 2 (29 mg) in tetrahydrofuran (0.5 mL) was added. The mixture was then treated dropwise with t-butyl amine (17 mg). The reaction was monitored by TLC. After completion of the reaction, saturated aqueous ammonium chloride was added and the mixture was extracted several times with methylene chloride. The combined organic phases were washed with saturated sodium chloride solution, then dried over anhydrous sodium sulfate and concentrated. The crude product was chromatographed on silica gel using chloroform/methanol (30:1) to afford compound 8 (20 mg, 65%).

¹H-NMR (400 MHz, CDCl$_3$) δ 7.29-7.48 (m, 5H), 6.93 (dd, J=10.0 Hz, 5.6 Hz, 1H), 6.31 (d, J=10.0 Hz, 1H), 4.90 (d, J=3.2 Hz, 1H), 4.65 (dd, J=6.8 Hz, 5.2 Hz, 1H), 4.12 (dd, J=6.8 Hz, 3.2 Hz, 1H), 3.48 (t, J=5.2, 5.2 Hz, 1H), 2.76 (m, 2H), 2.53 (dd, J=6.0 Hz, 4.8 Hz, 2H), 2.39 (d, J=5.6 Hz, 2H), 1.92 (s, 1H), 1.56 (m, 4H); ESI-MS (m/z) 317 [M+H]$^+$.

Example C-10

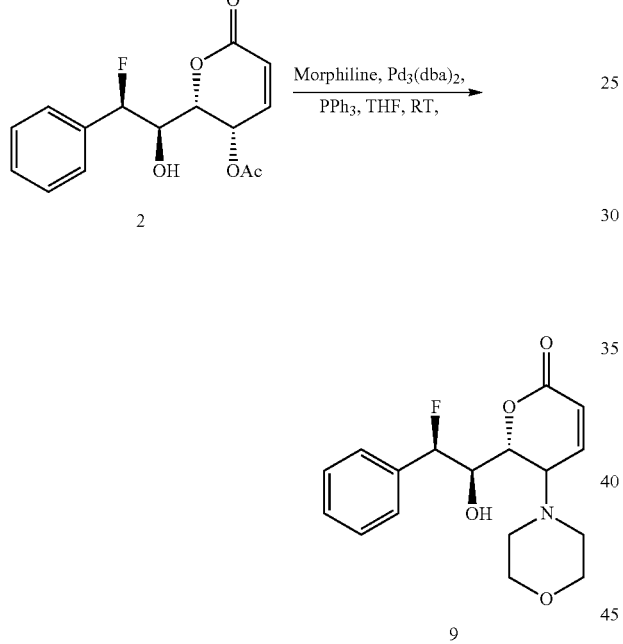

Tris(dibenzylidene acetone) palladium (3 mg) and triphenylphosphine (2 mg) was dissolved in tetrahydrofuran (1 mL) The mixture was stirred at room temperature for half an hour, and the solution of compound 2 (29 mg) in tetrahydrofuran (0.5 mL) was added. The mixture was then treated dropwise with morpholine (17 mg). The reaction was monitored by TLC. After completion of the reaction, saturated aqueous ammonium chloride was added and the mixture was extracted several times with methylene chloride. The combined organic phases were washed with saturated sodium chloride solution, then dried over anhydrous sodium sulfate and concentrated. The crude product was chromatographed on silica gel using chloroform/methanol (30:1) to afford compound 9 as a white amorphous solid (21 mg, 65%).

¹H-NMR (300 MHz, CDCl$_3$) δ 7.39-7.47 (m, 5H), 6.95 (dd, J=9.6 Hz, 5.4 Hz, 1H), 6.35 (d, J=9.9 Hz, 1H), 4.99 (d, J=1.5 Hz, 1H), 4.70 (dd, J=9.9 Hz, 4.5 Hz, 1H), 4.12 (d, J=3.9 Hz, 1H), 5.69 (t, J=4.2 Hz, 1H), 2.01 (s, 3H), 1.97 (dd, J=7.2 Hz, 1.2 Hz, 3H); ESI-MS (m/z) 322 [M+H]$^+$.

Example C-11

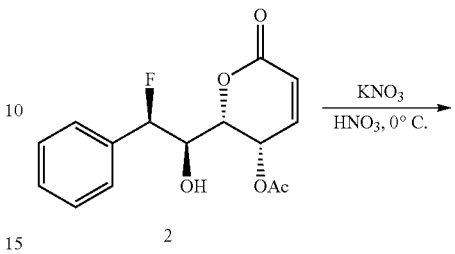

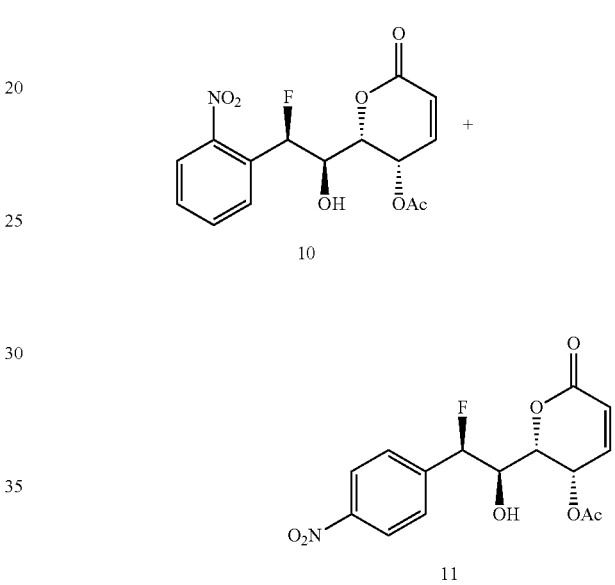

To mixed solution of nitric acid-fuming nitric acid (0.5 mL/0.5 mL) was added potassium nitrate (101 mg) under 0° C. After 15 minutes of stirring, crushed Compound 2 (29 mg) was added to the mixture. The mixture was diluted by ice water after 15 minutes reaction. The aqueous phase was extracted by ethyl acetate (×3). The combined organic phases were washed with saturated NaHCO3 solution, water and saturated sodium chloride solution, then dried over anhydrous sodium sulfate and concentrated. The crude product was chromatographed on silica gel using petroleum ether/ethyl acetate (1.5:1) to afford compound 10 (26 mg, 78%) and compound 11 (4.5 mg, 13%).

Compound 10 as white foam, ¹H-NMR (400 MHz, CDCl3) δ 8.23 (d, J=8 Hz, 2H), 7.55 (d, J=8 Hz, 2H), 7.07 (d, J=8 Hz, 4 Hz, 1H), 6.26 (d, J=12 Hz, 1H), 6.09 (d, J=48 Hz, 1H), 5.41 (d, J=4 Hz, 1H), 4.69 (d, J=12 Hz, 1H), 3.93 (ddd, J=24 Hz, 8 Hz, 4 Hz, 1H), 2.03 (s, 3H); ESI-MS (m/z): 362 [M+Na]$^+$.

Compound 11 as white foam, ¹H-NMR (400 MHz, CDCl$_3$) δ 8.14 (d, J=8 Hz, 1H), 7.84 (d, J=8 Hz, 1H), 7.73 (t, J=8 Hz, 8 Hz, 1H), 7.54 (t, J=8 Hz, 4 Hz, 1H), 7.08 (dd, J=12 Hz, 8 Hz, 1H), 6.66 (d, J=44 Hz, 1H), 6.27 (d, J=8 Hz, 1H), 5.48 (dd, J=8 Hz, 4 Hz, 1H), 4.75 (dd, J=8 Hz, 4 Hz, 1H), 4.37 (dd, J=24 Hz, 8 Hz, 1H), 2.07 (s, 3H); ESI-MS (m/z): 362 [M+Na]$^+$.

Example C-12

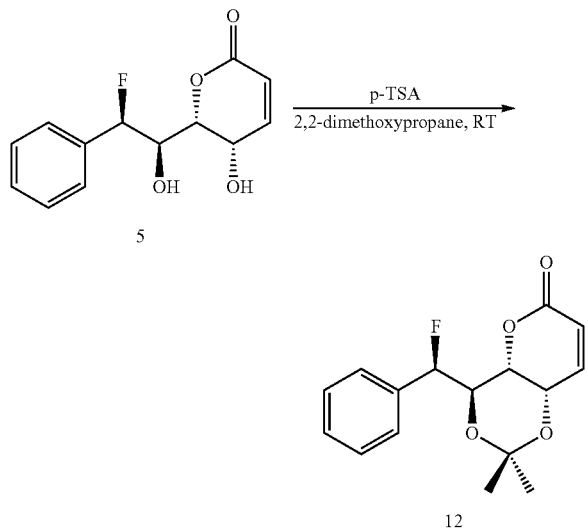

To a solution of Compound 5 (12 mg) in 2,2-dimethoxypropane (1 mL) was added p-toluenesulfonic acid (catalytic amount). The reaction was monitored by TLC. After completion of the reaction (~2 h), the solvent was distilled off under reduced pressure. The crude product was chromatographed on thin-layer chromatography using petroleum ether/ethyl acetate (2:1) to afford Compound 12 (10 mg, 68%).

Compound 12 as colorless film-like substance, $^1$H-NMR (400 MHz, CDCl$_3$) δ 7.35-7.40 (m, 5H), 6.80 (dd, J=8 Hz, 12 Hz, 1H), 6.23 (d, J=8 Hz, 1H), 5.80 (d, J=48 Hz, 1H), 4.94 (dd, J=8 Hz, 4 Hz, 1H), 4.39 (t, J=8 Hz, 4 Hz, 1H), 4.05 (dd, J=24 Hz, 8 Hz, 1H), 1.41 (s, 3H), 1.18 (s, 3H). EI-MS (m/z): 292 [M]$^+$.

Example C-13

Compound 13

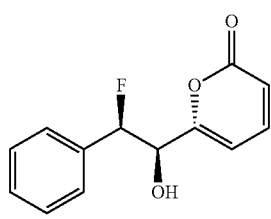

The compound is obtained as a side product during the synthesis of Compound 9.

Compound 13, colorless film, $^1$H-NMR (400 MHz, CDCl$_3$) δ 7.35-7.42 (m, 5H), 7.32 (dd, J=12 Hz, 4 Hz, 1H), 6.35 (d, J=4 Hz, 1H), 6.24 (d, J=8 Hz, 1H), 5.89 (dd, J=44 Hz, 4 Hz, 1H), 4.69 (d, J=24 Hz, 4 Hz, 1H); EI-MS (m/z) 250 [M]$^+$.

EXAMPLES

Example 1

Dual Role of p53-Regulated p21 and Bax in Apoptotic Induction by Compounds of the Invention The tumor suppressor p53 plays a key role in negative regulation of cellular growth upon treatment of chemotherapeutics agents. To further explore the role of p53 signaling and elucidate the molecular mechanism, the inventors employed colon cancer HCT116 cell line and its derivatives in which a specific transcriptional target of p53 is knocked down by homologous recombination. Treatment with a representative compound of the invention, Compound F2, resulted in inhibited anchorage-independent growth and a cell apoptotic response, and led to induction of p53, p21 and Bax in HCT116 cells. Induction of Bax by Compound F2 was essential for Compound F2-induced apoptosis, for Compound F2-induced anchorage-independent growth inhibition and apoptosis was dramatically impaired in Bax knockout (Bax−/−) HCT116 cells. In contrast, treatment of HCT116 p21−/− cells with Compound F2 resulted in enhanced sensitivity to Compound F2-induced anchorage-independent growth inhibition and apoptosis. Taken together, the inventors' results present a novel concept wherein p21 induced by p53-dependent transcription protects cells from, otherwise, in its absence, apoptosis which is mediated by p53-dependent activation of pro-apoptotic protein Bax. p21 thus can be used as a molecular switch for therapeutic intervention of colon cancer.

As discussed above, most chemotherapeutic agents induce cell death through activation of the p53 pathway. In response to various cellular stresses, p53 regulates a variety of cellular functions including cell cycle progression, apoptosis, senescence, cell motility, DNA repair, genetic instability and cell metabolism by transcriptionally activating a variety of cellular genes (1.4-1.7). Significantly, there is evidence from cell, animal and clinical studies that p53 is associated with cancer cell or patient sensitivity in response to various anti-cancer agents (1.8-1.10). In colorectal cancer cells, p53 disruption rendered cells resistant to the antimetabolite 5-FU but sensitized these cells to the DNA damaging drug doxorubicin (1.11). Therefore the role of p53 in mediating anti-cancer response is complex and depends on both cellular context and class of chemotherapeutics. However, the molecular mechanism underlying this distinct role of p53 in the response of different tumor cell types to various drug groups is not fully understood.

p21 is a member of the Cip/Kip family inhibitors of cell cycle progression that associates with the cyclin/CDK complexes leading to the inhibition of CDK activities and DNA replication (1.12). p21 is a p53 target gene and it is a relevant mediator of p53-induced cell cycle arrest in response to DNA damaging agents and/or oncogenic stress (1.12, 1.13). Other studies have shown that p21 has additional functions as a differentiation inducer (1.14, 1.15) and as an inhibitor of apoptosis induced by DNA-damaging agents (1.16). It was reported that p21 performed anti-apoptosis role through binding and inhibiting the main effector caspase, caspase 3 (1.17). However, cell death induced by caffeine on irradiated MCF7 breast cancer cells that do not express caspases 3, was linked to a decrease of the expression of p21 and, consistently, was counteracted by overexpressed p21 (1.18). Therefore, the antiapoptotic function of p21 may not only involve its capacity to inhibit the caspase 3 and may act more upstream in the apoptotic machinery.

The Bcl-2 family of interacting proteins acts as major regulators of the mitochondrial apoptotic pathway, representing an integrating node towards which converge numerous death and survival signals in mammalian cells (1.19). Anti-apoptotic Bcl-2 homologues preserve mitochondrial integrity by opposing the activity of multi-domain pro-apoptotic Bcl-2 family members Bax and Bak, and that of their upstream effectors, the BH3-only proteins (e.g. Bim, Puma, Bad . . . ). This occurs essentially by physical interactions between anti- and pro-apoptotic members that involve engagement of the BH3 domain of the latter by a hydrophobic pocket formed at the surface of the former. These physical interactions play a key role in maintaining cell survival. More specifically, mechanistic investigations revealed that the interactions required to maintain survival are these that the anti-apoptotic proteins (such as Bcl-2 and Bcl-xL) engage with "activator" BH3-only proteins (such as Puma or Bim, which can directly activate Bax) and with multi-domain proteins themselves (such as Bax) (1.20, 1.21). It should be noted that induction of Puma upon DNA damage does not trigger apoptosis unless p21 expression is abolished, indicating that p21 can interfere with cell death via affecting downstream of Puma (1.22).

In this Example, the inventors investigated the role played by p53 and two of its target proteins, p21 and Bax in cell death induced by Compound F2, a newly discovered anti-cancer agent. Our results indicated that Compound F2 treatment induced p53-dependent transcription of Bax, which played important role in Compound F2-induced cancer cell apoptosis. The results also showed that p21, induced through p53-dependent transcription, exerted anti-apoptosis function in Compound F2-treated cells. In the absence of p21 these cells switch to apoptosis. Thus, p53 has a dual role in therapeutic intervention of colon cancer by Compound F2.

Plasmids, Antibodies, and Reagents.

The antibodies specific against PARP, caspase-3, cleaved caspases-3 were purchased from Cell Signaling Technology Inc (Beverly, Mass.). The antibody specific against p53 was bought from Santa Cruz Biotechnology (Santa Cruz, Calif.). The antibodies against Bax and p21 were purchased from Upstate Biotechnology (Lake Placid, N.Y.). Antibody against β-actin was from Sigma (St. Louis, Mo.).

The Compound F2 was prepared according the methods of invention. Compound F2 was dissolved in dimethyl sulfoxide (DMSO, Santa Cruz Biotechnology) to make a stock concentration at 16 mM and further diluted in McCoy's 5A medium with final DMSO concentration at 0.2% (v/v) for cell culture experiments. The same amount of DMSO was used as a vehicle control in all experiments.

Cell Culture and Transfection.

Human colon cancer cell line HCT116 and its p53-deficient (HCT116-p53$^{-/-}$), Bax-deficient (HCT116-Bax$^{-/-}$), p21-deficient (HCT116-p21$^{-/-}$) derivative was kindly provided by Dr. Bert Vogelstein (Johns Hopkins University Medical Institutions, Baltimore, Md.)(1.23). HCT116 cells were maintained at 37° C. in a 5% CO2 incubator in McCoy's 5A medium supplemented with 10% fetal bovine serum (FBS). Stable transfections were performed with specific cDNA constructs using PolyJet™ DNA In Vitro Transfection Reagent (SignaGen Laboratories, Gaithersburg, Md.) according to the manufacturer's instructions. For stable transfection selection, cultures were subjected to blasticidin selection for 4-6 weeks, and surviving cells were pooled as stable mass transfectants as described in our previous study (1.24).

Anchorage-Independent Growth Assay.

Anchorage-independent growth (soft agar assay) in soft agar was carried out as described in inventors' previous studies (1.25). Briefly, $1 \times 10^4$ cells mixed with various concentration of Compound X in 10% FBS BME containing 0.33% soft agar, was seeded over bottom layer of 0.5% agar in 10% FBS BME in each well of 6-well plates. The plates were incubated in 5% $CO_2$ incubator at 37° C. for 3 weeks, and the colonies with more than 32 cells of each were scored and presented as colonies/$1 \times 10^4$ cells. The data as collected is shown in FIGS. 1A-1B.

Flow Cytometry Assay.

Flow cytometry assay was assessed as previously described in reference (1.26). After the time periods indicated, the Compound X-treated and control cells were harvested and fixed in 75% ethanol. The fixed cells were stained in the buffer containing 0.1% Triton X-100, 0.2 mg/ml RNase A, and 50 µg/ml PI (propidium iodide) at 4° C. for 1 hour and were then examined by flow cytometry utilizing an Epics XL FACS (Beckman Coulter Inc., Miami, Fla.) and EXPO 32 software as described previously (1.26).

Western Blotting.

Cellular protein extracts were prepared with cell lysis buffer (10 mM Tris-HCl, pH 7.4, 1% SDS, 1 mM $Na_3VO_4$) and resolved by SDS-PAGE. The membranes were probed with the indicated primary antibodies and HRP-conjugated secondary antibody. Signals were detected with the ECL western-blotting system as described in our previous reports (1.27, 1.28).

RT-PCR.

Total RNA was extracted with Trizol reagent (Gibco) and cDNAs were synthesized with the ThermoScript™RT-PCR system (Invitrogen, Carlsbad, Calif.). To detect Bax induction, a pair of oligonucleotides (5'-AGC TGC AGA GGA TGA TTG CC-3' and 5'-TGG TTC TGA TCA GTT CCG GC-3') was synthesized and used as the specific primers to amplify human Bax cDNA. For p21 induction, a pair of oligonucleotides (5'-ATG TCC GTC AGA ACC CAT GC-3' and 5'-GAG AAG ATC AGC CGG CGT TT-3') was synthesized and used as the specific primers to amplify human p21 cDNA. Human β-actin cDNA was amplified by the primers 5'-GTG CTA TCC CTG TAC GCC TC-3' and 5'-CCA GGA AGG AAG GCT GGA AG-3'.

Statistical Methods.

All data are presented as mean values±standard deviation (SD) of three independent experiments. Comparison of the effects of various treatments was performed using factor analysis, one-way ANOVA analysis of variance and a two-tailed t-test. Difference with a p value of <0.05 was considered statistically significant.

Results

Compound F2 Efficiently Blocked Anchorage-Independent Growth and Induced Cell Apoptosis.

To clarify the potential application of Compound F2 in the treatment of human colon cancer, the inventors first examined the inhibition of anchorage-independent growth of human colon cancer cell treated with this compound. As in FIGS. 1A and B, incubation of Compound F2 with HCT116 cells in soft agar for 2 weeks exhibited significantly restrained the size and number of colonies when compared with the vehicle (DMSO, 0.2%)—treated cells. To elucidate the molecular mechanisms of Compound F2 inhibiting anchorage-independent growth, the inventors applied propidium iodide (PI)-staining flow cytometry for measuring apoptosis and cell cycle transition, which were showed underlying anchorage-independent growth (1.29). HCT116 cells were treated either with DMSO (0.2%), 16 µM or 32 µM Compound F2 for 48 h and results revealed a substantial increase in sub-G1 DNA content (apoptotic peak) compared with cells treated with vehicle control (FIG. 1C). Next, the inventors analyzed the Compound F2-induced apoptotic cell death by examining the expression of caspase-3 and PARP (poly (ADP-ribose) polymerase) after treatment with Compound F2. When cells were treated with 16 µM Compound F2, as expected, cleaved caspases-3 and PARP were detected in a time-dependent manner from 24 h to 48 h (FIG. 1D). These results confirmed reproducible apoptotic effects of Compound F2 on different human colon cancer cell lines, and indicated that the apoptosis inducing effect was mediated by activation of caspases-3.

Compound F2 Induced p53-Dependent Bax and p21 Accumulation

Having established that Compound F2 could induce the apoptosis in colon cancer cells, the inventors next focused on the molecular mechanisms of apoptosis induced by Compound F2 and tested several important apoptosis-related proteins. The inventors cultured HCT116 colon cancer cells in the presence of 16 µM Compound F2 and then examined protein levels at different time point. FIG. 2A showed that Compound F2 treatment caused p53 and its downstream target p21 and Bax increasing as time-dependent manner. Since p21 and Bax can be induced through both of p53-dependent and p53-independent pathways (1.30, 1.31), the inventors next investigated whether p21 and Bax is p53-dependent. The induction of p21 and Bax by Compound F2 in HCT116 WT cells was blocked in p53−/− HCT116 cell (FIG. 2D). These results showed that Compound F2-induced p21 and Bax accumulations are via p53-dependent axis.

p53 and its Downstream Gene p21 and Bax, Played Different Role in Compound F2-Induced Cell Apoptosis To further assess the role of p53, p21 and Bax in Compound F2-induced apoptosis, the inventors used HCT116 cells with either of these genes deleted by homologous recombination (1.23). When treated with Compound F2, Bax−/− cells were completely refractory to apoptosis (1.00% vs. 18.30% when treated with 16 µM Compound F2, and 0.69% vs. 26.27% when treated with 32 µM Compound F2, FIGS. 2B and 2C). In contrast, p53−/− cells were still able to undergo marked apoptosis, identical to parental HCT116 cells (7.41% vs. 18.30% when treated with 16 µM Compound F2, and 14.18% vs. 26.27% when treated with 32 µM Compound F2, FIGS. 2B and 2C). These results indicated that loss of Bax confers resistance of HCT116 cells to apoptosis induced by Compound F2, but loss of p53 with much less this effect. In the term of another p53 downstream target p21, the result showed that p21−/− HCT116 cells were more sensitive than wild type cells when treated with Compound F2 (80.31% vs. 26.27% when treated with 32 µM Compound F2, in FIG. 2C).

To determine whether Bax is required for Compound F2-induced apoptosis, Bax knockout HCT116 cells were treated with 16 µM Compound F2 and subjected to Western Blot. As expected, Compound F2 treatment induced caspases 3 and PARP cleavage in wild type (WT) but not Bax-deficient cells (FIG. 2E). Taken together, these results showed that p53 functions upstream of p21 and Bax, which controlled Compound F2-induced apoptosis diversely.

Bax, Upregulated Through p53-Dependent Transcription, Played a Positive Role in Compound F2-Induced Cell Apoptosis It is well accepted that Bax can be induced in response to a wide variety of stress (1.32). Considering Bax expression being regulated through different levels (1.33), the inventors evaluated Bax mRNA levels induced by Compound F2 between HCT116 WT and p53−/− cells. Bax mRNA expression was profoundly upregulated by Compound F2 treatment in HCT116 WT cells, but this induction was blocked by p53 deficiency (FIG. 3A). The inventors' results demonstrated that Bax accumulation in HCT116 cells after Compound F2 treatment was through p53-dependent manner. As expected, Bax deficiency had no role in p53 and p21 induction (FIG. 3B). To determine the effect of Bax deficiency on inhibited cancer cell growth induced by Compound F2, the inventors also performed anchorage-independent cell growth assay with HCT116 Bax−/− cells and the result showed that Compound F2 treatment only partially inhibit colony formation in HCT116 Bax−/− cells (FIG. 3C). Collectively, these results show that Bax induction dependent on p53 play an important role in Compound F2-induced apoptosis and inhibited cancer cell growth in colon cancer cells.

P21, Also Upregulated Through p53-Dependent Transcription, Protected Cells Against in Compound F2-Induced Cell Apoptosis In human colon cancer HCT116 cells, Bax induction by Compound F2 was through p53-dependent transcription (FIG. 3A), and Compound F2-induced apoptosis was through Bax-mediated mitochondrial pathway (FIG. 2E). In contrast, p21 deficiency cells were more sensitive to Compound F2 (FIG. 2F). To further assess the role of p53 and p21 in Compound F2-induced apoptosis, the inventors evaluated p21 mRNA levels induced by Compound F2 between HCT116 WT and p53−/− cells. Under the treatment with Compound F2, p21 mRNA expression increased in time-course manner in HCT116 WT cells, but this induction was blocked by p53 deficiency (FIG. 4A). Therefore, p21 induction in HCT116 cells after Compound F2 treatment was through p53-dependent manner.

p21 expression has been shown to be regulated largely at the transcriptional level by both p53-dependent and -independent mechanisms (1.34). The p21 promoter contains two conserved p53-binding sites, and at least one of these is required for p53 responsiveness after DNA damage (1.35). Inventors' study showed that p53 binding site in p21 promoter played a essential role in mediating Compound F2-induced p21 expression (FIG. 4C).

Discussion

With the accumulating exploration of molecular mechanisms of plant natural compound activity, they have been widely used as candidate anti-tumor agents (1.36). The tumor suppressor p53 has a central role in plant natural compound's therapeutic modality (1.36). This protein facilitates favorable antitumor drug response through a variety of key cellular functions, including cell cycle arrest, senescence, and apoptosis. In cancer cells, p53 functions as a double-edged sword, inducing cell death by initiating apoptosis in response to some stimuli or when overexpressed and protects cells by inducing transient, reversible growth arrest in response to other stimuli (1.37-1.40). The inventors have showed that in wild-type p53 HCT116 cells, Compound F2 induced p53 up-regulation and thus induced both the pro-apoptotic protein Bax and check-point protein p21. Bax plays an essential role in the apoptotic response to Compound F2 in human cancer cells. In contrast, genetic ablation of p21 makes these cells sensitive to Compound F2-induced apoptosis. Thus, p53 has a dual role in therapeutic intervention of colon cancer by Compound F2.

Disruption of either p53 or any of the components that form the so called, "p53-network" is a key event in the etiology and development of virtually all human cancers (1.41). p53 behaves as a signaling node that is activated by a plethora of stress signals and it in turn participates in the orchestration of various cellular responses including, but not restricted to, cell-cycle arrest, senescence, apoptosis, and autophagy (1.7). The inventors' previous studies demonstrated that p53 has a suppressive activity on the cell signaling pathways leading to the activation of AP-1 and NFκB through upregulated PTEN expression responding to UV radiation (1.42). These responses have been implicated in an individual's ability to suppress tumor formation and to respond to many types of cancer therapy (1.43). Following cellular stresses, p53 is stabilized and binds to DNA that results in the transcriptional regulation of p53-regulated genes that are involved in mediating key cellular processes (1.44). As observed for other master transcriptional regulators of cell behavior, the cellular response to p53 activation varies greatly with the context. Stimulus- and cell type-specific p53 responses have been extensively documented (1.45). In inventors' paradigm, p53 was upregulated by anti-cancer agent Compound F2 treatment, and resulted in Bax and p21 induction (FIG. 2D). This asymmetrical activation of p53's downstream target genes occasionally had a pivotal role in the cellular response to DNA damage, which was necessary to clarify the role of p53 in anti-cancer therapy (1.46, 1.47).

Regulation of Bax activity is a critical event in apoptosis. Bax mediates permeabilization of the outer mitochondrial membrane for release of pro-apoptotic molecules such as cytochrome C and Smac/Diabiol (1.48). Once in the cytoplasm, cytochrome c functions as a cofactor with Apaf-1 to promote the cleavage of pro-caspase-9, initiating apoptosis (1.48). Two homologues, Bcl-2 and Bcl-xL, antagonize Bax function by heterodimerizing with it in the mitochondria, blocking the release of cytochrome C (1.49). Regulation of Bax protein expression, therefore, is a key factor in this process. In this regard, the inventors' results demonstrated that treatment of HCT116 cells with F2 could upregulate Bax expression (FIG. 2A), and Bax induction appeared to play an essential role in Compound F2-induced apoptosis, because Bax-deficient HCT116 cells underwent primarily apoptosis-resistant response (FIGS. 2B & C) and reduced Compound F2-inhibited anchorage-independent growth (FIG. 3C). The inventors' results also demonstrated that Compound F2-induced Bax upregulation was at mRNA level (FIG. 3A), which was interrelated with p53 status (FIG. 2D).

Besides Bax, p21 is another well-known target gene regulated by p53 at transcriptional level, which is responsible for initiating/G0G1 arrest by binding and inhibiting cyclin-dependent kinases activity (1.50). In addition to growth inhibiting functions, p21 can induce apoptosis (1.12). On one hand, the function of p21 to inhibit cell proliferation may contribute to its ability to act as tumor suppressor. On the other hand, the capacity of p21 to induce cell cycle arrest after stress can protect cells from stress-induced apoptosis (1.12). The mechanisms by which p21 can prevent cells from undergoing apoptosis are not well understood. One mechanism is assumed to involve p21-dependent cell cycle arrest that would permit repair or prevent DNA Damage. The inventors have shown here that HCT116 p21−/− cells sufficed to sensitize to Compound F2-induced cell apoptosis (FIGS. 2B & F). It was reported that p21 could be induced by DNA damage, dependently or independently of p53 (1.51, 1.52), not only at a transcriptional but also at a post-transcriptional level (1.51). In inventors' paradigm, p21 induction by Compound F2 was transcriptional (FIG. 4A) and p53-dependent (FIG. 2D and FIGS. 4A & C).

In summary, the present study disclosed that Compound F2 (a representative compound of the invention) treatment induced p53-dependent Bax which plays a critical role in drug-induced apoptosis of colon cancer cells. Genetic evidence implicates an important role of Bax in Compound F2-induced apoptosis where another target protein of p53, p21 was a protective factor from colon cancer cells from Compound F2-induced apoptosis. Therefore, p53 played a dual role in therapeutic intervention of Compound F2 in cancer, and modulation of p21 could be exploited as an effective strategy for colon cancer therapeutics by Compound F2.

Example 2

Apoptotic Induction Via p53-Independent PUMA Expression by Compounds of the Invention The inventors have demonstrated that Compound F2 (a representative compound of the invention) inhibited cancer cell anchorage-independent growth by inducing apoptosis via p53-independent PUMA induction. Deficiency in PUMA abrogated Compound F2-induced apoptosis, and rendered a cancer cell anchorage-independent growth in a Compound F2 resistance manner. Further studies indicated that PUMA induction by Compound F2 was regulated by FoxO3a at transcriptional level, followed by Akt inhibition. The results also showed that superoxide generation induced by Compound F2 plays a role in Compound F2-induced PHLPP1/AKT/FoxO3a cascade activation, PUMA upregulation and apoptosis induction. Furthermore, knocking down PHLPP1 with shRNA in HCT116 wild type cells suppressed the antitumor effects Compound F2. These results suggested that PUMA-mediated apoptosis is pivotal for the anticancer activities of Compound F2, and PHLPP1/AKT/FoxO3a axis contributed to Compound F2-induced PUMA expression. These data indicated that the novel compounds of the invention can be potent antitumor agents that induce cell apoptosis and have therapeutic potential for colon cancer.

As discussed above, the most prevalent reported genetic defect observed in human malignancies, including colon cancer, is the loss or inactivation of the tumor suppressor protein p53 (2.4). It is implied that inactivation or loss of p53 is an important step in the development of colon cancer. Numerous studies have demonstrated that in response to DNA damage, p53 is stabilized and induces the expression of a plethora of genes involved in cell cycle control, DNA repair, and apoptosis (2.5). PUMA, p53-upregulated modulator of apoptosis, is a BH3-only Bcl-2 family member and a potent inducer of apoptosis. Transcription of PUMA is activated by p53 in response to DNA-damaging agents such as γ-irradiation and common chemotherapeutic drugs (2.6). PUMA binds to all five antiapoptotic Bcl-2 family members, such as Bcl-2 and Bcl-XL, which relieves their inhibition of Bax and Bak, leading to mitochondrial membrane permeabilization, and subsequently caspase cascade activation (2.6). Nevertheless, p53-dependent regulation of PUMA is dysfunctional in most cancer cells due to p53 abnormalities, causing survival of tumor cells and therapeutic resistance. PUMA also mediates p53-independent apoptosis induced by a variety of nongenotoxic stimuli, such as tumor necrosis factor-α (2.7), serum starvation (2.8), cytokine withdrawal (2.9), STS (2.10, 2.11), glucocorticoids (2.10, 2.12), and ischemia/reperfusion (2.13). Several transcription factors, including p65, p73, and Forkhead box O3a (FoxO3a), have been implicated in p53-independent PUMA induction.

The inventors have determined that whether Compound F2-induced cytotoxicity in human colon cancer cells required p53 function. The results indicate that, despite p53 upregulation, Compound F2-induced apoptosis in different colon cancer cells was independent of p53 status. Furthermore, this study demonstrates that Compound F2-induced PUMA is pivotal for the anticancer effects of Compound F2. The effect of Compound F2 on PHLPP1/AKT/FoxO3a pathway and related PUMA accumulation are also described. Therapeutic application of Compound F2 is therefore predicted to be effective against colon cancers regardless of p53 status.

Plasmids, Antibodies, and Reagents.

The human PUMA promoter-driven luciferase reporters were kindly provided by Dr. Lin Zhang (University of Pittsburgh School of Medicine, Pittsburgh, Pa.) (2.14). pLKO.1-PHLPP1 shRNA plasmids was kindly gift from Dr. Tianyan Gao (University of Kentucky, Lexington, Ky.) (2.15). The antibodies specific against PARP, caspase-3, cleaved caspases-3, Bcl-2, Bcl-x1, p-foxO3a (Ser253), foxO3a, p-AKT (Thr308), p-AKT (Ser473), AKT, PTEN and GFP were purchased from Cell Signaling Technology Inc (Beverly, Mass.). The antibodies specific against p53 and Bid were bought from Santa Cruz Biotechnology (Santa Cruz, Calif.). The antibodies against Bax were purchased from Upstate Biotechnology (Lake Placid, N.Y.). Antibodies against PHLPP1 and PHLPP2 were obtained from Bethyl (Montgomery, Tex.). Antibodies against PUMA and β-actin were from Sigma (St. Louis, Mo.). Dichlorofluorescein diacetate (DCFH-DA) and hydroethidine (HE) were purchased from Invitrogen (Carlsbad, Calif., USA).

Compound F2 was prepared according the methods of invention. Compound F2 was dissolved in Dimethyl sulfoxide (DMSO, Santa Cruz Biotechnology) to make a stock concentration at 16 mM and further diluted in McCoy's 5A medium with final DMSO concentration at 0.2% (v/v) for cell culture experiments. The same amount of DMSO was used as a vehicle control in all experiments.

Cell Culture and Transfection.

Human colon cancer cell line HCT116 and its PUMA-deficient (HCT116-PUMA$^{-/-}$), p53$^{-/-}$-deficient (HCT116-p53$^{-/-}$) derivative was kindly provided by Dr. Bert Vogelstein (Johns Hopkins University Medical Institutions, Baltimore, Md.) (2.16), and HT-29 and DLD-1 colon cancer cell lines were gift from Dr. Chinthalapally V. Rao (University of Oklahoma Health Sciences Center, Oklahoma City, Ohio) (2.17). HCT116 and HT29 were maintained at 37° C. in a 5% CO2 incubator in McCoy's 5A medium supplemented with 10% fetal bovine serum (FBS). DLD-1 cell was cultured in RPMI-1640 medium supplemented with 10% FBS. Stable transfections were performed with specific cDNA constructs using PolyJet™ DNA In Vitro Transfection Reagent (SignaGen Laboratories, Gaithersburg, Md.) according to the manufacturer's instructions. For stable transfection selection, cultures were subjected to blasticidin selection for 4-6 weeks, and surviving cells were pooled as stable mass transfectants.

Anchorage-Independent Growth Assay.

Anchorage-independent growth (soft agar assay) in soft agar was carried out as described in Example 1.

Flow Cytometry Assay.

Flow cytometry assay was carried out as described in Example 1.

Western Blotting.

See Example 1 for the method.

RT-PCR.

See Example 1 for the description.

Luciferase Reporter Assay.

HCT116 cells stably expressing the luciferase reporter constructs were seeded into 96-well plates ($5\times10^3$/well) and subjected to compound treatment when the cultures reached 80~90% confluence. Cellular lysates were prepared at the indicated time points, and the luciferase activities were determined by a luminometer (Wallac 1420 Victor 2 multi-label counter system) as described in our previous studies (2.24, 2.25). The results are expressed as a relative activity that is normalized to the control cells without treatment.

Statistical Methods.

See Example 1 for the description.

Results

Compound F2 (a Representative Compound of the Invention) Efficiently Blocked Anchorage-Independent Growth of p53-Wildtype and p53-Mutant Colon Cancer Cells To clarify the potential application of Compound F2 in the treatment of human colon cancer, the inventors first examined the inhibition of anchorage-independent growth of human colon cancer cell treated with this compound. Anchorage-independent growth ability is an in vitro indicator and a key characteristic of the transformed cell phenotype (2.26). As in FIG. 5B, incubation of Compound F2 with HCT116 cells in soft agar for 2 weeks exhibited significantly decreased anchorage-independent growth when compared with the vehicle (DMSO, 0.2%)—treated cells. It was noted that the size and the number of colonies in the Compound F2 (16 and 32 μM, respectively)—treated cells were restrained markedly (FIG. 5B). Results of the inhibition effects of this compound were shown in FIG. 5C for HCT116, HT-29 and DLD-1 colon cancer cells. These data showed that Compound F2 does have an inhibitory activity on human colon cancer growth.

Compound F2 Efficiently Induces Apoptosis in Different Human Colon Cancer Cells

To elucidate the molecular mechanisms of Compound F2 inhibiting anchorage-independent growth, the inventors applied propidium iodide (PI)-staining flow cytometry for measuring apoptosis and cell cycle transition, which were showed underlying anchorage-independent growth (2.27). As in FIG. 6A, HCT116, HT-29 and DLD-1 cells were treated either with DMSO (0.2%), 16 μM or 32 μM Compound F2 for 48 hours. Cells were harvested, ethanol fixed, stained with propidium iodide (PI) and analyzed by flow cytometry. Results revealed a substantial increase in sub-G1 DNA content (apoptotic peak) compared with cells treated with vehicle control in three colon cancer cells (FIG. 6A). Next, the inventors analyzed the Compound F2-induced apoptotic cell death by examining the cleaved caspase-3 (effecter caspase) and PARP (substrate of caspase-3, poly (ADP-ribose) polymerase) after treatment with Compound F2. When cells were treated with 16 μM Compound F2, as expected, cleaved caspases-3 and PARP were detected in a time-dependent manner from 6 hours to 48 hours in three different colon cancer cells (FIG. 6B). These results confirmed reproducible apoptotic effects of Compound F2 on different human colon cancer cell lines, and indicated that the apoptosis inducing effect by Compound F2.

PUMA Induction was Essential for Compound F2-Induced Apoptosis and Anchorage-Independent Growth Inhibition in Colon Cancer Cells Having established that Compound F2 could induce the apoptosis in colon cancer cells, the inventors next focused on the molecular mechanisms of apoptosis induced by Compound F2 and tested several important apoptosis-related proteins. The inventors cultured HCT116, HT-29 and DLD-1 colon cancer cells in the presence of 16 μM Compound F2 for 48 h and then examined protein levels in cell lysates. FIG. 7A shows that Compound F2 treatment caused p53 accumulation and increased expression of the pro-apoptotic protein PUMA.

Considering that HCT116 cells express a wild-type p53, the inventors tested whether the induction of cell death by Compound F2 in HCT116 cells was through a p53- or PUMA-dependent pathway. To address this possibility, HCT116 cells with a p53 deficiency (HCT116 p53−/−) were employed. As indicated by flow cytometry analysis, the deletion of p53 protein expression in HCT116 (HCT116 p53−/−) cells only partially inhibited Compound F2-induced apoptosis as compared to that in HCT116 wild type (WT) (FIG. 7B), whereas deficient of PUMA in HCT116 (HCT116 PUMA−/−) cells resulted in over 90% inhibition of cell apoptosis following 16 µM Compound F2 treatment under the same treatment conditions (FIG. 7B). The induction of the cleavage of caspase 3 and PARP was also detected in HCT116 cells but not in HCT116 PUMA−/− cells (FIG. 7C). The result of anchorage-independent cancer cell growth showed that PUMA-deficient cells were significantly more resistant to Compound F2 than wild type cells in a long-term colony formation assay (FIG. 7D). Collectively, these results show that PUMA is essential for Compound F2 induced apoptosis in colon cancer cells.

PUMA is Induced by Compound F2 at Transcription Level in a foxO3a-Dependent, p53-Independent Manner PUMA is a mitochondrial protein, which could mediate apoptosis through either p53-dependent or -independent mechanisms based on various experimental systems (2.28). The requirement for PUMA in Compound F2-induced cancer cell apoptosis and anchorage-independent growth inhibition promoted us to investigate whether PUMA induction is in p53-dependent manner. PUMA was found to be induced by Compound F2 within 12 hours, with increasing as time-dependent manner, in both WT and p53−/− HCT116 cells at similar levels (FIG. 8A). Furthermore, Compound F2 treatment resulted in PUMA induction in HT-29 and DLD-1, two p53-mutant colon cancer cells (FIG. 8B). These results indicated PUMA induction was via p53-independent manner.

To study the mechanism of p53-independent regulation of PUMA, the inventors analyzed puma mRNA levels in HCT116 cells following the treatment of Compound F2. Consistent with the results obtained at protein levels, Compound F2 treatment led to a marked induction of puma mRNA (FIG. 8C). The inventors further applied puma-promoter luciferase reporter assay to test whether puma mRNA induction occurred at transcription level. Treatment of HCT116 stably transfected with the puma promoter-driven luciferase reporter with Compound F2 resulted in markedly induction of puma promoter transcription activity (FIG. 8D). These results indicated that Compound F2 regulated the PUMA protein expression at transcriptional level in a p53-independent manner.

To identify the transcription factor responsible for Compound F2 upregulation of PUMA transcription, TFANS-FAC® Transcription Factor Binding Sites Software (Biological Database, Wolfenbüttel, Germany) was used for bioinformatics analysis of the puma promoter region. The results revealed that the promoter region of the human puma gene contains the Heat Shock Factor-1 (HSF-1), Nuclear Factor kappa B (NF-κB), Specific Proteins 1 (SP-1), Activator Protein 1 (AP-1), cAMP response element-binding protein (CREB), cellular homolog of the retroviral v-myc (c-Myc) and forkhead box O3a (FoxO3a) (FIG. 8E). The inventors next examined the expression of total protein and activated form of these transcription factors upon Compound F2 treatment. As shown in FIG. 8F, there was no significant change of c-Fos, Jun-D, phospho-NFκB p65, NFκB p65, NFκB p50, Sp-1 and HSF-1. In contrast, the inhibition of FoxO3a phosphorylation clearly occurred in whole cell lysate treated with Compound F2. The FoxO3a phosphorylation is known to mediate its nuclear translocation and ensuring transactivation (2.29), and this result indicates Compound F2 can induce FoxO3a transactivation through dephosphorylation at Ser 253. The c-Jun phosphorylation also increased in Compound F2 treating HCT116 cells with peak level at 12 hours (FIG. 8F), which was not concurrent with puma mRNA induction and not evolved in Compound F2-induced PUMA upregulation.

The inventors next tested the effect of Compound F2 on FoxO3a transactivation in a HCT116 stably transfected with FoxO3a transcription activity dependent luciferase (4×DBE) reporter containing four FoxO3a consensus binding sites. The results showed that Compound F2 treatment significantly induced FoxO3a transactivation in a time-dependent manner in HCT116 cells (FIG. 8G). To confirm that the induction of PUMA by Compound F2 was mediated by FoxO3a, the inventors compared the effects of Compound F2 on puma promoter activity in a HCT116 cells transfected with FoxO3a binding site mutant puma promoter luciferase reporter (2.14). As expected, FoxO3a binding site mutations abolished the responsiveness of the puma reporter to Compound F2 (FIG. 8H). Taken together, these data suggest the requirement of FoxO3a for the induction of PUMA following drug treatment.

AKT Inhibition and PHLPP1 Induction Drives PUMA and Cancer Cell Apoptosis Induced by Compound F2

Because AKT, an antiapoptotic kinase often activates aberrantly in cancer cells, phosphorylates FoxO3a and prevents its nuclear localization (2.29), the inventors then determined whether AKT is involved in the effect of Compound F2 on PUMA expression. Western blot analyses (FIG. 9A) indicated that the phosphorylation of AKT at Ser 473 was inhibited after exposure to Compound F2 for 12 h or longer, and phosphorylation at Thr 308 was also inhibited after 24 h. Since the inhibited phosphorylation of AKT at Ser 473/Thr 308 and FoxO3a at Ser 253 occurred in late phase (~12 h), the inventors anticipated that the kinase that is responsible for activation of AKT/FoxO3a pathway was not affected by Compound F2, whereas the major late phase inhibition on the phosphorylation of AKT/FoxO3a could be due to altered phosphatase expression.

The phosphorylated AKT is dephosphorylated by tumor suppressor PTEN (2.30) and PHLPP phosphatases (PHLPP1 and PHLPP2) (2.31, 2.32). Therefore, the protein expression of PTEN and PHLPP1, 2 were evaluated in HCT116 cells upon Compound F2 treatment. The results showed that there were no significant differences in PTEN protein expression after Compound F2 treatment (FIG. 9B). However, PHLPP1, not PHLPP2, protein expression was upregulated after drug treatment (FIG. 9B). Since the phosphatase activity of PTEN mainly depends on protein expression (2.33), this result suggested that PHLPP1, not PTEN or PHLPP2, is involved in Compound F2 regulating AKT/FoxO3a pathway.

To further confirm whether PHLPP1 is involved in Compound F2 inhibiting cancer growth through regulating AKT/FoxO3a/PUMA axis, the inventors used shRNA specific targeting PHLPP1 to knockdown this protein expression in HCT116 cells. The results supported the notion that PHLPP1 upregulation by Compound F2 mediated the inhibition of cancer growth through targeting AKT/FoxO3a/PUMA axis.

Discussion

The ability of cancer cells to avoid apoptosis has been identified as one of the major mechanisms for development of cancers (2.38). Here the inventors show that Compound F2, a newly discovered natural isolate, can inhibit anchorage-independent growth and induce cell apoptosis against HCT-116 ($p53^{+/+}$ and $p53^{-/-}$) and p53 mutant HT-29 and DLD cell lines. The inventors also observed caspase-3 and PARP cleavage in Compound F2-treated colon cancer cells, implying apoptosis induction that involved caspases-3 and PARP cleavage. The inventors also found that PUMA plays an important role in the apoptotic response to Compound F2 in human cancer cells through a p53-independent, foxO3a-dependent mechanism. Compound F2-induced foxO3a activation is through the PHLPP1/AKT pathway. The inventors' findings have several important implications in the understanding of apoptosis regulation in human cancer cells.

It is well known that apoptosis induction by conventional chemotherapeutic agents is mediated mostly through p53-dependent pathways. However mutations and alterations in p53 are the most frequent genetic events observed in human cancers, with varying frequencies depending on the cancer type (2.40, 2.41). By utilization of p53 null HCT116 cells, the inventors determined that apoptotic induction of Compound F2 is through p53-independent mechanism. Therefore, Compound F2 may have a potential use in therapeutic applications for patients with p53 mutation in cancer cells. p53 exerts its effects by inducing or repressing numerous genes that are involved in cell cycle arrest, senescence, apoptosis and DNA repair (2.40). PUMA is a p53-target downstream gene and a major mediator of DNA damage-induced, with an essential role in p53-independent apoptosis (2.42). The inventors' results suggest that Compound F2 treatment resulted in the induction of PUMA at protein level (FIG. 7A) and mRNA level (FIG. 8C). Intriguingly, deletion of PUMA was sufficient to render resistant to apoptosis induction effect by Compound F2. Several transcription factors have been implicated in the transcriptional regulation of puma in addition to p53 (2.8, 2.43-2.45). To identify the transcription factor responsible for Compound F2-induced puma transcription, the inventors examined the expression of total protein and activated form of puma regulating related transcription factors upon Compound F2 treatment, and found foxO3a phosphorylation was inhibited by Compound F2 treatment (FIG. 8F). The results also showed that Compound F2 treatment significantly induced FoxO3a transactivation (FIG. 8G), and FoxO3a binding site mutations abolished the responsiveness of the puma reporter to Compound F2 (FIG. 8H). These data implicate FoxO3a as an important regulator of p53-independent PUMA induction following Compound F2-treatment of colon cancer cells.

The mammalian Forkhead homolog FoxO3a is a potent stress response regulator (2.29). FOXO family members participate in various cellular functions, including apoptosis, cell cycle progression, and antioxidant defense (2.46). The role of FoxO3a in causing p53-independent PUMA induction and apoptosis has been highlighted in recent publications (2.9, 2.47). The activity of FoxO3a is negatively regulated by phosphorylation via AKT (2.48). The inventors' study showed that Compound F2-induced AKT dephosphorylation was related with increased expression of phosphatase PHLPP1. In physiological condition, AKT is activated through the receptor-mediated PI3-kinase-dependent signaling pathway. The termination of AKT signal is mediated by phosphatases. For a long time PTEN was considered the only phosphatase to terminate AKT signaling (2.49). In the past several years, two novel serine phosphatases, PHLPP1 and PHLPP2, were discovered to directly dephosphorylate and inactivate AKT (2.31, 2.32). Here the inventors showed that level of PHLPP1 was greatly induced by Compound F2 treatment (FIG. 9B), terminated AKT activation and stimulate cell death. Taken together, the inventors' observations showed that Compound F2 can induce increased PUMA transcription through PHLPP1/AKT pathway.

Cancer is a disorder of deregulated cell proliferation and/or cell survival of genome-damaged cells (2.58) Inhibiting cell proliferation and increasing apoptosis in tumors are effective ways to prevent tumor growth and eliminate cancers. In summary, the inventors' studies demonstrate that Compound F2 upregulated potent tumor suppressor PHLPP1 expression and inhibited pro-survival AKT signaling, subsequent elevated the activation of FoxO3a and its target genes PUMA, and then induce apoptosis and inhibits anchorage-independent growth in colon cancer cells. These results showed a novel signal pathway PHLPP1/AKT/FoxO3a in regulating BH3-only family member PUMA expression and in regulating cancer cell apoptosis in a p53-independent manner. Therefore, Compound F2 may have a potential use in therapeutic applications for patients with p53 mutation in cancer cells.

Example 3

Induction of G0/G1 Cell Cycle Arrest by Compounds F2 Via Upregulating the p53-p21Cip1 Pathway in Mouse Epidermal Cl41 Cells To investigate the anti-tumor promotive effects of Compound F2, the inventors performed experiments to examine the effects of Compound F2 on epidermal growth factor (EGF)-induced cell transformation in Cl41 cells, a mouse epidermal JB6 cell model. As shown in FIG. 10, Compound F2 treatment resulted in marked inhibition of EGF-induced cell transformation. Treatment with Compound F2 arrested Cl41 cells in G0/G1 phase and significantly suppressed the growth of Cl41 cells. Compound F2 also upregulated the expression level of G0/G1 phase regulator p21 (FIG. 11). Compound F2 activated p21 transcription, which depends on p53 (FIG. 12). In summary, the inventors' results suggested that Compound F2 inhibited EGF-induced Cl41 cellular transformation through p53-dependent p21 upregulation, which provided a basis for developing this compound as a novel agent for cancer prevention and proliferation repression.

To reduce the occurrence of cancer, one promising approach is its prevention, specifically by chemical intervention through minor non-nutrient dietary constituents Important to chemoprevention is the fact that carcinogenesis is a long-term process of cellular growth, division and subsequent clonal expansion of initiated cells exemplified by steps known as initiation, promotion and progression (3.1). One advantage of chemoprevention is that agents can be targeted against tumor promotion stage of carcinogenesis. Thus, inhibition or slowing of promotion stage of carcinogenesis can potentially prevent cancers from becoming clinically significant.

The intervention of cancer at the promotion stage, however, seems to be most appropriate and practical. The major reason for this is the fact that tumor promotion is a reversible event at least in early stages and requires repeated and prolonged exposure of a promoting agent (3.2). For this reason, it is important to identify antitumor-promoting agents. A number of compounds have been evaluated by the inventors' laboratory, for their potential chemopreventive activity, and many of them are of plant origin (3.3, 3.4). Therefore, considerable attention has been focused on identifying edible and medicinal phytochemicals that possess the ability to interfere with carcinogenic or mutagenic processes (3.5).

The genus *Goniothalamus* (Annonaceace) consists of 50 species distributed in the tropics and subtropics, of which 10 are found in China (3.6). Several acetogenins, styrylpyrones, and alkaloids have been isolated from the plants in the genus, and their cytotoxic activity against a number of human cancer cell lines has been reported (3.7, 3.8). Compound X is a novel conformation derivative of cheliensisin A, which is a natural styryl-lactone isolated from *Goniothalamus cheliensis* Hu with putative anticancer activities (3.9). Mechanism studies revealed that cheliensisin A induced leukemia cell apoptosis involving activation of caspase-3 and downregulation of Bcl-2 mRNA expression (3.9). In addition to its significant in vitro antitumor activities, cheliensisin A also exhibited potent in vivo antitumor effect on mice (3.10).

In the work presented here, the inventors investigated the cancer preventive and proliferation repression properties of Compound F2. The results demonstrated the anti-proliferative activity of Compound F2 and its effect on cell cycle arrest in Cl41 cells. The inventors assayed the levels of cell cycle control molecules and found that p53-p21 pathway played an important role in the anti-cancer effects of Compound F2. The results provide a mechanistic framework for further exploration of Compound F2 as a novel chemotherapeutic for human tumors Plasmids, Antibodies, and Reagents.

The constructs of p21 promoter-driven luciferase reporters (p21-luc), p21-lucΔRE1, p21-luc ΔRE1/RE2 and p21-luc 200 bp were gifts from Dr. Jennifer A. Pietenpol, Vanderbilt University School of Medicine (3.11). p53 dependent transcription activity-driven luciferase reporter (PG13-Luc) (3.12) and mouse p53 small interfering RNA (p53-siRNA) construct (3.13) were described in the inventors' previously studies. The antibodies against p53 and cyclin B1 were purchased from Cell Signaling Technology Inc (Beverly, Mass.). The antibodies against cyclin E, cyclin D1, CDK4, PUMA were bought from Santa Cruz Biotechnology (Santa Cruz, Calif.). The antibodies against Bax and p21 were purchased from Upstate Biotechnology (Lake Placid, N.Y.). Antibody against β-actin was from Sigma (St. Louis, Mo.).

Compound F2 was prepared according the methods of invention. Compound F2 was dissolved in Dimethyl sulfoxide (DMSO, Santa Cruz Biotechnology) to make a stock concentration at 16 mM and further diluted in McCoy's 5A medium with final DMSO concentration at 0.2% (v/v) for cell culture experiments. The same amount of DMSO was used as a vehicle control in all experiments.

Cell Culture and Transfection.

Mouse epidermal JB6 Cl41 cells and their transfectants were cultured in 5% Fetal bovine serum (FBS) MEM containing with 1% penicillin/streptomycin and 2 mM L-glutamine (Life Technologies, Grand Island, N.Y.), and were maintained at 37° in a 5% $CO_2$. Cell transfections were performed with specific cDNA constructs using PolyJet™ DNA In Vitro Transfection Reagent (SignaGen Laboratories, Gaithersburg, Md.) according to the manufacturer's instructions. For stable transfection selection, cultures were subjected to hygromycin or G418 selection for 4-6 weeks, and surviving cells were pooled as stable mass transfectants as described in the inventors' previous study (3.14).

Anchorage-Independent Growth Assay.

Anchorage-independent growth in soft agar was performed as described previously (3.15). Briefly, $2 \times 10^4$ cells mixed with various concentration of Compound X and 20 ng/ml EGF in 10% FBS modified Eagle's medium (BMEM) containing 0.33% soft agar, was seeded over bottom layer of 0.5% agar in 10% FBS BMEM in each well of 6-well plates. The plates were incubated in 5% $CO_2$ incubator at 37° C. for 3 weeks, and the colonies with more than 16 cells of each were scored and presented as colonies/$1 \times 10^4$ cells.

Cell Cycle Assay.

Cell cycle assay was assessed as previously described in reference (3.16). After the time periods indicated, the Compound X-treated and control cells were harvested and fixed in 75% ethanol. The fixed cells were stained with propidium iodide (PI) solution at 4° C. for 30 minutes and were then examined by flow cytometry utilizing an Epics XL FACS (Beckman Coulter Inc., Miami, Fla.) and EXPO 32 software as described previously (3.17).

Western Blot Assay.

See Example 1 for the method.

Reverse Transcription Polymerase Chain Reaction (RT-PCR).

See Example 1 for the description.

Statistical Methods.

See Example 1 for the description.

Results

Compound F2 Prevented EGF-Induced Anchorage-Independent Colony Formation of Cl41 Cells To investigate the molecular basis or the antitumor promotion effect of Compound F2, the inventors used the JB6 Cl41 cell culture model, a well-established model of anchorage-independent growth in soft agar which represents early stage of cancer promotion (3.20). As reported previously (3.20), EGF induced transformed colonies in soft agar at high frequency (FIGS. 10A & B). Compound F2 significantly repressed EGF-induced cell transformation and colony formation on soft agar, in a dose-dependent manner (FIGS. 10A & B).

To assess whether the inhibitory effects of Compound F on growth inhibition of Cl41 cells is mediated via alteration in cell cycle regulation, the inventors evaluated the effect of Compound F2 on cell cycle distribution. The Cl41 cells were synchronized by 0.1% FBS medium for 24 h, and then cultured with 1% FBS medium containing 8, 16, 32 μM of Compound F2 for 24 h. The flow cytometry analysis showed that the proportion of cells in the G0/G1 phase of the cell cycle increased from 63.49% to 77.74%, 79.79% and 80.13%, respectively (FIG. 10C). These results indicate that Compound F2 treatment inhibits EGF-induced cell transformation and such inhibition of cell transformation might be associated with cell cycle arrests at G0/G1 phase in a dose-dependent manner.

Effects of Compound F2 Treatment on the Expression Levels of Cell-Cycle-Regulatory Proteins To explore the underlying mechanism of G0/G1 cycle arrest induced by Compound F2, the cell cycle regulatory proteins were analyzed by Western Blot. It is known that cyclin D1, cyclin E, cyclin A, CDK4/6 and CDK2 cooperate to promote G0→G1 phase progression (3.21). As shown in FIG. 11A, the protein level of these proteins underwent no change regardless of the dosage applied. Since the CDK activity can also be controlled by a group of CDKIs (3.22), the inventors further examined the effect of Compound F2 on the protein levels of p53, p21 and p27. After exposure to different dose of Compound F2 for 24 hours, the expression levels of p21 and p53 increased by 2 to 32 μM Compound F2 in a dose-dependent manner (FIG. 12A). In contrast, p27 expression did not change. Next, the inventors analyzed the Compound 12-induced cell-cycle regulators expression treated with Compound F2 (16 µM) after indicated time. The results showed that Compound F2 treatment caused p53 and p21 accumulation within several hours, with the peak level at 24 hours (FIG. 12B). It is established that p53 exerts its tumor suppressing functions mainly as a transcription factor and binds to a specific DNA sequence, activating transcription of its target gene cell-cycle-related p21 and p27 and apoptosis-related PUMA and Bax.

Compound F2 Treatment Induced p21 Upregulation at Transcription Level

To clarify the underlying mechanism of Compound F2-induced p21 protein expression, the inventors examined mRNA levels of p21 in comparison to β-actin as control. Consistent with the results obtained at protein levels, Compound F2 treatment led to marked induction of p21 mRNA in dose- and time-dependent manners (FIGS. 12 A & B). The inventors further carried out experiments to evaluate Compound F2-regulated p21 mRNA expression via transcription. The result obtained from Cl41 stably transfected with the p21 promoter-driven luciferase reporter (3.11) showed that Compound F2 treatment resulted in obvious induction of p21 promoter transcription activity in a time-dependent manner (FIG. 12C).

To identify potential DNA elements responsible for p21 transcription following Compound F2 treatment, an ~2.4 kb fragment of the p21 promoter (p21 Luc) and two smaller fragments in this region [ΔRE1, ΔRE1/2 and 200 bp, (3.11)] were stably transfected into Cl41 cells. The schematic representation of these reporters was shown in FIG. 12D and the activities of these reporters induced by Compound X treatment were tested at indicated time. The result indicated that both of RE1 (2.4~1.8 kb) and RE2 (1.8~1.3 kb) were responsible for Compound F2-induced p21 transcription (FIG. 12C).

Compound F2-Induced p21 Transcription was p53-Dependent and Inhibition of p53 Abolished the Compound F2-Induced G0/G1 Arrest in Cl41 Cells To identify the transcription factor responsible for Compound F2 upregulation of p21 transcription, TFANSFAC® Transcription Factor Binding sites Software (Biological Database, Wolfenbüttel, Germany) was used for bioinformatics analysis of the p21 promoter region. The results revealed that the promoter region of the human p21 gene contains the putative DNA-binding site of cellular transcription factor p53, Stat3/5, C/EBP, ADR1, c-Ets and AP-4 (FIG. 14A). Among these transcription factors, Stat3/5 have two groups binding sites on RE1 (2.4~1.8 kb) and RE2 (1.8~1.3 kb) apart from p53. p21 is one of transcriptional targets of p53. At the G0/G1 check-point, p53 induces the expression of p21, leading to the inhibition of CDK activity to allow the arrest of cells at the G1 to S-phase transition (3.25). To study whether upregulation of p21 by Compound F2 was mediated by p53, the inventors tested the effects of Compound F2 on p53 transactivation in Cl41 cells stably transfected with p53-luciferase reporter containing consensus p53 binding sites (PG13-luc) (12). As expected, the results showed that Compound F2 treatment significantly induced p53 transactivation in Cl41 cells (FIG. 13C).

To further explore the cause-effect relationship between the p53 pathway and Compound F2-induced p21 upregulation and G0/G1 cell cycle arrest in Cl41 cells, the expression of p53 was decreased by siRNA. Compared with the control vector transfected cells, p53 siRNA transfected cells displayed less of expression of p53 (FIG. 14A). Moreover, the induction of p21 by Compound F2 after p53 silencing was much less than that observed in the control vector group (FIG. 14B). The si-p53/p21luc cells with normalized level of p21 protein were treated by Compound F2 and subjected to cell cycle analysis. The result indicated that. These data suggest that the up-regulation of p21 is induced by Compound F2 in a p53-dependent manner.

The inventors further investigated whether p53-mediated G0/G1 cell cycle arrest by transactivation of p21 was involved in Compound F2-induced G0/G1 phase arrest in Cl41 cells. The inventors detected the ratio of cells in different cell cycle phases in p53 silenced or non-silenced cells treated with Compound F2 for 24 hours. As shown in FIG. 14E, compared with the irrelevant control siRNA group, the induction of G0/G1 phase arrest by Compound F2 was significantly attenuated in the p53 siRNA group, and the percentage of G0/G1 phase cells dropped. The results demonstrate that the p53-p21 pathway plays a substantial role in Compound F2-induced G0/G1 cell cycle arrest.

Discussion

Chemoprevention, the use of naturally occurring and synthetic agents, to slow the growth, delay the onset, or reverse carcinogenesis is increasingly recognized as an important means for cancer control (3.1, 3.2, 3.5, 3.26). The intervention of cancer at the promotion stage appears to be the most appropriate and practical, because tumor promotion is a reversible event at least in early stages and requires repeated and prolonged exposure of a promoting agent (3.27). Natural compounds originally derived from plants, have historically been regarded as an invaluable source of potential therapeutic agents, and are also are well known to play essential roles in cancer treatments (3.28). In the present report, the inventors presented evidence for the first time to substantiate that the anti-cancer effects of Compound F2 in EGF-induced transformation of Cl41 cells. The data reported here supported the notion that Compound F2 not only inhibited anchorage-independent cell growth of EGF-treated Cl41 cells, but also induced p21 upregulation and G0/G1 growth arrest in the same cells. The upregulation of p21 by Compound F2 occurred at transcription level and was mediated via p53-dependent pathway. Decreased expression of p53 in Cl41 cells attenuated Compound F2 induction of p21 and G0/G1 growth arrest, which indicated that the p53 pathway accounted for its effects on its G0/G1 growth arrest and anti-cancer effect in Cl41 cells.

Compound F2 is a novel conformation derivative of cheliensisin A, which is a natural styryl-lactone isolated from *Goniothalamus cheliensis* Hu with putative anticancer activities (3.9). *Goniothalamus cheliensis* Hu is a small tree or shrub in Yunnan Province, southwest of China. Acetogenins, styryllactones and alkaloids from the genus were reported in the previous literature (3.7, 3.8) and many of them showed strong cytotoxic activities against a number of human cancer cell lines (3.9). The titled plant has been the subject of the inventors' investigation due to the impressive cytotoxicity of its organic extract against multiple cancer cells in preliminary pharmacological screening (3.29). In the present study, the inventors demonstrated Compound F2, a novel conformation derivative of cheliensisin A, had anti-cancer effect in EGF-induced transformation of Cl41 cells, which indicated Compound F2 had potential chemoprevention effect at the cancer promotion stage. Considering the significance of cell cycle progression to tumor growth, the inventors focused on the effects of Compound F2 on cell cycle progression and the potential mechanisms that may contribute to its anti-tumor activity.

The inventors' study demonstrated that Compound F2 exerted its growth inhibitory effects on Cl41 cells mainly by inducing G0/G1 cell cycle arrest (FIG. 11D). Aberrant cell growth and proliferation can lead to tumorigenicity (3.30). The molecular basis for inhibition of cell proliferation by potential chemopreventive agents is being explored (3.31). Eukaryotic cell cycle progression is driven by cyclin-dependent kinases (CDKs) and cyclins. The regulation of CDK-cyclin complex activity also occurs through CDK inhibitors, such as p21 and p27, at checkpoints that halt the cell cycle in response to chemopreventive agents (3.32). Specific overexpression of CDK inhibitors can lead to suppression of tumor growth by cell cycle arrest at the G0/G1 phase, and this provides another possibility for tumor management. In the present report, the inventors have presented evidence to substantiate that the transcriptional process and expression of p21 are upregulated in Compound F2 treated Cl41 cells (FIGS. 12 and 14). The results suggested that the G0/G1 cell cycle arrest induced by Compound F2 is mediated through the p21 upregulation.

The p21 protein, a universal cell cycle inhibitor, binds to cyclin-CDK complexes and proliferating cell nuclear antigen, thereby inducing cell arrest at G0/G1 and blocking cell entry into the S phase. p21 prevents the phosphorylation of Rb via cycling CDK inhibition, thereby allowing Rb to sequester the S phase-necessary transcription factor (E2F), leading to G1 phase arrest (3.38). p21 may also function as an adaptor protein for CDK4-cyclin D complexes, thereby promoting cell cycle progression (3.39). The inventors' results revealed that Compound F2-mediated G0/G1 arrest in Cl41 cells was linked with p21 upregulation, but not p27 (FIGS. 11A & B). The upregulation of p21 enhances the formation of complexes with CDKs and cyclins, thereby inhibiting their activities (3.25, 3.33). The inventors' study further demonstrated that upregulation of p21 induced by Compound F2 was mainly dependent on a transcriptional mechanism rather than a post-translational alteration. The expression of p21 can be regulated by both transcriptional and post-transcriptional mechanisms (3.26), and by the ubiquitin-proteasome system (3.27). The p21 promoter activity was measured to address the question whether the induced expression of mRNA and protein were caused by an upregulation of promoter activity. A similar pattern of induction of p21 promoter activity, as in p21 mRNA and protein levels, was observed in Compound F2-treated Cl41 (FIG. 12). These findings indicate that an enhanced promoter activity, instead of another mechanism such as mRNA stability, may be mainly responsible for the upregulation of p21 gene and protein expression.

At the transcriptional level, p21 is induced either dependently or independently by p53 tumor suppressor protein and by the presence of DNA damaging agents (3.34, 3.35). The tumor suppressor p53 controls a broad range of cellular responses. The induction of a transient (cell cycle arrest) or a permanent (senescence) block of cell proliferation and the activation of cell death pathways in response to genotoxic stress constitute the major arms of the survival—death axis governed by p53 (3.36). In p53-mediated G0/G1 phase arrest, the transactivation of the downstream target p21 is required (3.37). In this study, the inventors observed that Compound F2 activated the p53 pathway by up-regulating its downstream targets p21 (FIGS. 12 C and D). Moreover, the upregulation of p21 mediated by Compound F2 was obstructed by p53 siRNA (FIGS. 14 B, C and D). These results indicate that the p53-mediated pathway may be involved in Compound F2-induced G0/G1 arrest. Furthermore, the inhibition of p53 markedly attenuated the induction of G0/G1 phase arrest by Compound F2 (FIG. 14E). From the above data the inventors conclude that the upregulation of p21 induced by Compound F2 is p53-dependent, and Compound F2-mediated G0/G1 phase arrest is probably carried out through the p53-p21 pathway.

In summary, the inventors' study demonstrated that Compound F2 induced G0/G1 phase arrest through the regulation of p21 in a p53-dependent manner in Cl41 cells. Collectively, these results indicate that the induction of cell cycle arrest by Compound F2 may contribute to its anti-proliferative function in Cl41 cells, and they shed light on the possibility of Compound F2 as an chemopreventive agent.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds of invention given in this application are generated using Open Eye Software's Lexichem naming tool, Symyx Renaissance Software's Reaction Planner or MDL's ISIS Draw Autonom Software tool and not verified. Preferably, in the event of inconsistency, the depicted structure governs.

REFERENCES

Example 1

1.1. Jemal, A., Bray, F., Center, M. M., Ferlay, J., Ward, E., and Forman, D. *CA Cancer J Clin* 61, 69-90
1.2. Lee, K. W., Bode, A. M., and Dong, Z. *Nat Rev Cancer* 11, 211-218
1.3. Yang, C. S., Wang, X., Lu, G., and Picinich, S. C. (2009) *Nat Rev Cancer* 9, 429-439
1.4. Vousden, K. H. (2000) *Cell* 103, 691-694
1.5. Harris, S. L., and Levine, A. J. (2005) *Oncogene* 24, 2899-2908
1.6. Chipuk, J. E., and Green, D. R. (2006) *Cell Death Differ* 13, 994-1002
1.7. Vousden, K. H., and Prives, C. (2009) *Cell* 137, 413-431
1.8. Sax, J. K., and El-Deiry, W. S. (2003) *Cell Death Differ* 10, 413-417
1.9. Bertheau, P., Espie, M., Turpin, E., Lehmann, J., Plassa, L. F., Varna, M., Janin, A., and de The, H. (2008) *Pathobiology* 75, 132-139
1.10. Lu, C., and El-Deiry, W. S. (2009) *Apoptosis* 14, 597-606
1.11. Bunz, F., Hwang, P. M., Torrance, C., Waldman, T., Zhang, Y., Dillehay, L., Williams, J., Lengauer, C., Kinzler, K. W., and Vogelstein, B. (1999) *J Clin Invest* 104, 263-269
1.12. Gartel, A. L., and Tyner, A. L. (2002) *Mol Cancer Ther* 1, 639-649
1.13. el-Deiry, W. S., Tokino, T., Velculescu, V. E., Levy, D. B., Parsons, R., Trent, J. M., Lin, D., Mercer, W. E., Kinzler, K. W., and Vogelstein, B. (1993) *Cell* 75, 817-825
1.14. Coqueret, O. (2003) *Trends Cell Biol* 13, 65-70
1.15. Jung, Y. S., Qian, Y., and Chen, X. *Cell Signal* 22, 1003-1012
1.16. Janicke, R. U., Sohn, D., Essmann, F., and Schulze-Osthoff, K. (2007) *Cell Cycle* 6, 407-413
1.17. Suzuki, A., Tsutomi, Y., Miura, M., and Akahane, K. (1999) *Oncogene* 18, 1239-1244

1.18. Wendt, J., Radetzki, S., von Haefen, C., Hemmati, P. G., Guner, D., Schulze-Osthoff, K., Dorken, B., and Daniel, P. T. (2006) *Oncogene* 25, 972-980
1.19. Adams, J. M., and Cory, S. (2007) *Oncogene* 26, 1324-1337
1.20. Gallenne, T., Gautier, F., Oliver, L., Hervouet, E., Noel, B., Hickman, J. A., Geneste, O., Cartron, P. F., Vallette, F. M., Manon, S., and Juin, P. (2009) *J Cell Biol* 185, 279-290
1.21. Gautier, F., Guillemin, Y., Cartron, P. F., Gallenne, T., Cauquil, N., Le Diguarher, T., Casara, P., Vallette, F. M., Manon, S., Hickman, J. A., Geneste, O., and Juin, P. *Mol Cell Biol* 31, 832-844
1.22. Le, H. V., Minn, A. J., and Massague, J. (2005) *J Biol Chem* 280, 32018-32025
1.23. Zhang, L., Yu, J., Park, B. H., Kinzler, K. W., and Vogelstein, B. (2000) *Science* 290, 989-992
1.24. Fang, Y., Yu, Y., Hou, Q., Zheng, X., Zhang, M., Zhang, D., Li, J., Wu, X. R., and Huang, C. (2012) *J Biol Chem* 287, 35234-35243
1.25. Luo, W., Liu, J., Li, J., Zhang, D., Liu, M., Addo, J. K., Patil, S., Zhang, L., Yu, J., Buolamwini, J. K., Chen, J., and Huang, C. (2008) *J Biol Chem* 283, 8624-8633
1.26. Song, L., Li, J., Ye, J., Yu, G., Ding, J., Zhang, D., Ouyang, W., Dong, Z., Kim, S. O., and Huang, C. (2007) *Mol Cell Biol* 27, 2713-2731
1.27. Ouyang, W., Luo, W., Zhang, D., Jian, J., Ma, Q., Li, J., Shi, X., Chen, J., Gao, J., and Huang, C. (2008) *Environ Health Perspect* 116, 1-6
1.28. Luo, W., Li, J., Zhang, D., Cai, T., Song, L., Yin, X. M., Desai, D., Amin, S., Chen, J., and Huang, C. *Curr Cancer Drug Targets* 10, 96-106
1.29. Wang, L. H. (2004) *Mt Sinai J Med* 71, 361-367
1.30. Parker, S. B., Eichele, G., Zhang, P., Rawls, A., Sands, A. T., Bradley, A., Olson, E. N., Harper, J. W., and Elledge, S. J. (1995) *Science* 267, 1024-1027
1.31. Strobel, T., Swanson, L., Korsmeyer, S., and Cannistra, S. A. (1996) *Proc Natl Acad Sci USA* 93, 14094-14099
1.32. Wu, X., and Deng, Y. (2002) *Frontiers in bioscience: a journal and virtual library* 7, d151-156
1.33. Ghibelli, L., and Diederich, M. (2010) *Mitochondrion* 10, 604-613
1.34. Gartel, A. L., and Tyner, A. L. (1999) *Exp Cell Res* 246, 280-289
1.35. el-Deiry, W. S., Tokino, T., Waldman, T., Oliner, J. D., Velculescu, V. E., Burrell, M., Hill, D. E., Healy, E., Rees, J. L., Hamilton, S. R., and et al. (1995) *Cancer Res* 55, 2910-2919
1.36. Li-Weber, M. *Cancer Lett*
1.37. Agarwal, M. K., Hastak, K., Jackson, M. W., Breit, S. N., Stark, G. R., and Agarwal, M. L. (2006) *Proc Natl Acad Sci USA* 103, 16278-16283
1.38. Efeyan, A., and Serrano, M. (2007) *Cell Cycle* 6, 1006-1010
1.39. Vousden, K. H., and Lane, D. P. (2007) *Nat Rev Mol Cell Biol* 8, 275-283
1.40. Hastak, K., Paul, R. K., Agarwal, M. K., Thakur, V. S., Amin, A. R., Agrawal, S., Sramkoski, R. M., Jacobberger, J. W., Jackson, M. W., Stark, G. R., and Agarwal, M. L. (2008) *Proc Natl Acad Sci USA* 105, 6314-6319
1.41. Resnick, M. A., Tomso, D., Inga, A., Menendez, D., and Bell, D. (2005) *Cell Cycle* 4, 1026-1029
1.42. Wang, J., Ouyang, W., Li, J., Wei, L., Ma, Q., Zhang, Z., Tong, Q., He, J., and Huang, C. (2005) *Cancer Res* 65, 6601-6611
1.43. Vazquez, A., Bond, E. E., Levine, A. J., and Bond, G. L. (2008) *Nat Rev Drug Discov* 7, 979-987
1.44. Menendez, D., Inga, A., and Resnick, M. A. (2009) *Nat Rev Cancer* 9, 724-737
1.45. Vousden, K. H., and Lu, X. (2002) *Nat Rev Cancer* 2, 594-604
1.46. Morachis, J. M., Murawsky, C. M., and Emerson, B. M. *Genes Dev* 24, 135-147
1.47. Tanaka, T., Ohkubo, S., Tatsuno, I., and Prives, C. (2007) *Cell* 130, 638-650
1.48. Jin, Z., and El-Deiry, W. S. (2005) *Cancer Biol Ther* 4, 139-163
1.49. Oltvai, Z. N., Milliman, C. L., and Korsmeyer, S. J. (1993) *Cell* 74, 609-619
1.50. Gorospe, M., Wang, X., and Holbrook, N. J. (1999) *Gene expression* 7, 377-385
1.51. Macleod, K. F., Sherry, N., Hannon, G., Beach, D., Tokino, T., Kinzler, K., Vogelstein, B., and Jacks, T. (1995) *Genes Dev* 9, 935-944
1.52. Aneja, R., Ghaleb, A. M., Zhou, J., Yang, V. W., and Joshi, H. C. (2007) *Cancer Res* 67, 3862-3870

Example 2

2.1. Siegel R, Naishadham D, Jemal A. Cancer statistics, 2012. CA Cancer J Clin; 62: 10-29.
2.2. Segal N H, Saltz L B. Evolving treatment of advanced colon cancer. Annu Rev Med 2009; 60: 207-19.
2.3. Chen X W, Sneed K B, Zhou S F. Pharmacokinetic profiles of anticancer herbal medicines in humans and the clinical implications. Curr Med Chem; 18: 3190-210.
2.4. Soussi T, Lozano G. p53 mutation heterogeneity in cancer. Biochem Biophys Res Commun 2005; 331: 834-42.
2.5. Vogelstein B, Lane D, Levine A J. Surfing the p53 network. Nature 2000; 408: 307-10.
2.6. Yu J, Zhang L. PUMA, a potent killer with or without p53. Oncogene 2008; 27 Suppl 1: S71-83.
2.7. Wang P, Qiu W, Dudgeon C, et al. PUMA is directly activated by NF-kappaB and contributes to TNF-alpha-induced apoptosis. Cell Death Differ 2009; 16: 1192-202.
2.8. Ming L, Sakaida T, Yue W, Jha A, Zhang L, Yu J. Sp1 and p73 activate PUMA following serum starvation. Carcinogenesis 2008; 29: 1878-84.
2.9. You H, Pellegrini M, Tsuchihara K, et al. FOXO3a-dependent regulation of Puma in response to cytokine/growth factor withdrawal. J Exp Med 2006; 203: 1657-63.
2.10. Villunger A, Michalak E M, Coultas L, et al. p53- and drug-induced apoptotic responses mediated by BH3-only proteins puma and noxa. Science 2003; 302: 1036-8.
2.11. Wang P, Yu J, Zhang L. The nuclear function of p53 is required for PUMA-mediated apoptosis induced by DNA damage. Proc Natl Acad Sci USA 2007; 104: 4054-9.
2.12. Jeffers J R, Parganas E, Lee Y, et al. Puma is an essential mediator of p53-dependent and -independent apoptotic pathways. Cancer Cell 2003; 4: 321-8.
2.13. Wu B, Qiu W, Wang P, et al. p53 independent induction of PUMA mediates intestinal apoptosis in response to ischaemia-reperfusion. Gut 2007; 56: 645-54.
2.14. Dudgeon C, Wang P, Sun X, et al. PUMA induction by FoxO3a mediates the anticancer activities of the broad-range kinase inhibitor UCN-01. Mol Cancer Ther; 9: 2893-902.
2.15. Liu J, Weiss H L, Rychahou P, Jackson L N, Evers B M, Gao T. Loss of PHLPP expression in colon cancer: role in proliferation and tumorigenesis. Oncogene 2009; 28: 994-1004.

2.16. Zhang L, Yu J, Park B H, Kinzler K W, Vogelstein B. Role of BAX in the apoptotic response to anticancer agents. Science 2000; 290: 989-92.
2.17. Swamy M V, Herzog C R, Rao C V Inhibition of COX-2 in colon cancer cell lines by celecoxib increases the nuclear localization of active p53. Cancer Res 2003; 63: 5239-42.
2.18. Luo W, Liu J, Li J, et al. Anti-cancer effects of JKA97 are associated with its induction of cell apoptosis via a Bax-dependent and p53-independent pathway. J Biol Chem 2008; 283: 8624-33.
2.19. Song L, Li J, Ye J, et al. p85alpha acts as a novel signal transducer for mediation of cellular apoptotic response to UV radiation. Mol Cell Biol 2007; 27: 2713-31.
2.20. Ouyang W, Zhang D, Ma Q, Li J, Huang C. Cyclooxygenase-2 induction by arsenite through the IKKbeta/NFkappaB pathway exerts an antiapoptotic effect in mouse epidermal Cl41 cells. Environ Health Perspect 2007; 115: 513-8.
2.21. Ouyang W, Luo W, Zhang D, et al. PI-3K/Akt pathway-dependent cyclin D1 expression is responsible for arsenite-induced human keratinocyte transformation. Environ Health Perspect 2008; 116: 1-6.
2.22. Luo W, Li J, Zhang D, et al. Bid mediates anti-apoptotic COX-2 induction through the IKKbeta/NFkappaB pathway due to 5-MCDE exposure. Curr Cancer Drug Targets; 10: 96-106.
2.23. Cai T, Li X, Ding J, Luo W, Li J, Huang C. A cross-talk between NFAT and NF-kappaB pathways is crucial for nickel-induced COX-2 expression in Beas-2B cells. Curr Cancer Drug Targets; 11: 548-59.
2.24. Song L, Gao M, Dong W, et al. p85alpha mediates p53 K370 acetylation by p300 and regulates its promoter-specific transactivity in the cellular UVB response. Oncogene; 30: 1360-71.
2.25. Liu J, Zhang D, Mi X, et al. p27 suppresses arsenite-induced Hsp27/Hsp70 expression through inhibiting JNK2/c-Jun- and HSF-1-dependent pathways. J Biol Chem; 285: 26058-65.
2.26. Freedman V H, Shin S I. Cellular tumorigenicity in nude mice: correlation with cell growth in semi-solid medium. Cell 1974; 3: 355-9.
2.27. Wang L H. Molecular signaling regulating anchorage-independent growth of cancer cells. Mt Sinai J Med 2004; 71: 361-7.
2.28. Yu J, Zhang L. No PUMA, no death: implications for p53-dependent apoptosis. Cancer Cell 2003; 4: 248-9.
2.29. Huang H, Tindall D J. Dynamic FoxO transcription factors. J Cell Sci 2007; 120: 2479-87.
2.30. Stambolic V, Suzuki A, de la Pompa J L, et al. Negative regulation of PKB/Akt-dependent cell survival by the tumor suppressor PTEN. Cell 1998; 95: 29-39.
2.31. Gao T, Furnari F, Newton A C. PHLPP: a phosphatase that directly dephosphorylates Akt, promotes apoptosis, and suppresses tumor growth. Mol Cell 2005; 18: 13-24.
2.32. Brognard J, Sierecki E, Gao T, Newton A C. PHLPP and a second isoform, PHLPP2, differentially attenuate the amplitude of Akt signaling by regulating distinct Akt isoforms. Mol Cell 2007; 25: 917-31.
2.33. Simpson L, Parsons R. PTEN: life as a tumor suppressor. Exp Cell Res 2001; 264: 29-41.
2.34. Trachootham D, Alexandre J, Huang P. Targeting cancer cells by ROS-mediated mechanisms: a radical therapeutic approach? Nat Rev Drug Discov 2009; 8: 579-91.
2.35. Storz P. Forkhead homeobox type O transcription factors in the responses to oxidative stress. Antioxid Redox Signal; 14: 593-605.
2.36. Liou G Y, Storz P. Reactive oxygen species in cancer. Free Radic Res; 44: 479-96.
2.37. Chen Y, Azad M B, Gibson S B. Superoxide is the major reactive oxygen species regulating autophagy. Cell Death Differ 2009; 16: 1040-52.
2.38. Hanahan D, Weinberg R A. Hallmarks of cancer: the next generation. Cell; 144: 646-74.
2.39. Cragg G M, Newman D J, Snader K M. Natural products in drug discovery and development. J Nat Prod 1997; 60: 52-60.
2.40. Vazquez A, Bond E E, Levine A J, Bond G L. The genetics of the p53 pathway, apoptosis and cancer therapy. Nat Rev Drug Discov 2008; 7: 979-87.
2.41. Petitjean A, Mathe E, Kato S, et al Impact of mutant p53 functional properties on TP53 mutation patterns and tumor phenotype: lessons from recent developments in the IARC TP53 database. Hum Mutat 2007; 28: 622-9.
2.42. Yu J, Zhang L. The transcriptional targets of p53 in apoptosis control. Biochem Biophys Res Commun 2005; 331: 851-8.
2.43. Hershko T, Ginsberg D. Up-regulation of Bcl-2 homology 3 (BH3)-only proteins by E2F1 mediates apoptosis. J Biol Chem 2004; 279: 8627-34.
2.44. Melino G, Bernassola F, Ranalli M, et al. p73 Induces apoptosis via PUMA transactivation and Bax mitochondrial translocation. J Biol Chem 2004; 279: 8076-83.
2.45. You H, Mak T W. Crosstalk between p53 and FOXO transcription factors. Cell Cycle 2005; 4: 37-8.
2.46. Tran H, Brunet A, Griffith E C, Greenberg M E. The many forks in FOXO's road. Sci STKE 2003; 2003: RE5.
2.47. Ekoff M, Kaufmann T, Engstrom M, et al. The BH3-only protein Puma plays an essential role in cytokine deprivation induced apoptosis of mast cells. Blood 2007; 110: 3209-17.
2.48. Skurk C, Izumiya Y, Maatz H, et al. The FOXO3a transcription factor regulates cardiac myocyte size downstream of AKT signaling. J Biol Chem 2005; 280: 20814-23.
2.49. Yin Y, Shen W H. PTEN: a new guardian of the genome. Oncogene 2008; 27: 5443-53.
2.50. Schumacker P T. Reactive oxygen species in cancer cells: live by the sword, die by the sword. Cancer Cell 2006; 10: 175-6.
2.51. van Gorp A G, Pomeranz K M, Birkenkamp K U, Hui R C, Lam E W, Coffer P J. Chronic protein kinase B (PKB/c-akt) activation leads to apoptosis induced by oxidative stress-mediated Foxo3a transcriptional up-regulation. Cancer Res 2006; 66: 10760-9.
2.52. Essers M A, Weijzen S, de Vries-Smits A M, et al. FOXO transcription factor activation by oxidative stress mediated by the small GTPase Ral and JNK. EMBO J 2004; 23: 4802-12.
2.53. Sunayama J, Tsuruta F, Masuyama N, Gotoh Y. JNK antagonizes Akt-mediated survival signals by phosphorylating 14-3-3. J Cell Biol 2005; 170: 295-304.
2.54. Sunters A, Madureira P A, Pomeranz K M, et al. Paclitaxel-induced nuclear translocation of FOXO3a in breast cancer cells is mediated by c-Jun NH2-terminal kinase and Akt. Cancer Res 2006; 66: 212-20.
2.55. Cao J, Xu D, Wang D, et al. ROS-driven Akt dephosphorylation at Ser-473 is involved in 4-HPR-mediated apoptosis in NB4 cells. Free Radic Biol Med 2009; 47: 536-47.

2.56. Gong K, Li W. Shikonin, a Chinese plant-derived naphthoquinone, induces apoptosis in hepatocellular carcinoma cells through reactive oxygen species: A potential new treatment for hepatocellular carcinoma. Free Radic Biol Med; 51: 2259-71.

2.57. Hussain A R, Ahmed M, Ahmed S, et al. Thymoquinone suppresses growth and induces apoptosis via generation of reactive oxygen species in primary effusion lymphoma. Free Radic Biol Med; 50: 978-87.

2.58. Evan G I, Vousden K H. Proliferation, cell cycle and apoptosis in cancer. Nature 2001; 411: 342-8.

2.59. Ouyang W, Ma Q, Li J, et al. Cyclin D1 induction through IkappaB kinase beta/nuclear factor-kappaB pathway is responsible for arsenite-induced increased cell cycle G1-S phase transition in human keratinocytes. Cancer Res 2005; 65: 9287-93.

Example 3

3.1. Gupta, S., and Mukhtar, H. (2002) Chemoprevention of skin cancer: current status and future prospects. *Cancer metastasis reviews* 21, 363-380

3.2. Stratton, S. P., Don, R. T., and Alberts, D. S. (2000) The state-of-the-art in chemoprevention of skin cancer. *European journal of cancer* 36, 1292-1297

3.3. Huang, C., Li, J., Song, L., Zhang, D., Tong, Q., Ding, M., Bowman, L., Aziz, R., and Stoner, G. D. (2006) Black raspberry extracts inhibit benzo(a)pyrene diol-epoxide-induced activator protein 1 activation and VEGF transcription by targeting the phosphotidylinositol 3-kinase/Akt pathway. *Cancer Res* 66, 581-587

3.4. Li, J., Zhang, D., Stoner, G. D., and Huang, C. (2008) Differential effects of black raspberry and strawberry extracts on BaPDE-induced activation of transcription factors and their target genes. *Molecular carcinogenesis* 47, 286-294

3.5. Afaq, F., Adhami, V. M., Ahmad, N., and Mukhtar, H. (2002) Botanical antioxidants for chemoprevention of photocarcinogenesis. *Frontiers in bioscience: a journal and virtual library* 7, d784-792

3.6. Wang, S., Zhang, Y. J., Chen, R. Y., and Yu, D. Q. (2002) Goniolactones A-F, six new styrylpyrone derivatives from the roots of Goniothalamus cheliensis. *Journal of natural products* 65, 835-841

3.7. Fang, X. P., Anderson, J. E., Chang, C. J., McLaughlin, J. L., and Fanwick, P. E. (1991) Two new styryl lactones, 9-deoxygoniopypyrone and 7-epi-goniofufurone, from Goniothalamus giganteus. *Journal of natural products* 54, 1034-1043

3.8. Soonthornchareonnon, N., Suwanborirux, K., Bavovada, R., Patarapanich, C., and Cassady, J. M. (1999) New cytotoxic 1-azaanthraquinones and 3-aminonaphthoquinone from the stem bark of Goniothalamus marcanii. *Journal of natural products* 62, 1390-1394

3.9. Zhong, L., Li, C. M., Hao, X. J., and Lou, L. G. (2005) Induction of leukemia cell apoptosis by cheliensisin A involves down-regulation of Bcl-2 expression. *Acta pharmacologica Sinica* 26, 623-628

3.10. Zhao, D., Gong, T., Fu, Y., Nie, Y., He, L. L., Liu, J., and Zhang, Z. R. (2008) Lyophilized Cheliensisin A submicron emulsion for intravenous injection: characterization, in vitro and in vivo antitumor effect. *International journal of pharmaceutics* 357, 139-147

3.11. Westfall, M. D., Mays, D. J., Sniezek, J. C., and Pietenpol, J. A. (2003) The Delta Np63 alpha phosphoprotein binds the p21 and 14-3-3 sigma promoters in vivo and has transcriptional repressor activity that is reduced by Hay-Wells syndrome-derived mutations. *Mol Cell Biol* 23, 2264-2276

3.12. Huang, C., Ma, W. Y., Ryan, C. A., and Dong, Z. (1997) Proteinase inhibitors I and II from potatoes specifically block UV-induced activator protein-1 activation through a pathway that is independent of extracellular signal-regulated kinases, c-Jun N-terminal kinases, and P38 kinase. *Proc Natl Acad Sci USA* 94, 11957-11962

3.13. Wang, J., Ouyang, W., Li, J., Wei, L., Ma, Q., Zhang, Z., Tong, Q., He, J., and Huang, C. (2005) Loss of tumor suppressor p53 decreases PTEN expression and enhances signaling pathways leading to activation of activator protein 1 and nuclear factor kappaB induced by UV radiation. *Cancer Res* 65, 6601-6611

3.14. Fang, Y., Yu, Y., Hou, Q., Zheng, X., Zhang, M., Zhang, D., Li, J., Wu, X. R., and Huang, C. (2012) The Chinese Herb Isolate Isorhapontigenin Induces Apoptosis in Human Cancer Cells by Down-regulating Overexpression of Antiapoptotic Protein XIAP. *J Biol Chem* 287, 35234-35243

3.15. Yan, Y., Li, J., Ouyang, W., Ma, Q., Hu, Y., Zhang, D., Ding, J., Qu, Q., Subbaramaiah, K., and Huang, C. (2006) NFAT3 is specifically required for TNF-alpha-induced cyclooxygenase-2 (COX-2) expression and transformation of Cl41 cells. *Journal of cell science* 119, 2985-2994

3.16. Zhang, J., Ouyang, W., Li, J., Zhang, D., Yu, Y., Wang, Y., Li, X., and Huang, C. (2012) Suberoylanilide hydroxamic acid (SAHA) inhibits EGF-induced cell transformation via reduction of cyclin D1 mRNA stability. *Toxicology and applied pharmacology* 263, 218-224

3.17. Song, L., Li, J., Ye, J., Yu, G., Ding, J., Zhang, D., Ouyang, W., Dong, Z., Kim, S. O., and Huang, C. (2007) p85alpha acts as a novel signal transducer for mediation of cellular apoptotic response to UV radiation. *Mol Cell Biol* 27, 2713-2731

3.18. Ouyang, W., Luo, W., Zhang, D., Jian, J., Ma, Q., Li, J., Shi, X., Chen, J., Gao, J., and Huang, C. (2008) PI-3K/Akt pathway-dependent cyclin D1 expression is responsible for arsenite-induced human keratinocyte transformation. *Environ Health Perspect* 116, 1-6

3.19. Luo, W., Li, J., Zhang, D., Cai, T., Song, L., Yin, X. M., Desai, D., Amin, S., Chen, J., and Huang, C. Bid mediates anti-apoptotic COX-2 induction through the IKKbeta/NFkappaB pathway due to 5-MCDE exposure. *Curr Cancer Drug Targets* 10, 96-106

3.20. Huang, C., Ma, W. Y., Young, M. R., Colburn, N., and Dong, Z. (1998) Shortage of mitogen-activated protein kinase is responsible for resistance to AP-1 transactivation and transformation in mouse JB6 cells. *Proc Natl Acad Sci USA* 95, 156-161

3.21. Obaya, A. J., and Sedivy, J. M. (2002) Regulation of cyclin-Cdk activity in mammalian cells. *Cellular and molecular life sciences: CMLS* 59, 126-142

3.22. Cicenas, J., and Valius, M. (2011) The CDK inhibitors in cancer research and therapy. *Journal of cancer research and clinical oncology* 137, 1409-1418

3.23. Darnell, J. E., Jr., Kerr, I. M., and Stark, G. R. (1994) Jak-STAT pathways and transcriptional activation in response to IFNs and other extracellular signaling proteins. *Science* 264, 1415-1421

3.24. Wen, Z., Zhong, Z., and Darnell, J. E., Jr. (1995) Maximal activation of transcription by Stat1 and Stat3 requires both tyrosine and serine phosphorylation. *Cell* 82, 241-250

3.25. Bartek, J., and Lukas, J. (2001) Pathways governing G1/S transition and their response to DNA damage. *FEBS letters* 490, 117-122

3.26. Bowden, G. T. (2004) Prevention of non-melanoma skin cancer by targeting ultraviolet-B-light signalling. *Nat Rev Cancer* 4, 23-35

3.27. Bickers, D. R., and Athar, M. (2000) Novel approaches to chemoprevention of skin cancer. *The Journal of dermatology* 27, 691-695

3.28. Lee, K. W., Bode, A. M., and Dong, Z. Molecular targets of phytochemicals for cancer prevention. *Nat Rev Cancer* 11, 211-218

3.29. Deng, X., Su, J., Zhao, Y., Peng, L. Y., Li, Y., Yao, Z. J., and Zhao, Q. S. (2011) Development of novel conformation-constrained cytotoxic derivatives of cheliensisin A by embedment of small heterocycles. *European journal of medicinal chemistry* 46, 4238-4244

3.30. Musgrove, E. A., Caldon, C. E., Barraclough, J., Stone, A., and Sutherland, R. L. (2011) Cyclin D as a therapeutic target in cancer. *Nat Rev Cancer* 11, 558-572

3.31. Sarkar, F. H., and Li, Y. (2006) Using chemopreventive agents to enhance the efficacy of cancer therapy. *Cancer Res* 66, 3347-3350

3.32. Vermeulen, K., Van Bockstaele, D. R., and Berneman, Z. N. (2003) The cell cycle: a review of regulation, deregulation and therapeutic targets in cancer. *Cell proliferation* 36, 131-149

3.33. el-Deiry, W. S., Tokino, T., Velculescu, V. E., Levy, D. B., Parsons, R., Trent, J. M., Lin, D., Mercer, W. E., Kinzler, K. W., and Vogelstein, B. (1993) WAFT, a potential mediator of p53 tumor suppression. *Cell* 75, 817-825

3.34. Macleod, K. F., Sherry, N., Hannon, G., Beach, D., Tokino, T., Kinzler, K., Vogelstein, B., and Jacks, T. (1995) p53-dependent and independent expression of p21 during cell growth, differentiation, and DNA damage. *Genes & development* 9, 935-944

3.35. Sheikh, M. S., Li, X. S., Chen, J. C., Shao, Z. M., Ordonez, J. V., and Fontana, J. A. (1994) Mechanisms of regulation of WAF1/Cip1 gene expression in human breast carcinoma: role of p53-dependent and independent signal transduction pathways. *Oncogene* 9, 3407-3415

3.36. Kim, E., Giese, A., and Deppert, W. (2009) Wild-type p53 in cancer cells: when a guardian turns into a blackguard. *Biochemical pharmacology* 77, 11-20

3.37. Chen, C., Chang, Y. C., Liu, C. L., Chang, K. J., and Guo, I. C. (2006) Leptin-induced growth of human ZR-75-1 breast cancer cells is associated with up-regulation of cyclin D1 and c-Myc and down-regulation of tumor suppressor p53 and p21WAF1/CIP1. *Breast cancer research and treatment* 98, 121-132

3.38. Chen, C. Y., Hsu, Y. L., Chen, Y. Y., Hung, J. Y., Huang, M. S., and Kuo, P. L. (2007) Isokotomolide A, a new butanolide extracted from the leaves of *Cinnamomum kotoense*, arrests cell cycle progression and induces apoptosis through the induction of p53/p21 and the initiation of mitochondrial system in human non-small cell lung cancer A549 cells. *European journal of pharmacology* 574, 94-102

3.39. Ocker, M., and Schneider-Stock, R. (2007) Histone deacetylase inhibitors: signalling towards p21cip1/waf1. *The international journal of biochemistry & cell biology* 39, 1367-1374

3.40. Brown, J. M., and Wouters, B. G. (1999) Apoptosis, p53, and tumor cell sensitivity to anticancer agents. *Cancer Res* 59, 1391-1399

3.41. Rokudai, S., Aikawa, Y., Tagata, Y., Tsuchida, N., Taya, Y., and Kitabayashi, I. (2009) Monocytic leukemia zinc finger (MOZ) interacts with p53 to induce p21 expression and cell-cycle arrest. *J Biol Chem* 284, 237-244

3.42. Yu, J., and Zhang, L. (2005) The transcriptional targets of p53 in apoptosis control. *Biochemical and biophysical research communications* 331, 851-858

What is claimed is:

1. A compound according to formula I':

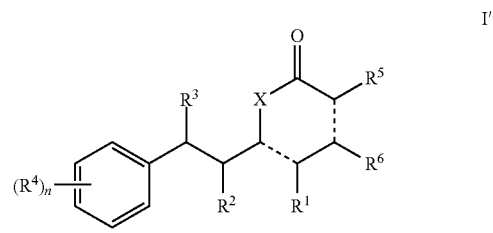

or a pharmaceutically acceptable salt, stereoisomer or tautomer thereof, wherein:

formula I' is selected from the group consisting of:

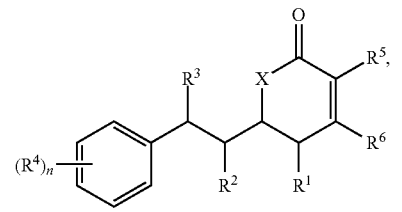

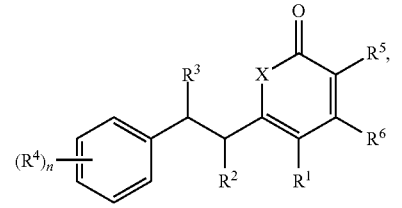

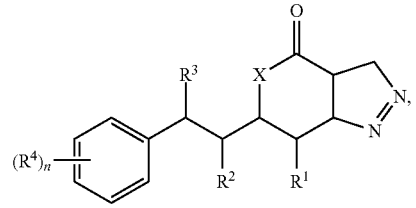

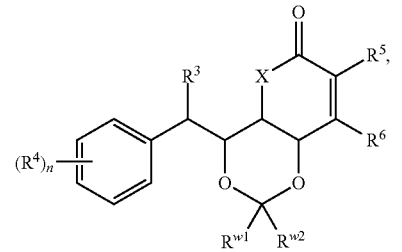

-continued

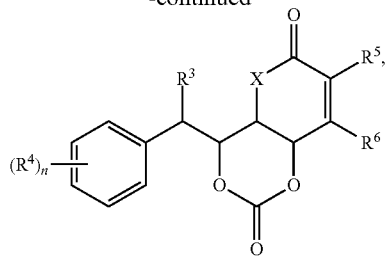

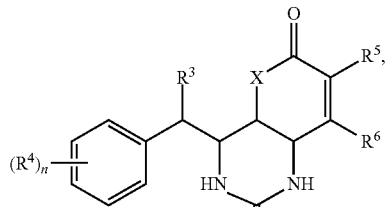

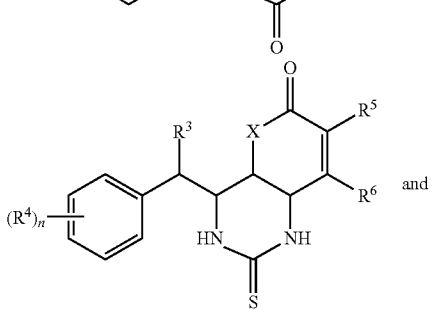

and

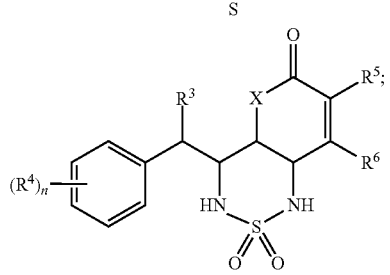

X is —O—;
R$^1$ is H, OH, O—C(O)—R$^{y1}$, NH$_2$, NR$^{z1}$R$^{z2}$ or N(R$^{z3}$)—C(O)—R$^{z4}$;
R$^2$ is H, OH, O—C(O)—R$^{y2}$, NH$_2$, NR$^{z5}$R$^{z6}$ or N(R$^{z7}$)—C(O)—R$^{z8}$;
R$^3$ is H or halo;
each R$^4$ is independently H, OH, unsubstituted alkyl, unsubstituted haloalkyl, unsubstituted alkoxy, unsubstituted acyl, unsubstituted acylamino, unsubstituted alkylamino, unsubstituted alkylthio, unsubstituted alkoxycarbonyl, unsubstituted alkylarylamino, unsubstituted amino, unsubstituted arylalkyl, unsubstituted aminosulfinyl, unsubstituted alkylsulfinyl, unsubstituted arylsulfinyl, unsubstituted aminosulfanyl, unsubstituted alkylsulfanyl, unsubstituted arylsulfanyl, unsubstituted aminosulfonyl, unsubstituted alkylsulfonyl, unsubstituted arylsulfonyl, sulfonic acid, azido, unsubstituted carbamoyl, carboxy, cyano, unsubstituted aryl, unsubstituted heteroaryl, unsubstituted cycloalkyl, unsubstituted heterocycloalkyl, unsubstituted dialkylamino, unsubstituted dialkylamido, halo, nitro or thiol;
R$^5$ and R$^6$ are each independently H;
R$^{w1}$ and R$^{w2}$ are each independently H or unsubstituted alkyl;

R$^{y1}$ and R$^{y2}$ are each independently unsubstituted alkyl, unsubstituted aryl or unsubstituted cycloalkyl;
R$^{z1}$, R$^{z3}$, R$^{z5}$ and R$^{z7}$ are each independently H, unsubstituted alkyl, unsubstituted aryl or unsubstituted cycloalkyl;
R$^{z2}$, R$^{z4}$, R$^{z6}$ and R$^{z8}$ are each independently unsubstituted alkyl, unsubstituted aryl or unsubstituted cycloalkyl; or
R$^{z5}$ and R$^{z6}$, together with the nitrogen atom to which they are attached, form a heterocycle; and
n is 1, 2, 3, 4 or 5;
provided that:
i) when R$^2$ is H, R$^3$ is halo; and
ii) the compound of formula I' is not selected from the group consisting of:

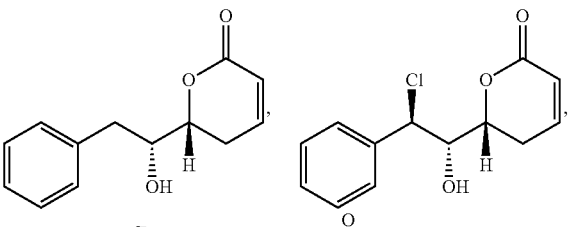

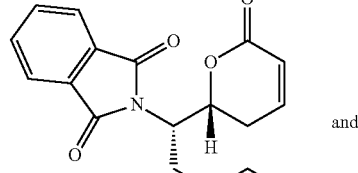

and

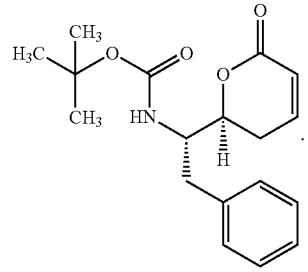

2. The compound according to claim 1, wherein R$^1$ is H or OH.

3. The compound according to claim 1, wherein:
R$^1$ is O—C(O)—R$^{y1}$; and
R$^{y1}$ is unsubstituted alkyl.

4. The compound according to claim 1, wherein R$^1$ is O—C(O)—CH$_3$, O—C(O)—CH$_2$CH$_3$ or O—C(O)—C(CH$_3$)$_3$.

5. The compound according to claim 1, wherein R$^1$ is OH or O—C(O)—C(CH$_3$)$_3$.

6. The compound according to claim 1, wherein R$^1$ is NH$_2$ or NR$^{z1}$R$^{z2}$.

7. The compound according to claim 1, wherein R$^1$ is N(R$^{z3}$)—C(O)—R$^{z4}$.

8. The compound according to claim 1, wherein R$^1$ is NHCH$_3$, NHC(CH$_3$)$_3$, NH—C(O)—CH$_3$ or NH—C(O)—C(CH$_3$)$_3$.

9. The compound according to claim 1, wherein:

$R^2$ is $NR^{z5}R^{z6}$; and $R^{z5}$ and $R^{z6}$, together with the nitrogen atom to which they are attached, form a heterocycle.

10. The compound according to claim 1, wherein $R^2$ is piperidin-1-yl, morpholin-1-yl, pyrrolidin-1-yl or piperazin-1-yl.

11. The compound according to claim 1, wherein $R^2$ is OH.

12. The compound according to claim 1, wherein $R^3$ is H, Cl or F.

13. The compound according to claim 1, wherein $R^3$ is H.

14. The compound according to claim 1, wherein $R^3$ is F.

15. The compound according to claim 1, wherein each $R^4$ is independently H.

16. The compound according to claim 1, wherein:

n is 1 or 2; and each $R^4$ is independently OH, unsubstituted alkyl, unsubstituted haloalkyl, unsubstituted alkoxy, unsubstituted alkylamino, unsubstituted amino, cyano, unsubstituted dialkylamino, halo or nitro.

17. The compound according to claim 1, wherein:

n is 1 or 2; and each $R^4$ is independently OH, $CH_3$, $CF_3$, cyano, $N(CH_3)_2$, F or Cl.

18. The compound according to claim 1, wherein the compound is according to formula I:

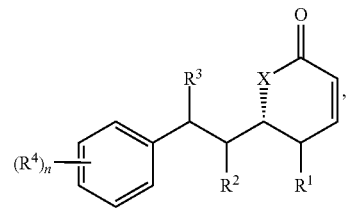

I or a pharmaceutically acceptable salt, stereoisomer or tautomer thereof.

19. The compound according to claim 1, wherein the compound is according to formula IIIa:

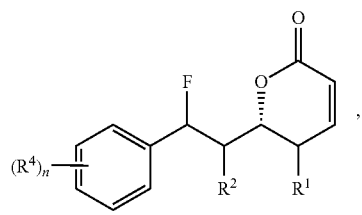

IIIa or a pharmaceutically acceptable salt, stereoisomer or tautomer thereof.

20. The compound according to claim 1, wherein the compound is according to formula IIIc:

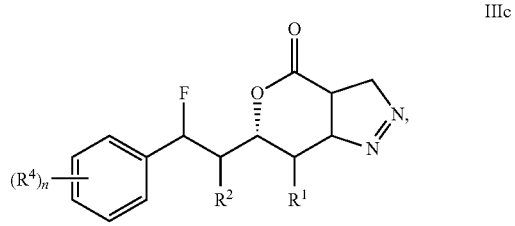

IIIc or a pharmaceutically acceptable salt, stereoisomer or tautomer thereof.

21. The compound according to claim 1, wherein the compound is according to formula IVa, formula IVb or formula IVe:

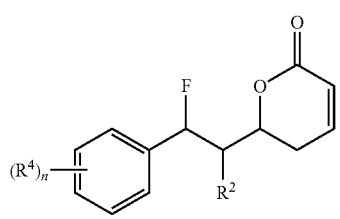

IVa

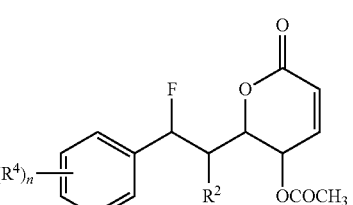

IVb

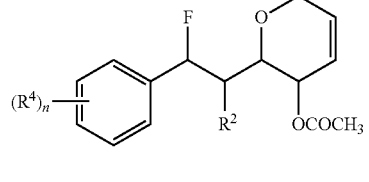

IVe

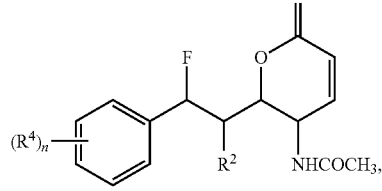

or a pharmaceutically acceptable salt, stereoisomer or tautomer thereof.

22. The compound according to claim 1, wherein the compound is according to formula IVg or formula IVh:

IVg

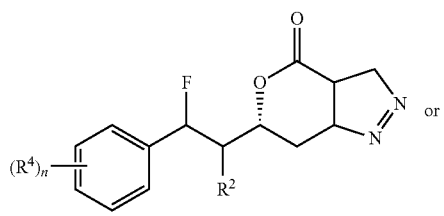

IVh

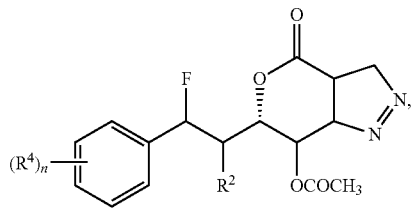

or a pharmaceutically acceptable salt, stereoisomer or tautomer thereof.

23. The compound according to claim 1, wherein the compound is according to formula Va, formula Vb or formula Ve:

Va

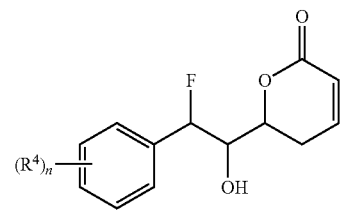

Vb

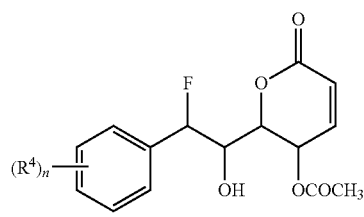

Vc

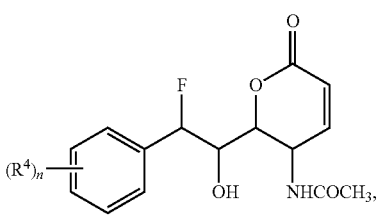

or a pharmaceutically acceptable salt, stereoisomer or tautomer thereof.

24. The compound according to claim 1, wherein the compound is according to formula Vg or formula Vh:

Vg

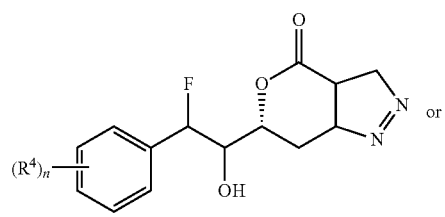

Vh

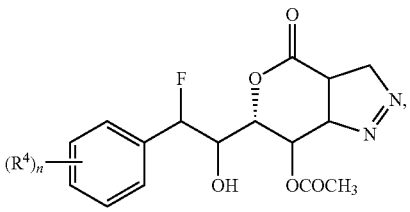

or a pharmaceutically acceptable salt, stereoisomer or tautomer thereof.

25. The compound according to claim 1, wherein the compound is according to formula VIa, formula VIb, formula VIc, formula VId or formula VIe:

VIa

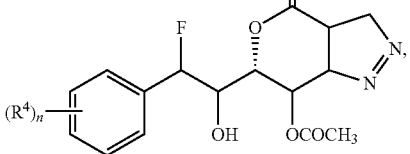

VIb

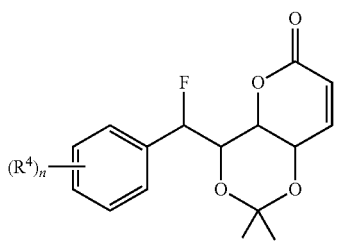

VIc

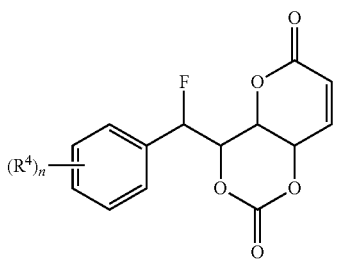

VId

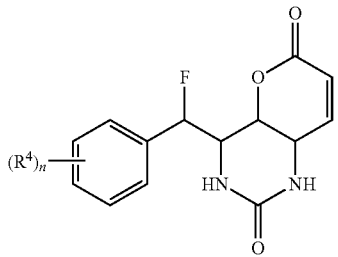

-continued

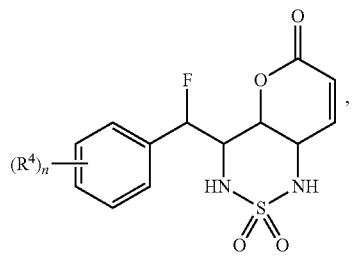

VIe or a pharmaceutically acceptable salt, stereoisomer or tautomer thereof.

26. The compound according to claim 1, wherein the compound is selected from the group consisting of formula VIIa, formula VIIb and formula VIIe:

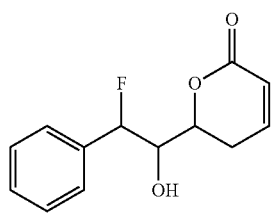

VIIa

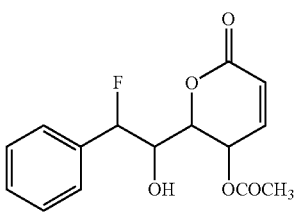

VIIb

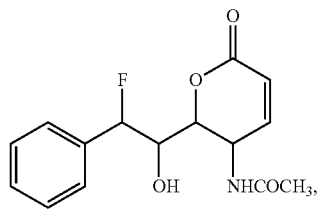

VIIe or a pharmaceutically acceptable salt, stereoisomer or tautomer thereof.

27. The compound according to claim 1, wherein the compound is selected from the group consisting of formula VIIg and formula VIIh:

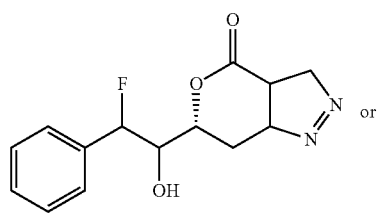

VIIg

-continued

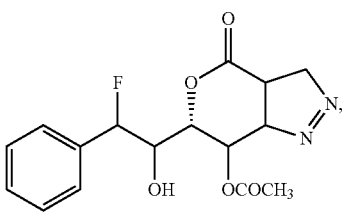

VIIh or a pharmaceutically acceptable salt, stereoisomer or tautomer thereof.

28. The compound according to claim 1, wherein the compound is according to formula VIIIa, formula VIIIb, formula VIIIc, formula VIIId or formula VIIIe:

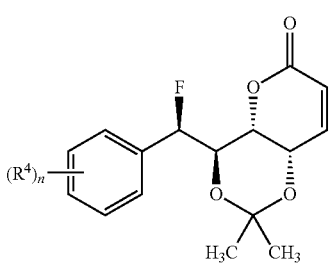

VIIIa

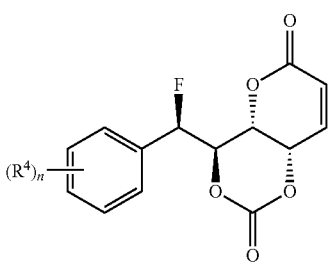

VIIIb

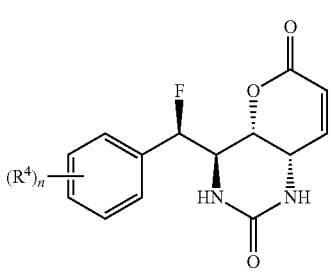

VIIIc

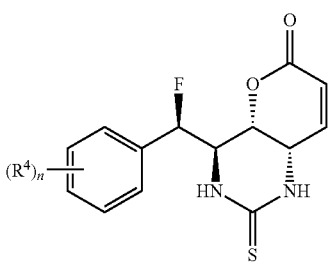

VIIId

VIIIe

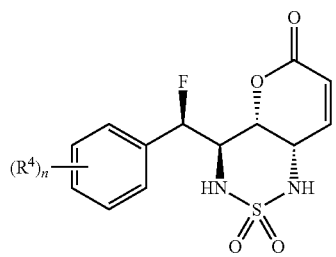

or a pharmaceutically acceptable salt, stereoisomer or tautomer thereof.

29. The compound according to claim 1, wherein the compound is selected from the group consisting of formula IXa, formula IXb and formula IXe:

IXa

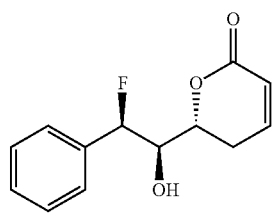

IXb

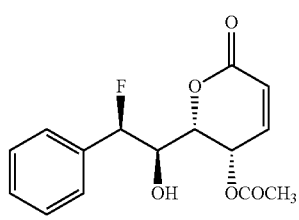

IXe

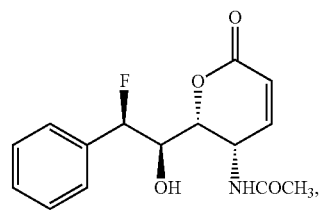

or a pharmaceutically acceptable salt, stereoisomer or tautomer thereof.

30. The compound according to claim 1, wherein the compound is according to formula IXb:

IXb

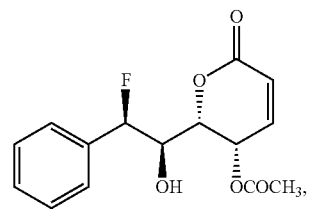

or a pharmaceutically acceptable salt thereof.

31. The compound according to claim 1, wherein the compound is selected from the group consisting of formula IXg and formula IXh:

IXg

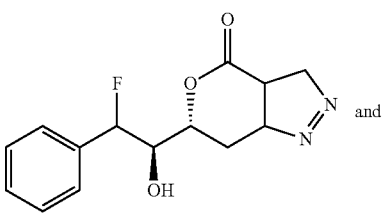

and

IXh

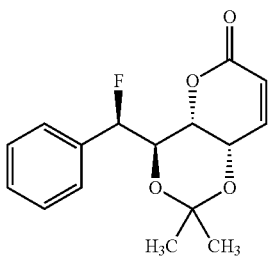

or a pharmaceutically acceptable salt, stereoisomer or tautomer thereof.

32. The compound according to claim 1, wherein the compound is selected from the group consisting of formula Xa, formula Xb, formula Xc, formula Xd and formula Xe:

Xa

Xb

Xc

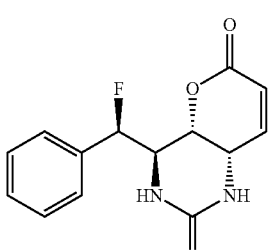

91
-continued
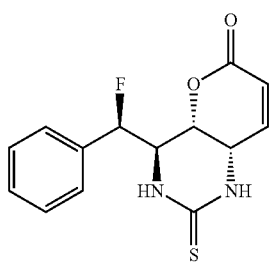
Xd
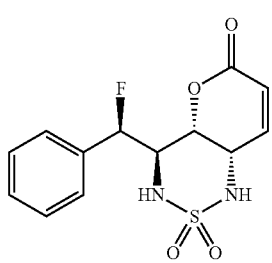
Xe
or a pharmaceutically acceptable salt, stereoisomer or tautomer thereof.
33. The compound according to claim 1, wherein the compound is selected from the group consisting of:
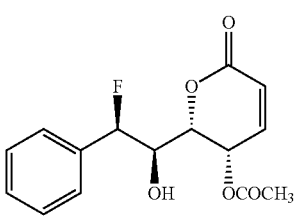
2
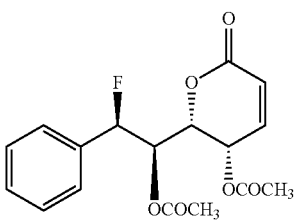
3
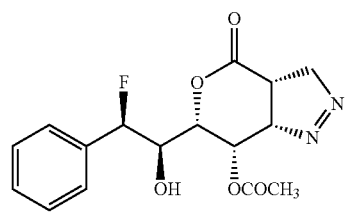
4
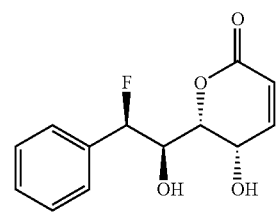
5
92
-continued
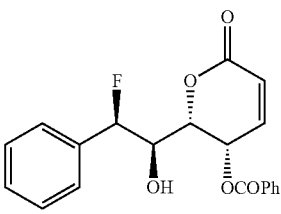
6
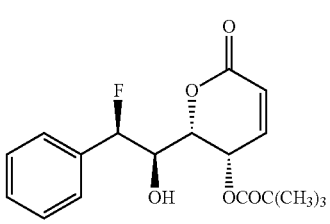
7
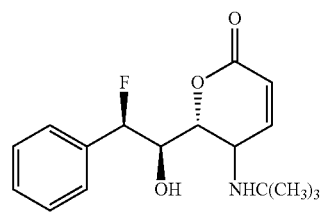
8
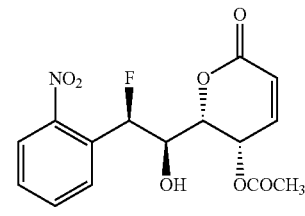
10
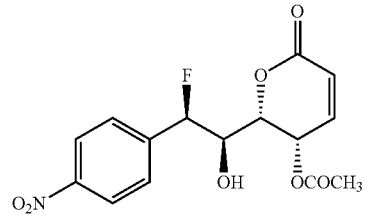
11
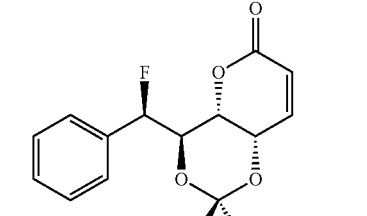
12
and
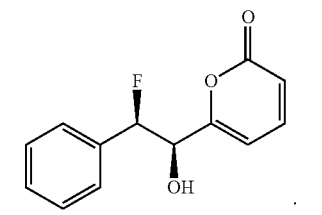
13

34. A pharmaceutical composition comprising a compound according to claim 1 and a pharmaceutically acceptable carrier.

35. The pharmaceutical composition according to claim 34, wherein the pharmaceutically acceptable carrier is parenteral, oral or topical.

36. A method for modulating p53 activity in a mammal, which comprises administering to the mammal a therapeutically effective amount of a compound according to claim 1, or a pharmaceutically acceptable salt, stereoisomer or tautomer thereof.

37. The method according to claim 36, wherein the mammal suffers from cancer.

38. The method according to claim 37, wherein the cancer is selected from the group consisting of melanoma, glioblastoma, prostate cancer, colon cancer, bladder cancer, liver cancer, breast cancer, cervical cancer, ovarian cancer, esophageal cancer and lung cancer.

39. A compound according to formula IVc, formula IVd or formula IVf:

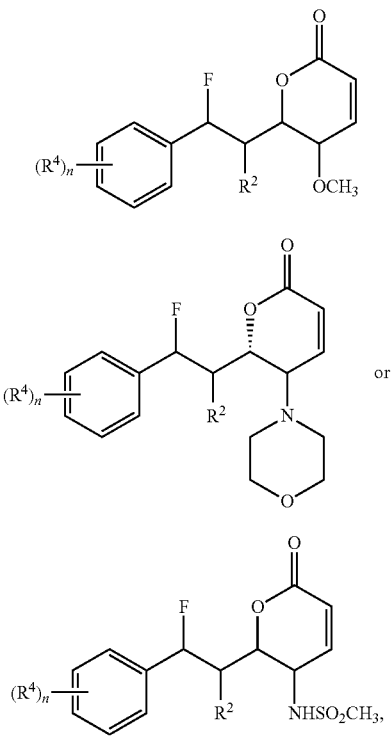

or a pharmaceutically acceptable salt, stereoisomer or tautomer thereof,
wherein:
R$^2$ is H, OH, O—C(O)—R$^{y2}$, NH$_2$, NR$^{z5}$R$^{z6}$ or N(R$^{z7}$)—C(O)—R$^{z8}$;
each R$^4$ is independently H, OH, unsubstituted alkyl, unsubstituted haloalkyl, unsubstituted alkoxy, unsubstituted acyl, unsubstituted acylamino, unsubstituted alkylamino, unsubstituted alkylthio, unsubstituted alkoxycarbonyl, unsubstituted alkylarylamino, unsubstituted amino, unsubstituted arylalkyl, unsubstituted aminosulfinyl, unsubstituted alkylsulfinyl, unsubstituted arylsulfinyl, unsubstituted aminosulfanyl, unsubstituted alkylsulfanyl, unsubstituted arylsulfanyl, unsubstituted aminosulfonyl, unsubstituted alkylsulfonyl, unsubstituted arylsulfonyl, sulfonic acid, azido, unsubstituted carbamoyl, carboxy, cyano, unsubstituted aryl, unsubstituted heteroaryl, unsubstituted cycloalkyl, unsubstituted heterocycloalkyl, unsubstituted dialkylamino, unsubstituted dialkylamido, halo, nitro or thiol;
R$^{y2}$ is unsubstituted alkyl, unsubstituted aryl or unsubstituted cycloalkyl;
R$^{z5}$ and R$^{z7}$ are each independently H, unsubstituted alkyl, unsubstituted aryl or unsubstituted cycloalkyl;
R$^{z6}$ and R$^{z8}$ are each independently unsubstituted alkyl, unsubstituted aryl or unsubstituted cycloalkyl; or
R$^{z5}$ and R$^{z6}$, together with the nitrogen atom to which they are attached, form a heterocycle; and
n is 1, 2, 3, 4 or 5.

40. A compound according to formula Vc, formula Vd or formula Vf:

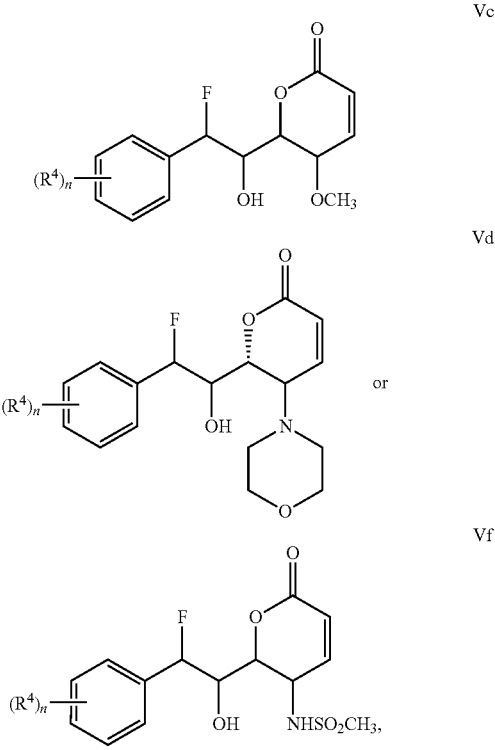

or a pharmaceutically acceptable salt, stereoisomer or tautomer thereof,
wherein:
each R$^4$ is independently H, OH, unsubstituted alkyl, unsubstituted haloalkyl, unsubstituted alkoxy, unsubstituted acyl, unsubstituted acylamino, unsubstituted alkylamino, unsubstituted alkylthio, unsubstituted alkoxycarbonyl, unsubstituted alkylarylamino, unsubstituted amino, unsubstituted arylalkyl, unsubstituted aminosulfinyl, unsubstituted alkylsulfinyl, unsubstituted arylsulfinyl, unsubstituted aminosulfanyl, unsubstituted alkylsulfanyl, unsubstituted arylsulfanyl, unsubstituted aminosulfonyl, unsubstituted alkylsulfonyl, unsubstituted arylsulfonyl, sulfonic acid, azido, unsubstituted carbamoyl, carboxy, cyano, unsubstituted aryl, unsubstituted heteroaryl, unsubstituted cycloalkyl, unsubstituted heterocycloalkyl, unsubstituted dialkylamino, unsubstituted dialkylamido, halo, nitro or thiol; and
n is 1, 2, 3, 4 or 5.

41. A compound selected from the group consisting of formula VIIc, formula VIId and formula VIIf:

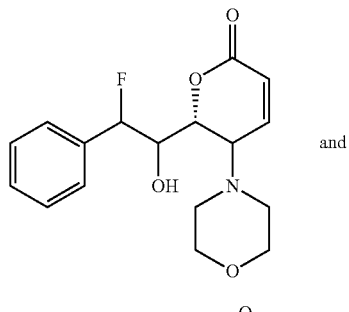
VIIc

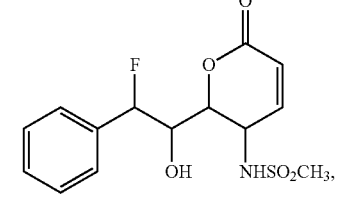
VIId and

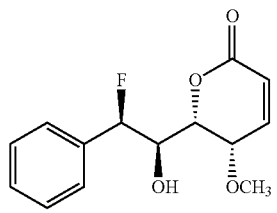
VIIf or a pharmaceutically acceptable salt, stereoisomer or tautomer thereof.

42. A compound selected from the group consisting of formula IXc, formula IXd and formula IXf:

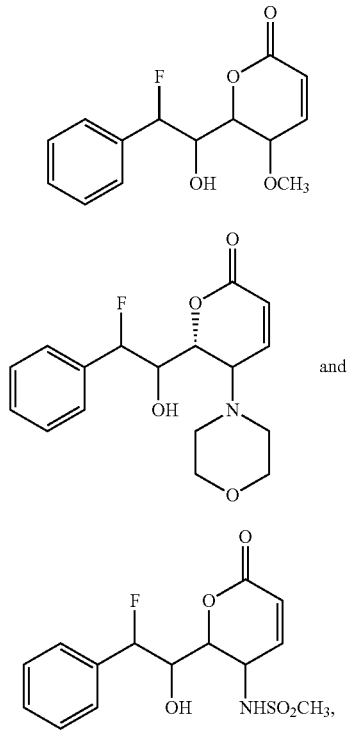
IXc

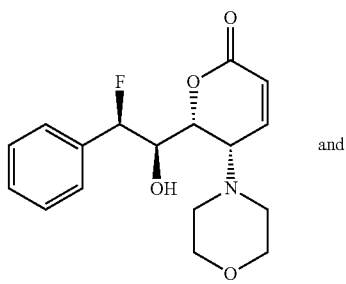
IXd and

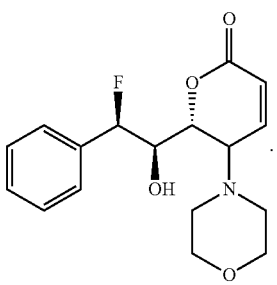
IXf or a pharmaceutically acceptable salt, stereoisomer or tautomer thereof.

43. A compound according to formula 13:

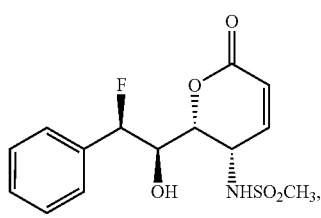
9

* * * * *